US011046714B2

(12) United States Patent
Amjad et al.

(10) Patent No.: US 11,046,714 B2
(45) Date of Patent: Jun. 29, 2021

(54) 2,2-DIFLUORODIOXOLO $A_{2A}$ RECEPTOR ANTAGONISTS

(71) Applicants: Merck Sharp & Dohme Corp., Rahway, NJ (US); Ali Amjad, Edison, NJ (US); Gioconda V. Gallo, Berkely Heights, NJ (US); Timothy J. Henderson, Natick, MA (US); Rongze Kuang, Green Brook, NJ (US); Yeon-Hee Lim, Piscataway, NJ (US); Michael Man-Chu Lo, Rahway, NJ (US); Edward Metzger, Laurel, MD (US); Manuel de Lera Ruiz, Perkasie, PA (US); Andrew Stamford, Morristown, NJ (US); Paul Tempest, Shanghai (CN); Brent Whitehead, Morristown, NJ (US); Heping Wu, Rahway, NJ (US)

(72) Inventors: Ali Amjad, Edison, NJ (US); Gioconda V. Gallo, Berkely Heights, NJ (US); Timothy J. Henderson, Natick, MA (US); Rongze Kuang, Green Brook, NJ (US); Yeon-Hee Lim, Piscataway, NJ (US); Michael Man-Chu Lo, Rahway, NJ (US); Edward Metzger, Laurel, MD (US); Manuel de Lera Ruiz, Perkasie, PA (US); Andrew Stamford, Morristown, NJ (US); Paul Tempest, Shanghai (CN); Brent Whitehead, Morristown, NJ (US); Heping Wu, Rahway, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 190 days.

(21) Appl. No.: 14/914,843

(22) PCT Filed: Aug. 25, 2014

(86) PCT No.: PCT/US2014/052442
§ 371 (c)(1),
(2) Date: Feb. 26, 2016

(87) PCT Pub. No.: WO2015/031221
PCT Pub. Date: Mar. 5, 2015

(65) Prior Publication Data
US 2016/0214997 A1    Jul. 28, 2016

(30) Foreign Application Priority Data

Aug. 29, 2013 (WO) .............. PCT/CN2013/082560

(51) Int. Cl.
*C07D 519/00* (2006.01)
*C07D 491/147* (2006.01)

(52) U.S. Cl.
CPC ....... *C07D 519/00* (2013.01); *C07D 491/147* (2013.01)

(58) Field of Classification Search
CPC .................. C07D 491/147; C07D 519/00
See application file for complete search history.

(56) References Cited

U.S. PATENT DOCUMENTS

| 4,053,600 A * | 10/1977 | Hardtmann ........ C07D 487/04 514/183 |
| 6,369,064 B1 | 4/2002 | Brown et al. |
| 2006/0128732 A1 | 6/2006 | Shimada et al. |
| 2011/0152310 A1 | 5/2011 | Burlison et al. |

FOREIGN PATENT DOCUMENTS

WO    WO-0214321 A1 * 2/2002 ........... A61K 31/519

OTHER PUBLICATIONS

Stone et al. Adenosine receptors in Health and Disease, vol. 193 of the series handbook of experimental Pharmacology, 2009, pp. 535-587.*
Shook et al. ACS Chem. Neurosci., 2011, 2(10), pp. 555-567.*
Patani et al. 1996, Chem. Rev., vol. 96, pp. 3147-3176.*
European search report for 14840648.1 dated Dec. 19, 2016.
International Preliminary Report on Patentability for PCT/US2014/052442 dated Mar. 10, 2016.
Lima, Bioisosterism: A Useful Strategy for Molecular Modification and Drug Design, 2005, 23-49, vol. 12, No. 1.
Colotta, et al., 1,2,4-Triazolo[4,3-a]quinoxalin-1-one: A Versatile Tool for the Synthesis of, Journal of Medicinal Chermistry, 2000, 43(6).
Patent Cooperation Treaty PCT International Search Report, Applicant, No. PCT/CN2013/082560.

* cited by examiner

*Primary Examiner* — Kara R McMillian
(74) *Attorney, Agent, or Firm* — Janet E. Fair; Catherine D. Fitch

(57) ABSTRACT

The present invention is directed to 2,2-difluorodioxolo compounds that are antagonists of $A_{2A}$ receptor. The present invention is also directed to uses of the 2,2-difluorodioxolo compounds described herein in the potential treatment or prevention of neurological disorders and diseases in which $A_{2A}$ receptor are involved. The present invention is also directed to pharmaceutical compositions comprising these compounds and to uses of these pharmaceutical compositions in the prevention or treatment of such diseases in which $A_{2A}$ receptors are involved.

14 Claims, No Drawings

2,2-DIFLUORODIOXOLO $A_{2A}$ RECEPTOR ANTAGONISTS

BACKGROUND OF THE INVENTION

Adenosine is known to be an endogenous modulator of a number of physiological functions. Adenosine action is mediated by the interaction with different membrane specific receptors that belong to the family of receptors coupled with G proteins. Biochemical and pharmacological studies, together with advances in molecular biology, have allowed the identification of at least four subtypes of adenosine receptors: $A_1$, $A_{2A}$, $A_{2b}$ and $A_3$. $A_1$ and $A_3$ are high-affinity receptors, inhibiting the activity of the enzyme adenylate cyclase, and $A_{2A}$ and $A_{2b}$ are low-affinity receptors, stimulating the activity of the same enzyme. Advances in understanding the role of adenosine and its receptors in biological mechanisms have identified potential therapeutic areas for drug development in a variety of physiological and pathophysiological functions, such as cardiac rhythm and circulation, lipolysis, renal blood flow, immune function, sleep regulation, angiogenesis, inflammatory diseases, ischaemia-reperfusion and neurodegenerative disorders (see, e.g., Chen et al., 2013, *Nat. Rev. Drug Discov.* 12:265-286).

In the central nervous system (CNS), adenosine is a potent endogenous neuromodulator, which controls the presynaptic release of many neurotransmitters and is thus involved in motor function, sleep, anxiety, pain and psychomotor activity. The main adenosine receptor subtypes in the brain are $A_1$ and $A_{2A}$. The $A_1$ adenosine receptor subtype is found throughout the brain in high density. Adenosine $A_1$ receptor antagonists that penetrate the CNS are known to reduce the seizure threshold and are potentially pro-convulsant (see, e.g., Cotter et al., 2008, *Journal of Cardiac Failure* 8:631-640). The distribution of the $A_{2A}$ receptor is more restricted, and it is found in high density in the striatum of the basal ganglia (caudate-putamen, nucleus accumbens, olfactory tubercule), where it is co-localized with the dopamine $D_2$ receptor on striatopallidal output neurons. The discrete localization of the $A_{2A}$ receptor within the striatum and its ability to functionally antagonize the actions of the $D_2$ receptor has led to the suggestion of the potential utility of $A_{2A}$ receptor antagonists to improve motor impairment resulting from neurodegenerative diseases, for example, Parkinson's disease, senile dementia as in Alzheimer's disease, Huntington's disease and psychoses of organic origin (see, e.g., Cunha et al., 2008, *Curr. Pharm. Des.* 14:1512-1524; Tuite P, et al., 2003, *J. Expert Opin. Investig. Drugs* 12:1335-52; Popoli P. et al., 2002, *J Neurosci.* 22:1967-75).

Movement disorders constitute a serious health problem, especially among the elderly. These movement disorders can often be the result of brain lesions. Disorders involving the basal ganglia that result in movement disorders include Parkinson's disease, Huntington's chorea and Wilson's disease. Parkinson's disease is characterized by progressive degeneration of the nigrostriatal dopaminergic pathway. The subsequent reduction in striatal dopamine levels is responsible for motor symptoms associated with Parkinson's disease, e.g., the loss of fine motor control or motor impairment manifested in those suffering from the disease. While tremor, rigidity, akinesia and postural changes are four classic symptoms of Parkinson's disease, the disease is also associated with sleep disorders, depression, anxiety, psychosis, dementia and overall cognitive decline (Jankovic, 2008, *J. Neurol. Neurosurg. Psychiatry* 79:368-376). Parkinson's disease is a progressive, incurable disorder with no definite preventive treatment, although drugs are available to alleviate the symptoms and/or slow the progress of the disease. Current therapy is based on dopamine replacement therapy within the presynaptic terminal, for example, by administering L-DOPA (a dopamine precursor), direct stimulation of the postsynaptic $D_2$ receptors, or inhibiting metabolism, for example, by administering monoamine oxidase type B (MAO-B) or catechol-O-methyltransferase (COMT). While L-DOPA is the mainstay in the treatment of Parkinson's disease, because of tolerance problems and a wide range of adverse reactions, including involuntary movements and vomiting, which become progressively more severe with continued treatment, a strong demand for new therapies exists. To this end, highly selective $A_{2A}$ antagonists have demonstrated their efficacy in reducing motor symptoms associated with neurodegenerative diseases, such as Parkinson's disease (see, e.g., Shook and Jackson, 2011, *ACS Chem. Neurosci.* 2:555-567).

Antagonists of the $A_{2A}$ receptor are also potentially useful therapies for the treatment of addiction. Major drugs of abuse (opiates, cocaine, ethanol, and the like) either directly or indirectly modulate dopamine signaling in neurons, particularly those found in the nucleus accumbens, which contains high levels of $A_{2A}$ receptors. Dependence has been shown to be augmented by the adenosine signaling pathway, and it has been shown that administration of an $A_{2A}$ receptor antagonist reduces the craving for addictive substances ("The Critical Role of Adenosine $A_{2A}$ Receptors and $G_i$ $\beta\gamma$ Subunits in Alcoholism and Addiction: From Cell Biology to Behavior", by Ivan Diamond and Lina Yao (The Cell Biology of Addiction, 2006, pp 291-316) and "Adaptations in Adenosine Signaling in Drug Dependence: Therapeutic Implications", by Stephen P. Hack and Macdonald J. Christie, Critical Review in Neurobiology, Vol. 15, 235-274 (2003)).

There remains a continuing need for new therapies for the treatment of diseases and disorders related to the adenosine signaling pathway. In particular, $A_{2A}$ receptor antagonists are believed to be useful in alleviating motor symptoms associated with neurodegenerative diseases, including Parkinson's disease. Such compounds would provide an expansion of the arsenal of compounds that may have value in the treatment of central nervous system disorders, in particular treating or managing the progression of such diseases.

SUMMARY OF THE INVENTION

The present invention is directed to 2,2-difluorodioxolo compounds that are antagonists of $A_{2A}$-receptors. The present invention is also directed to uses of the 2,2-difluorodioxolo compounds described herein in the potential treatment or prevention of disorders and diseases in which $A_{2A}$-receptors are involved, including but not limited to the potential treatment of neurological disorders, including movement disorders, in which $A_{2A}$ receptors are involved. The present invention is also directed to pharmaceutical compositions comprising these compounds and to uses of these pharmaceutical compositions in the potential prevention or treatment of such diseases in which $A_{2A}$-receptors are involved.

DETAILED DESCRIPTION OF THE INVENTION

The present invention is directed to compounds of the formula I:

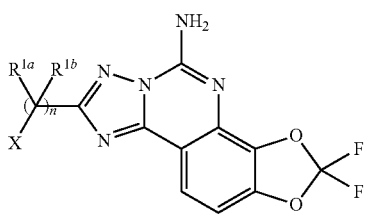

wherein:
R$^{1a}$ and R$^{1b}$ are independently selected from the group consisting of:
(1) hydrogen,
(2) halogen,
(3) hydroxyl,
(4) C$_{1-6}$ alkyl, unsubstituted or substituted with one or more halogen,
(5) C$_{3-6}$ cycloalkyl, and
(6) carbonyl;
X is selected from hydrogen or

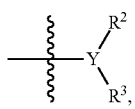

wherein:
Y is CH or N; and,
R$^2$ and R$^3$ are independently selected from the group consisting of:
(1) hydrogen,
(2) C$_{1-6}$alkyl, unsubstituted or substituted with one or more halogen, hydroxy, phenyl (optionally substituted with C$_{1-6}$alkyl, halogen or CF$_3$), C$_{3-6}$cycloalkyl, or a mono- or bicyclic heterocyclic moiety comprising up to 8 carbon atoms and one or more heteroatoms selected from N, S, or O (optionally substituted with C$_{1-6}$ alkyl),
(3) C$_{3-6}$cycloalkyl, unsubstituted or substituted with one or more halogen or C$_{1-6}$ alkyl (optionally substituted with one or more halogen),
(4) —(C=O)O—C$_{1-6}$alkyl, and
(5) a mono- or bicyclic heterocyclic moiety comprising up to 8 carbon atoms and one or more heteroatoms selected from N, S, or O (optionally substituted with C$_{1-6}$ alkyl);
or R$^2$ and R$^3$ are joined to form a cyclic moiety selected from:
(1) C$_{3-6}$ cycloalkyl, unsubstituted or substituted with one or more substituents selected from R$^4$, or
(2) a mono- or bicyclic heterocyclic moiety comprising up to 10 carbon atoms and one or more heteroatoms selected from N, S, or O, unsubstituted or substituted on either a carbon or a heteroatom with one or more substituents selected from R$^4$;
R$^4$ is selected from the group consisting of:
(1) hydroxyl,
(2) halogen,
(3) C$_{1-6}$alkyl, optionally substituted with one or more halogen or C$_{3-6}$cycloalkyl,
(4) —C$_{3-6}$cycloalkyl,
(5) —O—C$_{1-6}$alkyl,
(6) —(O)$_m$—(CH$_2$)$_p$O—C$_{1-3}$alkyl,
(7) oxo,
(8) —O$_m$-phenyl, where the phenyl is optionally substituted with halogen, C$_{1-6}$alkyl or —O—C$_{1-6}$alkyl (wherein the C$_{1-6}$alkyl or —O—C$_{1-6}$alkyl are substituted with —O—C$_{1-6}$alkyl), and,
(9) heterocycle, which is optionally substituted with one or more halogen, C$_{1-6}$alkyl, or phenyl (optionally substituted with halogen or CF$_3$);
wherein if two R$^4$ substituents are attached to the same carbon atom, they may optionally be joined to form a spirocyclic moiety;
m is 0 or 1 (wherein if m is 0, a bond is present);
n is 0, 1, 2 or 3 (wherein if n is 0, a bond is present); and,
p is 1, 2 or 3;
or a pharmaceutically acceptable salt thereof.

An embodiment of the present invention includes compounds wherein R$^{1a}$ and Rib are independently selected from the group consisting of: hydrogen, C$_{1-6}$alkyl (optionally substituted with one or more halogen) and C$_{3-6}$cycloalkyl. In a further embodiment, R$^{1a}$ and R$^{1b}$ are independently selected from the group consisting of hydrogen, C$_{1-6}$alkyl (optionally substituted with one or more fluoro) and C$_{3-6}$ cycloalkyl. In another embodiment, R$^{1a}$ and R$^{1b}$ are independently selected from hydrogen, methyl, cyclopropyl, or —CHF$_2$. In an embodiment, R$^{1a}$ is hydrogen, and Rib is hydrogen, methyl, cyclopropyl, or —CHF$_2$.

An embodiment of the present invention includes compounds wherein n is 0. In another embodiment, n is 1. In a further embodiment, n is 2. In a still further embodiment, n is 3.

An embodiment of the present invention includes compounds wherein X is hydrogen.

An embodiment of the present invention includes compounds where X is

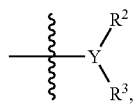

and Y is CH or N. In one embodiment, Y is CH. In another embodiment Y is N.

An of the present invention includes compounds wherein X is

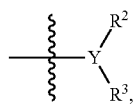

Y is CH, and, R$^2$ and R$^3$ are joined to form a C$_{3-6}$cycloalkyl, unsubstituted or substituted with one or more substituents selected from R$^4$. In one embodiment, R$^2$ and R$^3$ are joined to form a cyclopentyl, unsubstituted or substituted with one or more substituents selected from R$^4$.

An embodiment of the present invention includes compounds where X is

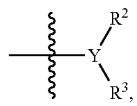

wherein Y is N, and R$^2$ and R$^3$ are independently selected from the group consisting of:

(1) hydrogen,
(2) methyl, which is optionally substituted with one or more halogen, hydroxy, cyclopropyl, phenyl (optionally substituted with $C_{1-6}$alkyl, halogen or —$CF_3$), or a 5- or 6-membered heteroaryl (optionally substituted with $C_{1-6}$ alkyl),
(3) —(C═O)O—$CH_3$,
(4) $C_{3-6}$ cycloalkyl, which is optionally substituted with —$CF_3$,
(5) saturated or partially unsaturated mono- or bicyclic heterocycle comprising up to 8 carbon atoms and from one to three nitrogen atoms, and
(6) a 5- or 6-membered heteroaryl (optionally substituted with $C_{1-6}$ alkyl).

An embodiment of the present invention includes compounds wherein Y is N, and $R^2$ and $R^3$ are independently selected from the group consisting of:
(1) hydrogen,
(2) methyl, which is optionally substituted with one or more fluoro, hydroxy, cyclopropyl, phenyl (optionally substituted with $C_{1-6}$ alkyl, halogen or —$CF_3$), or a 5- or 6-membered heteroaryl (optionally substituted with $C_{1-6}$ alkyl),
(3) —(C═O)O—$CH_3$,
(4) cyclobutyl, which is optionally substituted with —$CF_3$,
(5) saturated or partially unsaturated mono- or bicyclic heterocycle comprising up to 8 carbon atoms and from one to three nitrogen atoms, and
(6) a 5- or 6-membered heteroaryl (optionally substituted with $C_{1-6}$alkyl).

An embodiment of the present invention includes compounds wherein X is

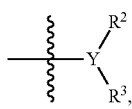

Y is CH or N, and $R^2$ and $R^3$ are joined to form a mono- or bicyclic heterocyclic moiety comprising up to 10 carbon atoms and one or more heteroatoms selected from N, S or O, unsubstituted or substituted on either a carbon or a heteroatom with one or more substituents selected from $R^4$. In one embodiment, the heterocylic moiety comprises from one to four heteroatoms selected from N, S or O. The heterocyclic moiety can be saturated, partially unsaturated or unsaturated. In one embodiment, Y is CH. In another embodiment, Y is N.

An embodiment of the present invention includes compounds where X is

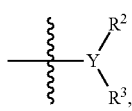

Y is CH or N, and $R^2$ and $R^3$ are joined to form a saturated, unsaturated or partially unsaturated monocyclic heterocyclic moiety comprising up to 6 carbon atoms and one or two heteroatoms selected from N, O or S, which is unsubstituted or substituted with one or more substituents selected from $R^4$.

An embodiment of the present invention includes compounds where X is

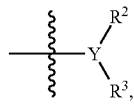

Y is CH or N, and $R^2$ and $R^3$ are joined to form a saturated, unsaturated or partially unsaturated bicyclic heterocyclic moiety comprising up to 10 carbon atoms and from one to four heteroatoms selected from N, S or O, which is unsubstituted or substituted with one or more substituents selected from $R^4$.

An embodiment of the present invention includes compounds where X is

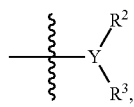

Y is CH or N, and $R^2$ and $R^3$ are joined to form a saturated mono- or bicyclic heterocyclic moiety comprising up to 10 carbon atoms and from one to four heteroatoms selected from N, S or O, which is unsubstituted or substituted with one or more substituents selected from $R^4$. In one embodiment, the saturated heterocyclic moiety is a bicylic moiety. In another embodiment, the saturated heterocyclic moiety is a monocylic moiety comprising up to 6 carbon atoms and one or two heteroatoms selected from N, O or S.

An embodiment of the present invention includes compounds wherein X is

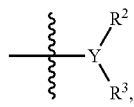

Y is CH or N, and $R^2$ and $R^3$ are joined to form an unsaturated or partially unsaturated mono- or bicyclic heterocyclic moiety comprising up to 10 carbon atoms and from one to four heteroatoms selected from N, S or O, which is unsubstituted or substituted with one or more substituents selected from $R^4$. In one embodiment, the unsaturated or partially unsaturated heterocylic moiety is a bicylic moiety. In another embodiment, the unsaturated or partially unsaturated heterocylic moiety is a monocylic moiety comprising up to 6 carbon atoms and one or two heteroatoms selected from N, O or S.

An embodiment of the present invention includes compounds wherein X is

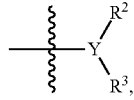

Y is CH or N, and $R^2$ and $R^3$ are joined to form a saturated mono- or bicyclic heterocyclic moiety selected from the group consisting of:

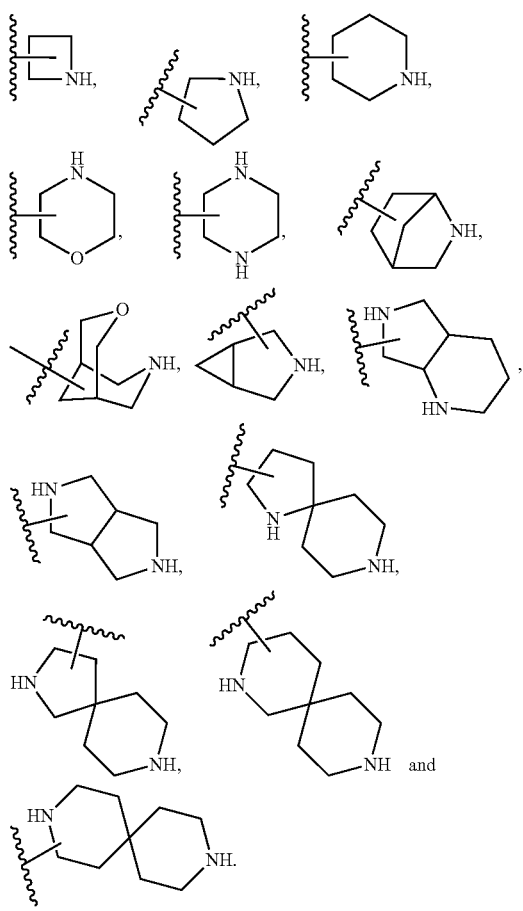

and wherein the saturated heterocyclic moiety is unsubstituted or substituted on either a carbon or a heteroatom with one or more substituents selected from $R^4$. In this embodiment, the attachment of the heterocyclic moiety to the rest of the molecule can occur through either a carbon or a nitrogen atom. Thus, in one embodiment, Y is N, and in another embodiment, Y is CH. In one embodiment, $R^2$ and $R^3$ are joined to form a piperidinyl, which can be unsubstituted or substituted with one or more substituents selected from $R^4$.

An embodiment of the present invention includes compounds wherein X is

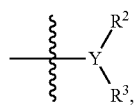

Y is CH or N, and $R^2$ and $R^3$ are joined to form a saturated mono- or bicyclic heterocyclic moiety selected from the group consisting of:

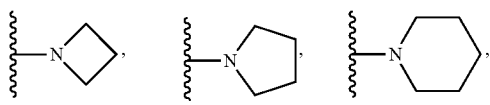

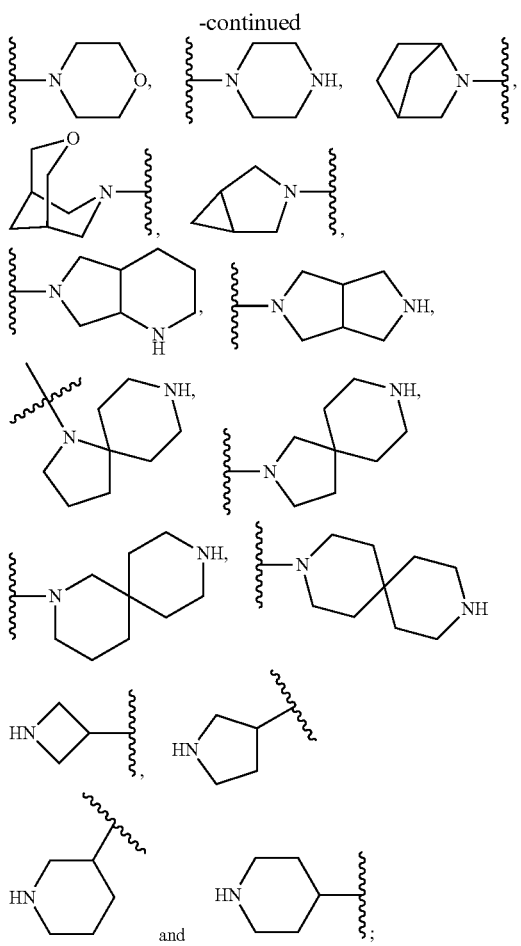

and wherein the saturated heterocyclic moiety is unsubstituted or substituted on either a carbon or a heteroatom with one or more substituents selected from $R^4$.

An embodiment of the present invention includes compounds wherein X is

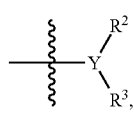

Y is N, and $R^2$ and $R^3$ are joined to form a saturated mono- or bicyclic heterocyclic moiety selected from the group consisting of:

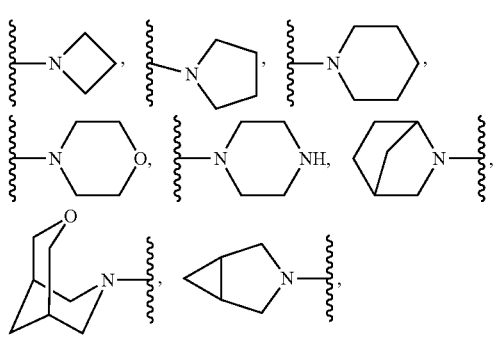

-continued

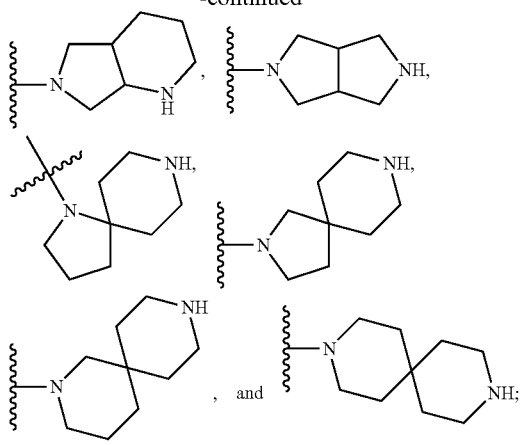

and wherein the saturated heterocyclic moiety is unsubstituted or substituted on either a carbon or a heteroatom with one or more substituents selected from $R^4$.

An embodiment of the present invention includes compounds wherein X is

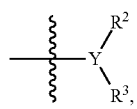

Y is CH, and $R^2$ and $R^3$ are joined to form a saturated heterocyclic moiety selected from the group consisting of:

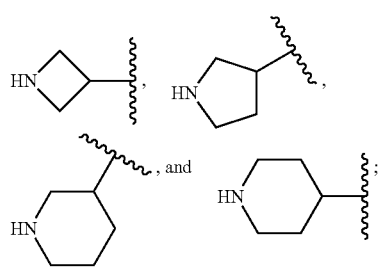

and wherein the saturated heterocyclic moiety is unsubstituted or substituted on either a carbon or a heteroatom with one or more substituents selected from $R^4$.

In one embodiment,

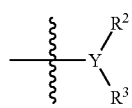

represents

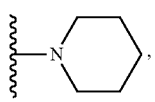

which can be unsubstituted or substituted with one or more substituents selected from $R^4$.

An embodiment of the present invention includes compounds wherein X is

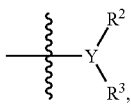

Y is CH or N, and $R^2$ and $R^3$ are joined to form an unsaturated or partially unsaturated mono- or bicyclic heterocyclic moiety selected from the group consisting of:

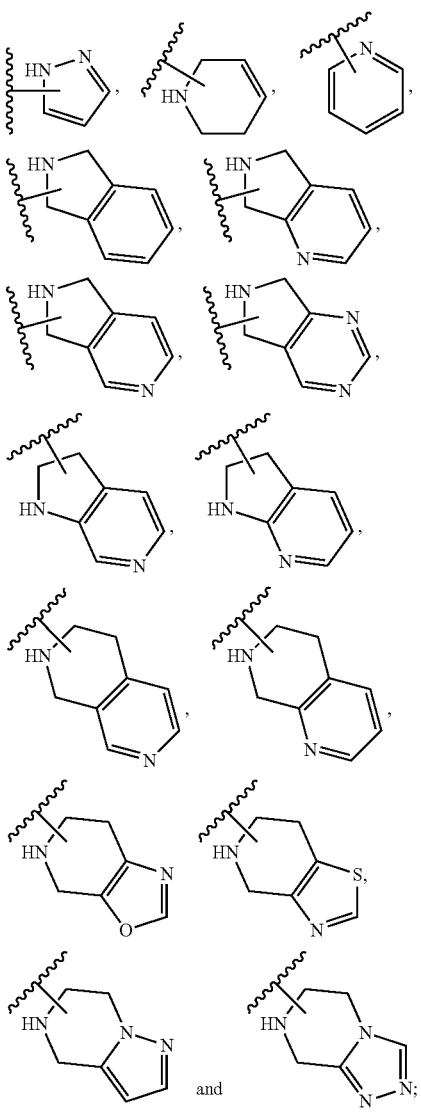

and wherein the unsaturated or partially unsaturated mono- or bicyclic heterocyclic moiety is unsubstituted or substituted on either a carbon or a heteroatom with one or more substituents selected from $R^4$. In this embodiment, the attachment of the heterocyclic moiety to the rest of the molecule can occur through either a carbon or a nitrogen atom. Thus, in one embodiment, Y is N, and in another embodiment, Y is CH.

An embodiment of the present invention includes compounds wherein X is

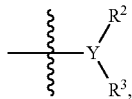

Y is CH or N, and $R^2$ and $R^3$ are joined to form an unsaturated or partially unsaturated mono- or bicyclic heterocyclic moiety selected from the group consisting of:

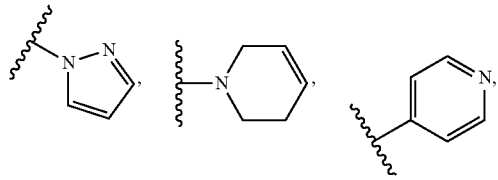

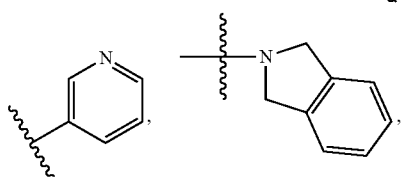

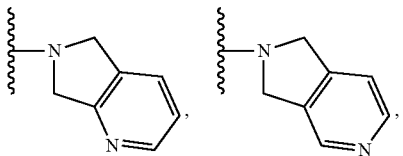

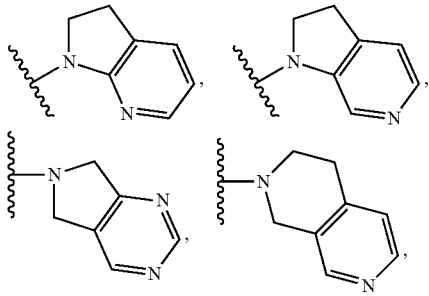

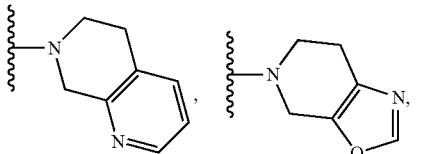

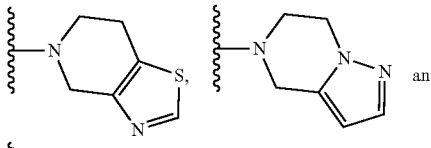

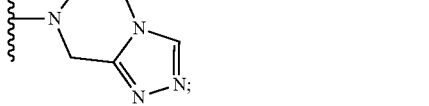

and wherein the heterocyclic moiety is unsubstituted or substituted on either a carbon or a heteroatom with one or more substituents selected from $R^4$.

An embodiment of the present invention includes compounds wherein X is

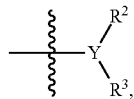

Y is N, and $R^2$ and $R^3$ are joined to form an unsaturated or partially unsaturated mono- or bicyclic heterocyclic moiety selected from the group consisting of:

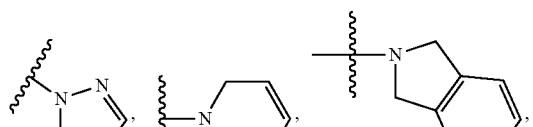

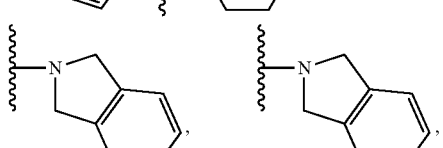

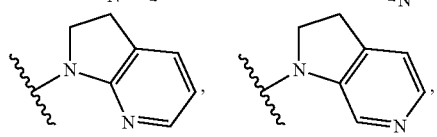

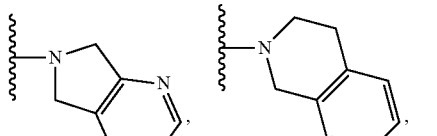

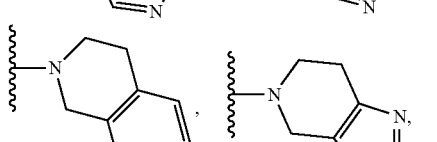

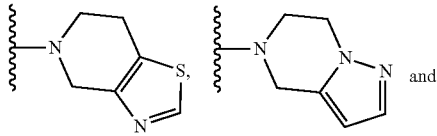

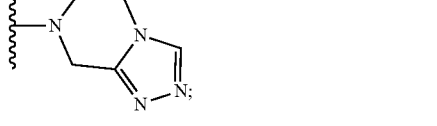

and wherein the heterocyclic moiety is unsubstituted or substituted on either a carbon or a heteroatom with one or more substituents selected from $R^4$.

An embodiment of the present invention includes compounds wherein X is

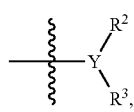

Y is CH, and $R^2$ and $R^3$ are joined to form an unsaturated or partially unsaturated heterocyclic moiety selected from:

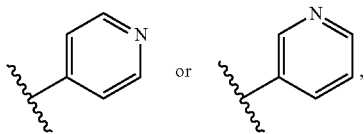 [SMILES: *c1ccncc1 ; *c1cccnc1]

and wherein the heterocyclic moiety is unsubstituted or substituted on either a carbon or a heteroatom with one or more substituents selected from $R^4$.

In one embodiment,

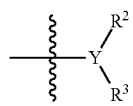

is selected from

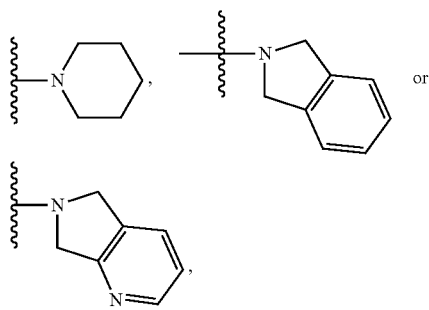

which can be unsubstituted or substituted with one or more substituents selected from $R^4$.

An embodiment of the present invention includes compounds wherein $R^4$ is selected from the group consisting of:
(1) hydroxy,
(2) fluoro,
(3) chloro,
(4) $C_{1-6}$ alkyl, optionally substituted with one or more fluoro, chloro or cyclopropyl,
(5) $C_{3-6}$ cycloalkyl,
(6) —O—$CH_3$,
(7) —$(CH_2)_2OCH_3$,
(8) —$O(CH_2)_2OCH_3$,
(9) oxo,
(10) —O-phenyl, which is optionally substituted with fluoro;
(11) phenyl, which is optionally substituted with fluoro, $C_{1-6}$ alkyl or —O—$C_{1-6}$ alkyl (wherein the $C_{1-6}$ alkyl or —O—$C_{1-6}$ alkyl are substituted with —O—$C_{1-6}$ alkyl), and
(12) heterocycle selected from pyridinyl, pyrimidinyl, thiazoyl, thiadiazolyl or piperidinyl, which is optionally substituted with one or more fluoro, chloro or phenyl (optionally substituted with halogen or $CF_3$).

An embodiment of the present invention includes compounds wherein $R^4$ is selected from the group consisting of:
(1) hydroxy,
(2) fluoro,
(3) chloro,
(4) methyl,
(5) ethyl,
(6) —$(CH_2)_m$—$CHF_2$, where m is 0-3,
(7) —$(CH_2)_m$—$CF_3$, where m is 0-3,
(8) —$(CH_2)_m$-cyclopropyl, where m is 0-3,
(9) cyclobutyl
(10) cyclopentyl,
(11) —O—$CH_3$,
(12) —$(CH_2)_2OCH_3$,
(13) —$O(CH_2)_2OCH_3$,
(14) oxo,
(15) —O-phenyl, which is optionally substituted with one or more fluoro;
(16) phenyl, which is optionally substituted with one or more fluoro or —$O(CH_2)_2OCH_3$, and
(17) heterocycle selected from pyridinyl, pyrimidinyl, thiazoyl, thiadiazolyl or piperidinyl, which is optionally substituted with one or more fluoro, chloro or phenyl (optionally substituted with fluoro or $CF_3$).

In some embodiments, a compound of the invention is one selected from the list below, or a pharmaceutically acceptable salt thereof:

2,2-difluoro-[1,3]dioxolo[4,5-h][1,2,4]triazolo[1,5-c]quinazolin-5-amine;

2,2-difluoro-8-methyl-[1,3]dioxolo[4,5-h][1,2,4]triazolo[1,5-c]quinazolin-5-amine;

8-((2-chloropyridin-3-yl)methyl)-2,2-difluoro-[1,3]dioxolo[4,5-h][1,2,4]triazolo[1,5-c]quinazolin-5-amine;

(S)-2,2-difluoro-8-((2-(3-(4-fluorophenyl)pyrrolidin-1-yl)pyridin-3-yl)methyl)-[1,3]dioxolo[4,5-h][1,2,4]triazolo[1,5-c]quinazolin-5-amine;

(S)-2,2-difluoro-8-((2-(3-(4-(trifluoromethyl)phenyl)pyrrolidin-1-yl)pyridin-3-yl)methyl)-[1,3]dioxolo[4,5-h][1,2,4]triazolo[1,5-c]quinazolin-5-amine;

(8-(2-(5H-pyrrolo[3,4-b]pyridin-6(7H)-yl)ethyl)-2,2-difluoro-[1,3]dioxolo[4,5-h][1,2,4]triazolo[1,5-c]quinazolin-5-amine;

2,2-difluoro-8-{2-[5-(trifluoromethyl)-1,3-dihydro-2H-isoindol-2-yl]ethyl}[1,3]dioxolo[4,5-h][1,2,4]triazolo[1,5-c]quinazolin-5-amine;

2,2-difluoro-8-[2-(5-fluoro-1,3-dihydro-2H-isoindol-2-yl)ethyl][1,3]dioxolo[4,5-h][1,2,4]triazolo[1,5-c]quinazolin-5-amine;

2,2-difluoro-8-{2-[2-(trifluoromethyl)-5,7-dihydro-6H-pyrrolo[3,4-d]pyrimidin-6-yl]ethyl}[1,3]dioxolo[4,5-h][1,2,4]triazolo[1,5-c]quinazolin-5-amine;

8-[2-(3-ethyl-5,6-dihydro[1,2,4]triazolo[4,3-a]pyrazin-7(8H)-yl)ethyl]-2,2-difluoro[1,3]dioxolo[4,5-h][1,2,4]triazolo[1,5-c]quinazolin-5-amine;

8-[2-(1,3-dihydro-2H-pyrrolo[3,4-c]pyridin-2-yl)ethyl]-2,2-difluoro[1,3]dioxolo[4,5-h][1,2,4]triazolo[1,5-c]quinazolin-5-amine;

2,2-difluoro-8-[2-(2-methyl-6,7-dihydro[1,3]oxazolo[5,4-c]pyridin-5(4H)-yl)ethyl][1,3]dioxolo[4,5-h][1,2,4]triazolo[1,5-c]quinazolin-5-amine;

2,2-difluoro-8-[2-(2-methyl-6,7-dihydro[1,3]thiazolo[4,5-c]pyridin-5(4H)-yl)ethyl][1,3]dioxolo[4,5-h][1,2,4]triazolo[1,5-c]quinazolin-5-amine;

8-[2-(2-cyclopropyl-6,7-dihydro[1,3]oxazolo[5,4-c]pyridin-5(4H)-yl)ethyl]-2,2-difluoro[1,3]dioxolo[4,5-h][1,2,4]triazolo[1,5-c]quinazolin-5-amine;

2,2-difluoro-8-[2-(3-fluoroazetidin-1-yl)ethyl][1,3]dioxolo[4,5-h][1,2,4]triazolo[1,5-c]quinazolin-5-amine;

8-[2-(3-ethyl-3-fluoroazetidin-1-yl)ethyl]-2,2-difluoro[1,3]dioxolo[4,5-h][1,2,4]triazolo[1,5-c]quinazolin-5-amine;

8-[2-(3-cyclopropyl-3-fluoroazetidin-1-yl)ethyl]-2,2-difluoro[1,3]dioxolo[4,5-h][1,2,4]triazolo[1,5-c]quinazolin-5-amine;

8-[2-(3,3-difluoroazetidin-1-yl)ethyl]-2,2-difluoro[1,3]dioxolo[4,5-h][1,2,4]triazolo[1,5-c]quinazolin-5-amine;

1-[2-(5-amino-2,2-difluoro[1,3]dioxolo[4,5-h][1,2,4]triazolo[1,5-c]quinazolin-8-yl)ethyl]-3-(trifluoromethyl)azetidin-3-ol;

2,2-difluoro-8-{2-[3-fluoro-3-(trifluoromethyl)azetidin-1-yl]ethyl}[1,3]dioxolo[4,5-h][1,2,4]triazolo[1,5-c]quinazolin-5-amine;

2,2-difluoro-8-{2-[(2R,4S)-4-fluoro-2-methylpyrrolidin-1-yl]ethyl}[1,3]dioxolo[4,5-h][1,2,4]triazolo[1,5-c]quinazolin-5-amine;

8-{2-[(3S,4S)-3,4-difluoropyrrolidin-1-yl]ethyl}-2,2-difluoro[1,3]dioxolo[4,5-h][1,2,4]triazolo[1,5-c]quinazolin-5-amine;

8-[2-(3,3-difluoropyrrolidin-1-yl)ethyl]-2,2-difluoro[1,3]dioxolo[4,5-h][1,2,4]triazolo[1,5-c]quinazolin-5-amine;

8-{2-[(2R)-4,4-difluoro-2-methylpyrrolidin-1-yl]ethyl}-2,2-difluoro[1,3]dioxolo[4,5-h][1,2,4]triazolo[1,5-c]quinazolin-5-amine;

8-{2-[(2S)-4,4-difluoro-2-methylpyrrolidin-1-yl]ethyl}-2,2-difluoro[1,3]dioxolo[4,5-h][1,2,4]triazolo[1,5-c]quinazolin-5-amine;

2,2-difluoro-8-[2-(4-fluoropiperidin-1-yl)ethyl][1,3]dioxolo[4,5-h][1,2,4]triazolo[1,5-c]quinazolin-5-amine;

2,2-difluoro-8-[2-(4-fluoro-4-methylpiperidin-1-yl)ethyl][1,3]dioxolo[4,5-h][1,2,4]triazolo[1,5-c]quinazolin-5-amine;

8-[2-(3,3-difluoropiperidin-1-yl)ethyl]-2,2-difluoro[1,3]dioxolo[4,5-h][1,2,4]triazolo[1,5-c]quinazolin-5-amine;

8-[2-(4,4-difluoropiperidin-1-yl)ethyl]-2,2-difluoro[1,3]dioxolo[4,5-h][1,2,4]triazolo[1,5-c]quinazolin-5-amine;

8-{2-[(2R)-4,4-difluoro-2-methylpiperidin-1-yl]ethyl}-2,2-difluoro[1,3]dioxolo[4,5-h][1,2,4]triazolo[1,5-c]quinazolin-5-amine;

8-[2-(9,9-difluoro-3-oxa-7-azabicyclo[3.3.1]non-7-yl)ethyl]-2,2-difluoro[1,3]dioxolo[4,5-h][1,2,4]triazolo[1,5-c]quinazolin-5-amine;

8-[2-(3,3-dimethylazetidin-1-yl)ethyl]-2,2-difluoro[1,3]dioxolo[4,5-h][1,2,4]triazolo[1,5-c]quinazolin-5-amine;

8-{2-[(2R,5R)-2,5-dimethylpyrrolidin-1-yl]ethyl}-2,2-difluoro[1,3]dioxolo[4,5-h][1,2,4]triazolo[1,5-c]quinazolin-5-amine;

8-[2-(3-azabicyclo[3.1.0]hex-3-yl)ethyl]-2,2-difluoro[1,3]dioxolo[4,5-h][1,2,4]triazolo[1,5-c]quinazolin-5-amine;

2,2-difluoro-8-{2-[(3 S)-3-phenylpyrrolidin-1-yl]ethyl}[1,3]dioxolo[4,5-h][1,2,4]triazolo[1,5-c]quinazolin-5-amine;

2,2-difluoro-8-{2-[(3R)-3-phenylpyrrolidin-1-yl]ethyl}[1,3]dioxolo[4,5-h][1,2,4]triazolo[1,5-c]quinazolin-5-amine;

2,2-difluoro-8-[2-(4-methylpiperidin-1-yl)ethyl][1,3]dioxolo[4,5-h][1,2,4]triazolo[1,5-c]quinazolin-5-amine;

8-[2-(3, 3-dimethylpiperidin-1-yl)ethyl]-2,2-difluoro[1,3]dioxolo[4,5-h][1,2,4]triazolo[1,5-c]quinazolin-5-amine;

2,2-difluoro-8-{2-[(3R)-3-methoxypiperidin-1-yl]ethyl}[1,3]dioxolo[4,5-h][1,2,4]triazolo[1,5-c]quinazolin-5-amine;

2,2-difluoro-8-[2-(4-methyl-3,6-dihydropyridin-1(2H)-yl)ethyl][1,3]dioxolo[4,5-h][1,2,4]triazolo[1,5-c]quinazolin-5-amine;

2,2-difluoro-8-{2-[(2R)-2-methylmorpholin-4-yl]ethyl}[1,3]dioxolo[4,5-h][1,2,4]triazolo[1,5-c]quinazolin-5-amine;

2,2-difluoro-8-{2-[(3S)-3-methylmorpholin-4-yl]ethyl}[1,3]dioxolo[4,5-h][1,2,4]triazolo[1,5-c]quinazolin-5-amine;

8-{2-[(2R,6S)-2,6-dimethylmorpholin-4-yl]ethyl}-2,2-difluoro[1,3]dioxolo[4,5-h][1,2,4]triazolo[1,5-c]quinazolin-5-amine;

2,2-difluoro-8-{2-[(2R)-2-methyl-4-(2-methyl-1,3-thiazol-5-yl)piperazin-1-yl]ethyl}[1,3]dioxolo[4,5-h][1,2,4]triazolo[1,5-c]quinazolin-5-amine;

8-{2-[(2R)-4-(4-chloro-1,2,5-thiadiazol-3-yl)-2-methylpiperazin-1-yl]ethyl}-2,2-difluoro[1,3]dioxolo[4,5-h][1,2,4]triazolo[1,5-c]quinazolin-5-amine;

4-[2-(5-amino-2,2-difluoro[1,3]dioxolo[4,5-h][1,2,4]triazolo[1,5-c]quinazolin-8-yl)ethyl]-1-methylpiperazin-2-one;

4-[2-(5-amino-2,2-difluoro[1,3]dioxolo[4,5-h][1,2,4]triazolo[1,5-c]quinazolin-8-yl)ethyl]-1-(cyclopropylmethyl)piperazin-2-one;

4-[2-(5-amino-2,2-difluoro[1,3]dioxolo[4,5-h][1,2,4]triazolo[1,5-c]quinazolin-8-yl)ethyl]-1-cyclopentylpiperazin-2-one;

4-[2-(5-amino-2,2-difluoro[1,3]dioxolo[4,5-h][1,2,4]triazolo[1,5-c]quinazolin-8-yl)ethyl]-1-(3-fluorophenyl)piperazin-2-one;

2,2-difluoro-8-{2-[(4aR,7aR)-octahydro-6H-pyrrolo[3,4-b]pyridin-6-yl]ethyl}[1,3]dioxolo[4,5-h][1,2,4]triazolo[1,5-c]quinazolin-5-amine;

2,2-difluoro-8-{2-[(3aS)-hexahydropyrrolo[3,4-c]pyrrol-2(1H)-yl]ethyl}[1,3]dioxolo[4,5-h][1,2,4]triazolo[1,5-c]quinazolin-5-amine;

8-[2-(2,8-diazaspiro[4.5]dec-2-yl)ethyl]-2,2-difluoro[1,3]dioxolo[4,5-h][1,2,4]triazolo[1,5-c]quinazolin-5-amine;

8-[2-(3,9-diazaspiro[5.5]undec-3-yl)ethyl]-2,2-difluoro[1,3]dioxolo[4,5-h][1,2,4]triazolo[1,5-c]quinazolin-5-amine;

8-[2-(1,8-diazaspiro[4.5]dec-1-yl)ethyl]-2,2-difluoro[1,3]dioxolo[4,5-h][1,2,4]triazolo[1,5-c]quinazolin-5-amine;

8-[2-(2,9-diazaspiro[5.5]undec-2-yl)ethyl]-2,2-difluoro[1,3]dioxolo[4,5-h][1,2,4]triazolo[1,5-c]quinazolin-5-amine;

8-[2-(2-azaspiro[3.3]hept-6-ylamino)ethyl]-2,2-difluoro[1,3]dioxolo[4,5-h][1,2,4]triazolo[1,5-c]quinazolin-5-amine;

2,2-difluoro-8-(2-{[1-(trifluoromethyl)cyclobutyl]amino}ethyl)[1,3]dioxolo[4,5-h][1,2,4]triazolo[1,5-c]quinazolin-5-amine;

2,2-difluoro-8-(2-{[4-(trifluoromethyl)benzyl]amino}ethyl)[1,3]dioxolo[4,5-h][1,2,4]triazolo[1,5-c]quinazolin-5-amine;

8-(2-{(cyclopropylmethyl) [(4-methyl-1,3-thiazol-2-yl)methyl]amino}ethyl)-2,2-difluoro[1,3]dioxolo[4,5-h][1,2,4]triazolo[1,5-c]quinazolin-5-amine;

8-(2-{(cyclopropylmethyl) [(2-methyl-1,3-thiazol-5-yl)methyl]amino}ethyl)-2,2-difluoro[1,3]dioxolo[4,5-h][1,2,4]triazolo[1,5-c]quinazolin-5-amine;

2,2-difluoro-8-{2-[3-(trifluoromethyl)piperidin-1-yl]ethyl}[1,3]dioxolo[4,5-h][1,2,4]triazolo[1,5-c]quinazolin-5-amine;

8-{2-[(2R,6R)-2,6-dimethylmorpholin-4-yl]ethyl}-2,2-difluoro[1,3]dioxolo[4,5-h][1,2,4]triazolo[1,5-c]quinazolin-5-amine;

2,2-difluoro-8-[2-(3-fluoro-3-methylpiperidin-1-yl)ethyl][1,3]dioxolo[4,5-h][1,2,4]triazolo[1,5-c]quinazolin-5-amine;

8-[2-(6,6-difluoro-2-azabicyclo[2.2.1]hept-2-yl)ethyl]-2,2-difluoro[1,3]dioxolo[4,5-h][1,2,4]triazolo[1,5-c]quinazolin-5-amine;

8-[2-(3,3-difluoro-2-methylpiperidin-1-yl)ethyl]-2,2-difluoro[1,3]dioxolo[4,5-h][1,2,4]triazolo[1,5-c]quinazolin-5-amine;

1-(2-(5-amino-2,2-difluoro-[1,3]dioxolo[4,5-h][1,2,4]triazolo[1,5-c]quinazolin-8-yl)ethyl)-3-(trifluoromethyl)piperidin-3-ol;

2,2-difluoro-8-(2-(3-fluoro-3-(trifluoromethyl)piperidin-1-yl)ethyl)-[1,3]dioxolo[4,5-h][1,2,4]triazolo[1,5-c]quinazolin-5-amine;

(R)-8-(2-(1H-pyrrolo[3,4-c]pyridin-2(3H)-yl)propyl)-2,2-difluoro-[1,3]dioxolo[4,5-h][1,2,4]triazolo[1,5-c]quinazolin-5-amine;

8-[(2R)-2-(2,3-dihydro-1H-pyrrolo[2,3-b]pyridin-1-yl)propyl]-2,2-difluoro[1,3]dioxolo[4,5-h][1,2,4]triazolo[1,5-c]quinazolin-5-amine;

8-[(2R)-2-(2,3-dihydro-1H-pyrrolo[2,3-c]pyridin-1-yl)propyl]-2,2-difluoro[1,3]dioxolo[4,5-h][1,2,4]triazolo[1,5-c]quinazolin-5-amine;

8-[(2R)-2-(3,4-dihydro-2,7-naphthyridin-2(1H)-yl)propyl]-2,2-difluoro[1,3]dioxolo[4,5-h][1,2,4]triazolo[1,5-c]quinazolin-5-amine;

8-[(2R)-2-(5,8-dihydro-1,7-naphthyridin-7(6H)-yl)propyl]-2,2-difluoro[1,3]dioxolo[4,5-h][1,2,4]triazolo[1,5-c]quinazolin-5-amine;

2,2-difluoro-8-[(2R)-2-(2-methyl-6,7-dihydro[1,3]oxazolo[5,4-c]pyridine-5(4H)-yl)propyl][1,3]dioxolo[4,5-h][1,2,4]triazolo[1,5-c]quinazolin-5-amine;

2,2-difluoro-8-[(2R)-2-(2-methyl-6,7-dihydro[1,3]thiazolo[5,4-c]pyridin-5 (4H)-yl)propyl][1,3]dioxolo[4,5-h][1,2,4]triazolo[1,5-c]quinazolin-5-amine;

8-[(2R)-2-(2-cyclopropyl-6,7-dihydro[1,3]oxazolo[5,4-c]pyridin-5(4H)-yl)propyl]-2,2-difluoro[1,3]dioxolo[4,5-h][1,2,4]triazolo[1,5-c]quinazolin-5-amine;

2,2-difluoro-8-[(2R)-2-(2-methyl-6,7-dihydro[1,3]thiazolo[4,5-c]pyridin-5(4H)-yl)propyl][1,3]dioxolo[4,5-h][1,2,4]triazolo[1,5-c]quinazolin-5-amine;

2,2-difluoro-8-[(2R)-2-(2-methyl-6,7-dihydropyrazolo[1,5-a]pyrazin-5 (4H)-yl)propyl][1,3]dioxolo[4,5-h][1,2,4]triazolo[1,5-c]quinazolin-5-amine;

2,2-difluoro-8-[(2R)-2-(3-fluoro-3-methylazetidin-1-yl)propyl][1,3]dioxolo[4,5-h][1,2,4]triazolo[1,5-c]quinazolin-5-amine;

2,2-difluoro-8-{(2R)-2-[3-fluoro-3-methylpiperidin-1-yl]propyl}[1,3]dioxolo[4,5-h][1,2,4]triazolo[1,5-c]quinazolin-5-amine;

(S)-8-(2-(1H-pyrrolo[3,4-c]pyridin-2(3H)-yl)propyl)-2,2-difluoro-[1,3]dioxolo[4,5-h][1,2,4]triazolo[1,5-c]quinazolin-5-amine;

2,2-difluoro-8-[(2S)-2-(3-fluoro-3-methylazetidin-1-yl)propyl][1,3]dioxolo[4,5-h][1,2,4]triazolo[1,5-c]quinazolin-5-amine;

2,2-difluoro-8-{(2S)-2-[3-fluoro-3-methylpiperidin-1-yl]propyl}[1,3]dioxolo[4,5-h][1,2,4]triazolo[1,5-c]quinazolin-5-amine;

8-[2-(5,7-dihydro-6H-pyrrolo[3,4-b]pyridin-6-yl)propyl]-2,2-difluoro[1,3]dioxolo[4,5-h][1,2,4]triazolo[1,5-c]quinazolin-5-amine;

8-[2-(3,3-difluoroazetidin-1-yl)propyl]-2,2-difluoro[1,3]dioxolo[4,5-h][1,2,4]triazolo[1,5-c]quinazolin-5-amine;

8-[2-(3,3-difluoropiperidin-1-yl)propyl]-2,2-difluoro[1,3]dioxolo[4,5-h][1,2,4]triazolo[1,5-c]quinazolin-5-amine;

8-(3,3-difluoro-2-(5H-pyrrolo[3,4-b]pyridin-6(7H)-yl)propyl)-2,2-difluoro-[1,3]dioxolo[4,5-h][1,2,4]triazolo[1,5-c]quinazolin-5-amine;

8-(2-(1H-pyrazol-1-yl)ethyl)-2,2-difluoro-[1,3]dioxolo[4,5-h][1,2,4]triazolo[1,5-c]quinazolin-5-amine;

6-(2-(5-amino-2,2-difluoro-[1,3]dioxolo[4,5-h][1,2,4]triazolo[1,5-c]quinazolin-8-yl)ethyl)-6,7-dihydro-5H-pyrrolo[3,4-b]pyridin-5-one;

2,2-difluoro-8-(2-(3-fluoroazetidin-1-yl)-2-methylpropyl)-[1,3]dioxolo[4,5-h][1,2,4]triazolo[1,5-c]quinazolin-5-amine;

2,2-difluoro-8-((7-(4-fluorophenyl)-4,7-diazaspiro[2.5]octan-4-yl)methyl)-[1,3]dioxolo[4,5-h][1,2,4]triazolo[1,5-c]quinazolin-5-amine;

2,2-difluoro-8-{[7-(5-fluoropyridin-2-yl)-4,7-diazaspiro[2.5]oct-4-yl]methyl}[1,3]dioxolo[4,5-h][1,2,4]triazolo[1,5-c]quinazolin-5-amine;

2,2-difluoro-8-{[7-(3-fluorophenyl)-4,7-diazaspiro[2.5]oct-4-yl]methyl}[1,3]dioxolo[4,5-h][1,2,4]triazolo[1,5-c]quinazolin-5-amine;

2,2-difluoro-8-({7-[4-(2-methoxyethoxy)phenyl]-4,7-diazaspiro[2.5]oct-4-yl}methyl)[1,3]dioxolo[4,5-h][1,2,4]triazolo[1,5-c]quinazolin-5-amine;

2,2-difluoro-8-{[(2R)-4-(4-fluorophenyl)-2-methylpiperazin-1-yl]methyl}[1,3]dioxolo[4,5-h][1,2,4]triazolo[1,5-c]quinazolin-5-amine;

2,2-difluoro-8-{[(2R)-2-methyl-4-(methyl-1,3-thiazol-5-yl)piperazin-1-yl]methyl}[1,3]dioxolo[4,5-h][1,2,4]triazolo[1,5-c]quinazolin-5-amine;

8-{[(2R)-4-(4-chloro-1,2,5-thiadiazol-3-yl)-2-methylpiperazin-1-yl]methyl}-2,2-difluoro[1,3]dioxolo[4,5-h][1,2,4]triazolo[1,5-c]quinazolin-5-amine;

8-((3,3-difluoroazetidin-1-yl)methyl)-2,2-difluoro-[1,3]dioxolo[4,5-h][1,2,4]triazolo[1,5-c]quinazolin-5-amine;

8-[(3,3-dimethylazetidin-1-yl)methyl]-2,2-difluoro[1,3]dioxolo[4,5-h][1,2,4]triazolo[1,5-c]quinazolin-5-amine;

2,2-difluoro-8-[(3-fluoro-3-methylazetidin-1-yl)methyl][1,3]dioxolo[4,5-h][1,2,4]triazolo[1,5-c]quinazolin-5-amine;

8-[(3-ethyl-3-fluoroazetidin-1-yl)methyl]-2,2-difluoro[1,3]dioxolo[4,5-h][1,2,4]triazolo[1,5-c]quinazolin-5-amine;

11-[(5-amino-2,2-difluoro[1,3]dioxolo[4,5-h][1,2,4]triazolo[1,5-c]quinazolin-8-yl)methyl]-3-(trifluoromethyl)azetidin-3-ol;

2,2-difluoro-8-{[3-fluoro-3-(trifluoromethyl)azetidin-1-yl]methyl}[1,3]dioxolo[4,5-h][1,2,4]triazolo[1,5-c]quinazolin-5-amine;

8-{[(3S,4S)-3,4-difluoropyrrolidin-1-yl]methyl}-2,2-difluoro[1,3]dioxolo[4,5-h][1,2,4]triazolo[1,5-c]quinazolin-5-amine;

8-[(3,3-difluoropyrrolidin-1-yl)methyl]-2,2-difluoro[1,3]dioxolo[4,5-h][1,2,4]triazolo[1,5-c]quinazolin-5-amine;

2,2-difluoro-8-{[4-(4-fluorophenoxy) piperidin-1-yl]methyl}[1,3]dioxolo[4,5-h][1,2,4]triazolo[1,5-c]quinazolin-5-amine;

8-[(3,3-difluoropiperidin-1-yl)methyl]-2,2-difluoro[1,3]dioxolo[4,5-h][1,2,4]triazolo[1,5-c]quinazolin-5-amine;

8-[(4,4-difluoropiperidin-1-yl)methyl]-2,2-difluoro[1,3]dioxolo[4,5-h][1,2,4]triazolo[1,5-c]quinazolin-5-amine;

2,2-difluoro-8-[(5-fluoro-1,3-dihydro-2H-isoindol-2-yl)methyl][1,3]dioxolo[4,5-h][1,2,4]triazolo[1,5-c]quinazolin-5-amine;

2,2-difluoro-8-{[2-(trifluoromethyl)-5,7-dihydro-6H-pyrrolo[3,4-d]pyrimidin-6-yl]methyl}[1,3]dioxolo[4,5-h][1,2,4]triazolo[1,5-c]quinazolin-5-amine;

8-[(3-ethyl-5,6-dihydro[1,2,4]triazolo[4,3-a]pyrazin-7(8H)-yl)methyl]-2,2-difluoro[1,3]dioxolo[4,5-h][1,2,4]triazolo[1,5-c]quinazolin-5-amine;

2,2-difluoro-8-{[5-(trifluoromethyl)-1,3-dihydro-2H-isoindol-2-yl]methyl}[1,3]dioxolo[4,5-h][1,2,4]triazolo[1,5-c]quinazolin-5-amine;

2,2-difluoro-8-({[4-(trifluoromethyl)benzyl]amino}methyl)[1,3]dioxolo[4,5-h][1,2,4]triazolo[1,5-c]quinazolin-5-amine;

2,2-difluoro-8-({[1-(trifluoromethyl)cyclobutyl]amino}methyl)[1,3]dioxolo[4,5-h][1,2,4]triazolo[1,5-c]quinazolin-5-amine;

8-[(dimethylamino)methyl]-2,2-difluoro[1,3]dioxolo[4,5-h][1,2,4]triazolo[1,5-c]quinazolin-5-amine;
8-({(cyclopropylmethyl)[(4-methyl-1,3-thiazol-2-yl)methyl]amino}methyl)-2,2-difluoro[1,3]dioxolo[4,5-h][1,2,4]triazolo[1,5-c]quinazolin-5-amine;
8-((1H-pyrazol-1-yl)methyl)-2,2-difluoro-[1,3]dioxolo[4,5-h][1,2,4]triazolo[1,5-c]quinazolin-5-amine;
8-[(3,5-dimethyl-1H-pyrazol-1-yl)methyl]-2,2-difluoro[1,3]dioxolo[4,5-h][1,2,4]triazolo[1,5-c]quinazolin-5-amine;
8-{[3,5-bis(trifluoromethyl)-1H-pyrazol-1-yl]methyl}-2,2-difluoro[1,3]dioxolo[4,5-h][1,2,4]triazolo[1,5-c]quinazolin-5-amine;
8-[1-(3,3-difluoroazetidin-1-yl)ethyl]-2,2-difluoro[1,3]dioxolo[4,5-h][1,2,4]triazolo[1,5-c]quinazolin-5-amine;
8-{1-[(3S,4S)-3,4-difluoropyrrolidin-1-yl]ethyl}-2,2-difluoro[1,3]dioxolo[4,5-h][1,2,4]triazolo[1,5-c]quinazolin-5-amine;
8-[1-(3,3-difluoropiperidin-1-yl)ethyl]-2,2-difluoro[1,3]dioxolo[4,5-h][1,2,4]triazolo[1,5-c]quinazolin-5-amine;
8-(3-(5H-pyrrolo[3,4-b]pyridin-6(7H)-yl)propyl)-2,2-difluoro-[1,3]dioxolo[4,5-h][1,2,4]triazolo[1,5-c]quinazolin-5-amine;
(R)-2,2-difluoro-8-(1-(2,2,2-trifluoroethyl)piperidin-3-yl)-[1,3]dioxolo[4,5-h][1,2,4]triazolo[1,5-c]quinazolin-5-amine;
(R)-8-(1-(2,2-difluoroethyl)piperidin-3-yl)-2,2-difluoro-[1,3]dioxolo[4,5-h][1,2,4]triazolo[1,5-c]quinazolin-5-amine;
2,2-difluoro-8-(1-(3,3,3-trifluoropropyl)piperidin-3-yl)-[1,3]dioxolo[4,5-h][1,2,4]triazolo[1,5-c]quinazolin-5-amine;
2,2-difluoro-8-[1-(3-fluorophenyl)piperidin-3-yl][1,3]dioxolo[4,5-h][1,2,4]triazolo[1,5-c]quinazolin-5-amine;
8-[1-(3,5-difluorophenyl) piperidin-3-yl]-2,2-difluoro[1,3]dioxolo[4,5-h][1,2,4]triazolo[1,5-c]quinazolin-5-amine;
2,2-difluoro-8-(1-pyrimidin-5-ylpiperidin-3-yl)[1,3]dioxolo[4,5-h][1,2,4]triazolo[1,5-c]quinazolin-5-amine;
dimethyl[(5-amino-2,2-difluoro[1,3]dioxolo[4,5-h][1,2,4]triazolo[1,5-c]quinazolin-8-yl)methyl]propanedioate;
2-[(5-amino-2,2-difluoro[1,3]dioxolo[4,5-h][1,2,4]triazolo[1,5-c]quinazolin-8-yl)methyl]propane-1,3-diol;
8-[3-chloro-2-(chloromethyl)propyl]-2,2-difluoro[1,3]dioxolo[4,5-h][1,2,4]triazolo[1,5-c]quinazolin-5-amine;
8-[(1-cyclobutylazetidin-3-yl)methyl]-2,2-difluoro[1,3]dioxolo[4,5-h][1,2,4]triazolo[1,5-c]quinazolin-5-amine;
8-{[1-(2,2-difluoropropyl)azetidin-3-yl]methyl}-2,2-difluoro[1,3]dioxolo[4,5-h][1,2,4]triazolo[1,5-c]quinazolin-5-amine;
2,2-difluoro-8-[(1-pyridin-2-ylazetidin-3-yl)methyl][1,3]dioxolo[4,5-h][1,2,4]triazolo[1,5-c]quinazolin-5-amine;
2,2-difluoro-8-{[1-(3,3,3-trifluoropropyl)pyrrolidin-3-yl]methyl}[1,3]dioxolo[4,5-h][1,2,4]triazolo[1,5-c]quinazolin-5-amine;
8-{[1-(2,2-difluoroethyl)pyrrolidin-3-yl]methyl}-2,2-difluoro[1,3]dioxolo[4,5-h][1,2,4]triazolo[1,5-c]quinazolin-5-amine;
2,2-difluoro-8-{[1-(2-methoxyethyl)pyrrolidin-3-yl]methyl}[1,3]dioxolo[4,5-h][1,2,4]triazolo[1,5-c]quinazolin-5-amine;
8-[(2S)-2-amino-2-cyclopropylethyl]-2,2-difluoro[1,3]dioxolo[4,5-h][1,2,4]triazolo[1,5-c]quinazolin-5-amine;
8-[(2R)-2-amino-2-cyclopropylethyl]-2,2-difluoro[1,3]dioxolo[4,5-h][1,2,4]triazolo[1,5-c]quinazolin-5-amine;
8-[(1S,3S)-3-(3,3-difluoropiperidin-1-yl)cyclopentyl]-2,2-difluoro[1,3]dioxolo[4,5-h][1,2,4]triazolo[1,5-c]quinazolin-5-amine; or,
8-[(1S,3R)-3-(3,3-difluoropiperidin-1-yl)cyclopentyl]-2,2-difluoro[1,3]dioxolo[4,5-h][1,2,4]triazolo[1,5-c]quinazolin-5-amine.

Certain embodiments of the present invention include a compound that is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present, depending upon the nature of the various substituents on the molecule. Each such asymmetric center will independently produce two optical isomers, and it is intended that all of the possible optical isomers and diastereomers in mixtures and as pure or partially purified compounds are included within the ambit of this invention. The present invention is meant to comprehend all such isomeric forms of these compounds. For example, formula I shows the structure of the class of compounds without specific stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

The present invention also includes all pharmaceutically acceptable isotopic variations of a compound of formula I in which one or more atoms is replaced by atoms having the same atomic number but an atomic mass or mass number different from the atomic mass or mass number usually found in nature. Examples of isotopes suitable for inclusion in the compounds of the invention include isotopes of hydrogen (such as $^{2}H$ and $^{3}H$), carbon (such as $^{11}C$, $^{13}C$ and $^{14}C$), nitrogen (such as $^{13}N$ and $^{15}N$), oxygen (such as $^{15}O$, $^{17}O$ and $^{18}O$), phosphorus (such as $^{32}P$), sulfur (such as $^{35}S$), fluorine (such as $^{18}F$), iodine (such as $^{123}I$ and $^{125}I$) and chlorine (such as $^{36}Cl$). Certain isotopically-labelled compounds of Formula I, for example those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labelled compounds of Formula I can generally be prepared by conventional techniques known to those skilled in the art or by processes analogous to those described in the accompanying Examples using appropriate isotopically-labelled reagents in place of the non-labeled reagent previously employed.

The term "substituted" means that one or more of the enumerated substituents can occupy one or more of the bonding positions on the substrate typically occupied by "—H", provided that such substitution does not exceed the normal valency rules for the atom in the bonding configuration present in the substrate, and that the substitution ultimate provides a stable compound, e.g., mutually reactive substituents are not present geminal or vicinal to each other, and wherein such a compound is sufficiently robust to survive isolation to a useful degree of purity from a reaction mixture. When the text indicates optional substitution of a moiety (e.g., "optionally substituted"), the term means that, if present, one or more of the enumerated substituents can be present on the substrate in a bonding position normally occupied by a hydrogen atom. A group that is designated as being independently substituted with substituents may be independently substituted with multiple numbers of such substituents.

Bonding sequence is indicated by hyphens where moieties are represented in text, for example, "alkyl" indicates a single bond between a substrate and an alkyl moiety, and "-alkyl-X" indicates that an alkyl group bonds an "X" substituent to a substrate. In structural representation, bonding sequence is indicated by a wavy line terminating a bond representation, for example:

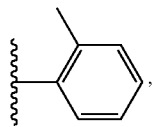

indicates that the methylphenyl moiety is bonded to a substrate through a carbon atom ortho to the methyl substituent, while a bond representation terminated with a wavy line and drawn into a structure without any particular indication of an atom to which it is bonded indicates that the moiety may be bonded to a substrate via any of the atoms in the moiety which are available for bonding. For example:

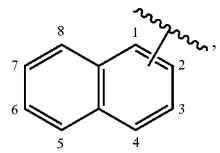

indicates that the naphthalene moiety may be bonded to the substrate through any of carbons 1 to 8. Where substituents are presented in text, unless defined differently at the point of use, bonding arrangement is indicated with hyphens (indicating single bonds), equal signs (indicating double bonds) and parentheses (indicating bonding to the adjacent atom).

Any carbon or heteroatom with unsatisfied valences in the text, schemes, examples, structural formulae, and any Tables herein is assumed to have a hydrogen atom or atoms of sufficient number to satisfy the valences.

As used herein, "alkyl" is intended to include both branched- and straight-chain saturated aliphatic hydrocarbon groups having the specified number of carbon atoms. For example, "$C_1$-$C_6$" or "$C_{1-6}$," as in "$C_1$-$C_6$alkyl" or "$C_{1-6}$ alkyl," is defined to include groups having 1, 2, 3, 4, 5, or 6 carbons in a linear or branched arrangement. $C_{1-6}$ alkyl includes all of the hexyl alkyl and pentyl alkyl isomers, as well as n-, iso-, sec- and t-butyl, n- and isopropyl, ethyl and methyl. As another example, $C_{1-4}$ alkyl means n-, iso-, sec- and t-butyl, n- and isopropyl, ethyl and methyl. Commonly used abbreviations for alkyl groups may be used throughout the specification, e.g. methyl may be represented by conventional abbreviations including "Me" or $CH_3$ or a symbol that is an extended bond without defined terminal group, e.g.

ethyl may be represented by "Et" or $CH_2CH_3$; propyl may be represented by "Pr" or $CH_2CH_2CH_3$; butyl may be represented by "Bu" or $CH_2CH_2CH_2CH_3$, etc. The term "cycloalkyl" means a mono- or bicyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, cyclopentenyl, cyclobutenyl and so on.

The term "alkenyl" refers to a non-aromatic hydrocarbon radical, straight or branched, containing at least one carbon-to-carbon double bond. Preferably, one carbon-to-carbon double bond is present, and up to 4 non-aromatic carbon-carbon double bonds may be present. As an example, "$C_3$-$C_6$ alkenyl" or "$C_{3-6}$ alkenyl" means an alkenyl radical having from 3 to 6 carbon atoms. Alkenyl groups include ethenyl, propenyl, butenyl and cyclohexenyl. The straight, branched or cyclic portion of the alkenyl group may contain double bonds and may be substituted if a substituted alkenyl group is indicated.

The term "alkynyl" refers to a hydrocarbon radical, straight or branched, containing at least one carbon-to-carbon triple bond. Up to 3 carbon-carbon triple bonds may be present. As an example, "$C_3$-$C_6$ alkynyl" or "$C_{3-6}$ alkynyl" means an alkynyl radical having from 3 to 6 carbon atoms. Alkynyl groups include ethynyl, propynyl and butynyl. The straight or branched portion of the alkynyl group may contain triple bonds and may be substituted if a substituted alkynyl group is indicated.

The term "aryl" (sometimes abbreviated "Ar") means an aromatic monocyclic or multicyclic (e.g., bicyclic) ring system comprising about 6 to about 14 carbon atoms, preferably about 6 to about 10 carbon atoms. The aryl group can be optionally substituted with one or more independently selected substituents. Non-limiting examples of suitable aryl groups include phenyl (which also may be abbreviated herein as "Ph" for convenience), naphthyl, tetrahydro-naphthyl, indanyl and biphenyl phenyl, Bonding can be through any of the carbons in the aromatic ring.

The term "heterocycle," as used herein, includes both unsaturated (including partially unsaturated) and saturated heterocyclic moieties that can be monocyclic or multicyclic (e.g., bicyclic). They generally comprise about 5 to about 14 ring atoms, preferably about 5 to about 10 ring atoms, in which one or more of the ring atoms is an element other than carbon, for example nitrogen, oxygen or sulfur, alone or in combination. Unsaturated heterocyclic moieties include "heteroaryl" (aromatic) moieties, including, for example, benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, imidazolyl, indolinyl, indolyl, dihydroindolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl (pyrimidinyl), pyrrolyl, quinazolinyl, quinolyl, quinoxalinyl, tetrahydroquinoxalinyl, tetrazolyl, tetrazolopyridyl, thiadiazolyl, thiazolyl, thienyl, triazolyl, and N-oxides thereof. Saturated heterocyclic moieties, also known as "heterocyclyl" or "heterocycloalkyl," are non-aromatic, saturated monocyclic or multicyclic ring systems comprising from about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Examples of saturated heterocylic moieties include, for example, azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof. Bridged ring systems are also included in the definition of "heterocycle," including, for example, azabicyclo[2.2.1]heptane. A bridged ring occurs when one or more carbon and/or heteroatoms atoms link two non-adjacent carbon atoms. It is noted that a single bridge converts a monocyclic ring into a bicyclic ring. When a ring is bridged, the substituents recited for the ring may also be present on the bridge. Thus, a heterocycle can be optionally substituted at any chemically available ring atoms by one or more independently selected substituents.

As appreciated by those of skill in the art, halogen or halo as used herein is intended to include fluoro, chloro, bromo and iodo. The term "trifluoromethyl" refers to the group (—$CF_3$). The term "hydroxyl" or "hydroxy" means an "—OH" group.

The term "pharmaceutically acceptable salts" refers to salts prepared from pharmaceutically acceptable non-toxic bases or acids, including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Compositions and Uses

The adenosine signaling pathway has been implicated in a wide range of biological functions. This has suggested a potential role for adenosine receptors in a variety of disease processes in humans or other species. As $A_{2A}$ receptor antagonists, the compounds of the present invention could potentially have utility in treating, preventing, ameliorating, controlling or reducing the risk of one or more disorders associated with $A_{2A}$ receptor function. Thus, the present invention is directed to a compound of Formula I or a pharmaceutically acceptable salt thereof that could be useful in medicine.

An embodiment of the present invention is directed to the use of compounds disclosed herein as antagonists of $A_{2A}$ receptor activity. The subject compounds may be useful in a method of antagonizing $A_{2A}$ receptor activity in a subject, such as a mammal in need of such inhibition, comprising administering a therapeutically effective amount of the compound to the subject. In another aspect, the present invention provides pharmaceutical formulations (pharmaceutical compositions) comprising at least one compound, or pharmaceutically acceptable salt thereof, of Formula I for use in antagonizing $A_{2A}$ receptors for the potential treatment of disorders or diseases related to the adenosine signaling pathway. Thus, the present invention provides for use of the compounds described herein for the potential treatment, management, alleviation or amelioration of conditions or disease states that can be, or are believed to be, treated, managed, alleviated or ameliorated by specific blocking of adenosine A2a receptors. Disorders or diseases that may be impacted by antagonizing the $A_{2A}$ receptors include, among others, central nervous system (CNS) disorders, for example, movement disorders associated with Parkinson's disease. The present invention may further be directed to a use of a compound of the present invention, or a pharmaceutically acceptable salt thereof, for the manufacture of a medicament for antagonizing $A_{2A}$ receptor activity and/or treating one or more of the disorders and diseases noted herein in humans and animals.

One embodiment of the present disclosure provides methods of using the compounds of Formula I to treat a neurological and/or neurodegenerative disease. Thus, the present invention may further be directed to a use of a compound of the present invention, or a pharmaceutically acceptable salt thereof, for the manufacture of a medicament to treat neurological and/or neurodegenerative disease. Neurodegenerative disease can be any of a disease, disorder, condition, sickness or illness that causes any degeneration, lesion, damage, deterioration or collapsing of neurons, such as dopamine-producing neurons. Such diseases include, but are not limited to, any of Parkinson's disease, Alzheimer's disease, Lewy body variant Alzheimer's disease, amyotrophic lateral sclerosis, dementia, multiple system atrophy, neuronal intranuclear inclusion disease, Huntington's disease, corticobasal degeneration, Wilson's disease or other disorders of the basal ganglia that results in dyskinesias, post-traumatic stress disorder, hepatic cirrhosis, sepsis, spinal cord injury, retinopathy, hypertension, social memory impairment, depression, neuroprotection, and Tourettes syndrome. In certain aspects of the present disclosure, the disease is Parkinson's disease.

A specific embodiment of the present invention includes methods of using the compounds of Formula I to treat at least one symptom associated with Parkinson's disease. The at least one symptom associated with Parkinson's disease includes, but is not limited to, cognition impairment or decline, a motor symptom such as tremors, bradykinesias, gait, dystonias, dyskinesias, tardive dyskinesias, other extrapyramidal syndromes, muscle stiffness, joint stiffness, spasm, low muscle control, movement difficulty, rigidity in arms, rigidity in legs, reduced locomotor activity, and movement coordination, or any combination thereof. The compounds of the invention also have the potential for use in preventing or lessening the effect of drugs that cause movement disorders.

An embodiment of the present invention includes methods of antagonizing the $A_{2A}$ receptor for the potential treatment of one or more additional disorders or diseases associated with adenosine receptor signaling, including but not limited to: attention related disorders such as attention deficit disorder (ADD) and attention deficit hyperactivity disorder (ADHD), psychoses, stroke, extra pyramidal syndrome (e.g., dystonia, akathisia, pseudoparkinsonism and tardive dyskinesia, and disorders of abnormal movement such as restless leg syndrome (RLS) and periodic limb movement in sleep (PLMS), cirrhosis, fibrosis, fatty liver, mitigation of addictive behavior, dermal fibrosis in diseases such as scleroderma, sleep related disorders, nocturnal myoclonus, narcolepsy, migraine, inflammation, wound healing, cerebral ischaemia, myocardial ischemia, drug addiction, post-traumatic stress disorder, vascular injury and cancer (such as prostate, rectal, renal, ovarian, endometrial, thyroid, pancreatic, and, particularly, breast, colon, bladder, brain, glia, pineal gland and lung cancer (e.g., Lewis lung carcinoma) or melanoma).

In addition to the potential treatment of warm-blooded animals such as mice, rats, horses, cattle, sheep, dogs, cats, monkeys, etc., the compounds of the invention may be effective for use in humans, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect a disease or disorder by treating a patient presently afflicted with a disease or disorder or by prophylactically treating a patient afflicted with the disease or disorder with a therapeutically effective amount of the compound of the present invention. As used herein, the terms "treatment" and "treating," in reference to a disorder/diseases or a symptom thereof, refer to all processes wherein there may be a slowing, interrupting, arresting, controlling, or stopping of the progression of diseases/disorders described herein or a symptom thereof, but does not necessarily indicate a total elimination of all symptoms, as well as the prophylactic therapy of the mentioned conditions, particularly in a patient who is predisposed to such disease or disorder. The terms "administration of" and or "administering a" compound should be understood to mean providing a compound of the invention or a prodrug of such compound, or any pharmaceutical composition thereof, of the invention to a subject in need thereof.

The compounds of the present invention may be administered by oral, parenteral (e.g., intramuscular, intraperitoneal, intravenous, ICV, intracisternal injection or infusion, subcutaneous injection, or implant), inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

The term "composition" as used herein, such as "pharmaceutical composition," is intended to encompass a product comprising the specified ingredients in the specified amounts, as well as any product which results, directly or indirectly, from combination of the specified ingredients in the specified amounts. Such term in relation to pharmaceutical composition is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The dosage of active ingredient in the compositions of this invention may be varied; however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends on the desired therapeutic effect, the route of administration, and the duration of the treatment. The dose will vary from patient to patient depending upon the nature and severity of disease, the patient's weight, special diets then being followed by a patient, concurrent medication, and other factors that those skilled in the art will recognize Generally, dosage levels of between 0.0001 to 10 mg/kg of body weight daily are administered to the patient, e.g., humans and elderly humans, to obtain effective antagonism of orexin receptors. The dosage range will generally be about 0.5 mg to 1.0 g per patient per day, which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day.

In one embodiment, pharmaceutical compositions of the present invention may be provided in a solid dosage formulation, such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 mg of the active ingredient, such as 1, 5, 10, 15, 20, 25, 50, 75, 100, 150, 200, 250, 300, 400, 500, 600, 750, 800, 900, and 1000 mg of the active ingredient for the symptomatic adjustment of the dosage to the patient to be treated. The compounds may be administered on a regimen of 1 to 4 times per day, such as once or twice per day. The compounds may be administered before bedtime. For example, the compounds may be administered about 1 hour prior to bedtime, about 30 minutes prior to bedtime or immediately before bedtime.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with one or more other therapeutic agent that is known in the art to be useful treating central nervous system (CNS) disorders, for example, movement disorders associated with Parkinson's disease or the treatment. Thus, an embodiment of the invention includes use of a compound of formula I, as hereinbefore defined, and another therapeutic agent for the preparation of a medicament for the treatment of a disease or disorder ameliorated by the inhibition of the $A_{2A}$ receptor, wherein the compound of formula I is administered sequentially, simultaneously or concomitantly with the other therapeutic agent. When used herein, the term "other therapeutic agent" or "another therapeutic agent" includes references to one or more therapeutic agents (e.g., one therapeutic agent) that is known to be useful for (e.g., that is known to be effective in) the treatment of, for example, a disease of the CNS such as depression, a cognitive function disease, a neurodegenerative disease (such as Parkinson's disease, Huntington's disease, Alzheimer's disease, amyotrophic lateral sclerosis) and psychoses; an attention related disorder (such as ADD) and ADHD; extra pyramidal syndrome (e.g., dystonia, akathisia, pseudoparkinsonism and tardive dyskinesia); a disorder of abnormal movement (such as RLS and PLMS); cirrhosis; liver fibrosis; fatty liver; dermal fibrosis (e.g., in diseases such as scleroderma); a sleep disorder; stroke; brain injury or neuroinflammation (e.g., migraine or any disorder or condition caused by ischemia, stroke, head injury or CNS inflammation); and addictive behavior. In one embodiment, the one or more other therapeutic agent does not exert its therapeutic effect by way of binding to an adenosine receptor (e.g., the $A_{2A}$ receptor).

In an embodiment, the present disclosure provides methods and compositions for treating symptoms associated with neurodegenerative diseases by administering an $A_{2A}$ antagonist as described herein optionally in combination with one or more therapeutic agent used to treat said disorders, including, for example, levodopa (L-DOPA), dopamine agonists (e.g., pramipexole, ropinirole or rotigotine), monoamine oxidase B inhibitors (e.g., selegiline or rasagiline), catechol O-methyl transferase inhibitors (e.g., entacapone or tolcapone), amantadine, acetylcholinesterase inhibitors (e.g., donepezil, rivastigmine or galantamine) and glutamate inhibitors (e.g., memantine). In particular, the present disclosure provides methods and compositions for the treatment of symptoms associated with neurodegenerative diseases by administering an $A_{2A}$ antagonist as described herein optionally in combination dopamine precursor or dopamine receptor agonist.

A dopamine precursor used for the purpose of this aspect of the present disclosure can in various aspects be levodopa, also commonly known as, L-3,4-dihydrophenylalanine, L-DOPA or any derivative thereof. Levodopa is the most commonly prescribed drug for treatment of Parkinson's disease. Levodopa derivative includes levodopa methyl ester (LDME, as described in U.S. Pat. No. 4,826,875), L-metatyrosine (as described in U.S. Pat. No. 3,838,008), levodopa ethyl ester (LDEE, as described in U.S. Pat. No. 6,696,600) or salts thereof. Levodopa derivative salts include, but are not limited to, the following: fumarate salt, fumarate dihydrate salt, hydrochloride salt, the hydrobromide salt, the nitrate salt, perchlorate salt, phosphate salt, sulfate salt, formate salt, acetate salt, aconite salt, ascorbate salt, benzosulphonate salt, benzoate salt, cinnamate salt, citrate salt, embonate salt, enantate salt, fumarate salt, glutamate salt, glycolate salt, lactate salt, maleate salt, malonate salt, mandelate salt, methane sulphonate salt, myristate salt, octanoate salt, phthalate salt, salicylate salt, sorbate salt, stearate salt, succinate salt, succinate dihydrate salt, tartrate salt, and the like. Such salts can be obtained following procedures known in the art.

A dopamine receptor agonist used for the purpose of this aspect of the present disclosure can in various aspects be apomorphine, pramipexole, bromocriptine, cabergoline, ropinirole, or rotigotine, or a combination thereof.

An $A_{2A}$ antagonist of the present invention can be administered concomitantly with another therapeutic agent, including but not limited to a dopamine precursor or dopamine receptor agonist. Such concomitant administration can include any form of administration in which the active ingredients are administered together, such as in association in a pharmaceutical composition, or separately. In reference to concomitant administration of an $A_{2A}$ antagonist of the present invention and a dopamine precursor or dopamine receptor agonist, it is intended that any form of administration can be used that enables the potentiation of dopamine precursor-induced treatment of the symptoms associated with a neurodegenerative condition. For example, a separate administration of an $A_{2A}$ antagonist and dopamine precursor or a dopamine receptor agonist is may be performed within a time frame that enables each of these compounds or a combination of these compounds to enter into blood circulation, pass through the hematoencephalic barrier, and exert its/their action on the brain, where the action of one compound potentiates the action of the other compound(s).

The utility of the compounds in accordance with the present invention as $A_{2A}$ receptor antagonists may be readily determined without undue experimentation by methodologies well known in the art, including by a competition binding assay using Scintillation Proximity technology. Briefly, membranes from CHO-K1 cells expressing the human $A_{2A}$ receptor are incubated with a test compound at various concentrations, e.g., ranging from 3000 nM to 0.15 nM, in a reaction mixture also containing a tritiated form of 5-amino-7-[2-phenethyl]-2-(furan-2-yl)-7H-pyrazolo[4,3-e][1,2,4]triazolo[1,5-c]pyrimidine (the tritiated compound) and wheatgerm agglutin-coated yttrium silicate SPA beads at room temperature. The beads are then allowed to settle to the bottom of the wells, after which the membrane-associated radioactivity is determined by scintillation counting in a microplate reader. Ki values can be determined using the Cheng-Prusoff equation. All of the final compounds of the following Examples had activity in antagonizing the human $A_{2A}$ receptor the assay described above, each having a Ki of between about 0.8 nM and 350 nM.

Several methods for preparing the compounds of this invention are illustrated in the following Schemes and Examples. Starting materials are made according to procedures known in the art or as illustrated herein. The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

EXAMPLES

The following general synthetic schemes are useful for preparation of intermediates and reagents that can be used in the preparation of the compounds of the invention.

Intermediate 1

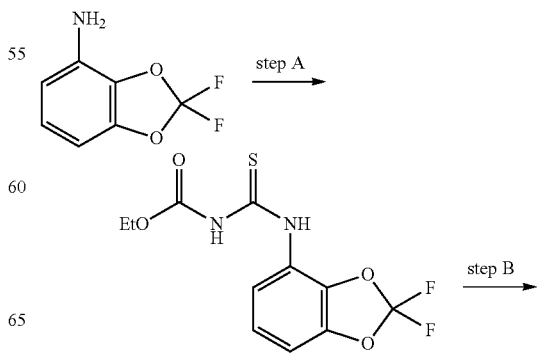

-continued

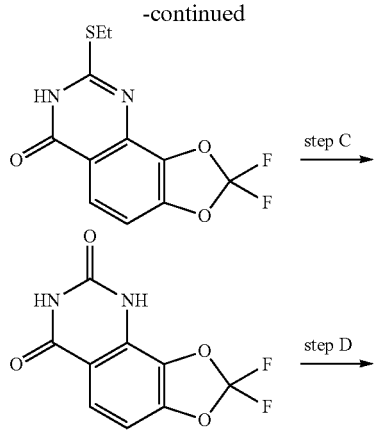

6,8-dichloro-2,2-difluoro-[1,3]dioxolo[4,5-h]qui-
nazoline

Step A: ethyl [(2,2-difluoro-1,3-benzodioxol-4-yl)carbamothioyl]carbamate

Ethyl isothiocyanate formate (4.0 mL, 34 mmol, 1.0 equiv.) was slowly added to a stirring dichloromethane (100 mL) solution of 2,2-difluoro-1,3-benzodioxol-4-amine (5.8 g, 34 mmol) at room temperature. The resulting mixture was stirred for 4 hours, and the solvent was evaporated to give the title compound as a pale yellow solid that was used in the next step without further purification.

Step B: 8-(ethylthio)-2,2-difluoro-[1,3]dioxolo[4,5-h]quinazolin-6(7H)-one

To a stirring acetone (100 mL) solution of ethyl [(2,2-difluoro-1,3-benzodioxol-4-yl)carbamothioyl]carbamate (10.2 g, 33.6 mmol, step A) was added ethyl iodide (2.7 mL, 34 mmol, 1.0 equiv.) followed by potassium carbonate at room temperature. The resulting mixture was stirred for 17 hours and filtered through a pad of diatomaceous earth. Concentration of the filtrate afforded a crude solid, which was then dissolved in dichloromethane (200 mL), washed with water, brine, dried, and concentrated in vacuo. The yellow oil thus obtained was mixed with diphenyl ether (100 g) and heated at 200° C. for 19 hours. The mixture was cooled to room temperature and charged with hexanes. Filtration of this mixture afforded the title compound as a white solid by filtration. LC/MS=287 [M+1].

Step C: 2,2-difluoro-[1,3]dioxolo[4,5-h]quinazoline-6,8(7H,9H)-dione

To an ethanol (150 mL) solution of 8-(ethylthio)-2,2-difluoro-[1,3]dioxolo[4,5-h]quinazolin-6(7H)-one (4.2 g, 15 mmol, step B) at room temperature was added 6 N aqueous hydrochloric acid (150 mL). The resulting mixture was heated at 80° C. for 15 hours and then cooled to room temperature. Hexanes were added, and the precipitate was filtered off, washed with water and hexanes to give the title compound as a white solid. LC/MS=243 [M+1].

Step D: 6,8-dichloro-2,2-difluoro-[1,3]dioxolo[4,5-h]quinazoline 2,2-Difluoro-[1,3]dioxolo[4,5-h]quinazoline-6,8(7H,9H)-dione (1.56 g, 6.5 mmol, step C) and phosphorus oxychloride (40 mL) was charged into a 150-mL sealed tube. The resulting mixture was heated at 130° C. for 15 hours. The mixture was cooled to room temperature, diluted in toluene, and the volatiles were removed in vacuo. The residue was dissolved in ethyl acetate and stirred with aqueous sodium hydrogencarbonate at room temperature for 25 minutes. The aqueous layer was extracted with ethyl acetate, and the combined organic extracts were dried and concentrated in vacuo to afford the title compound as a white solid.

Intermediate 2

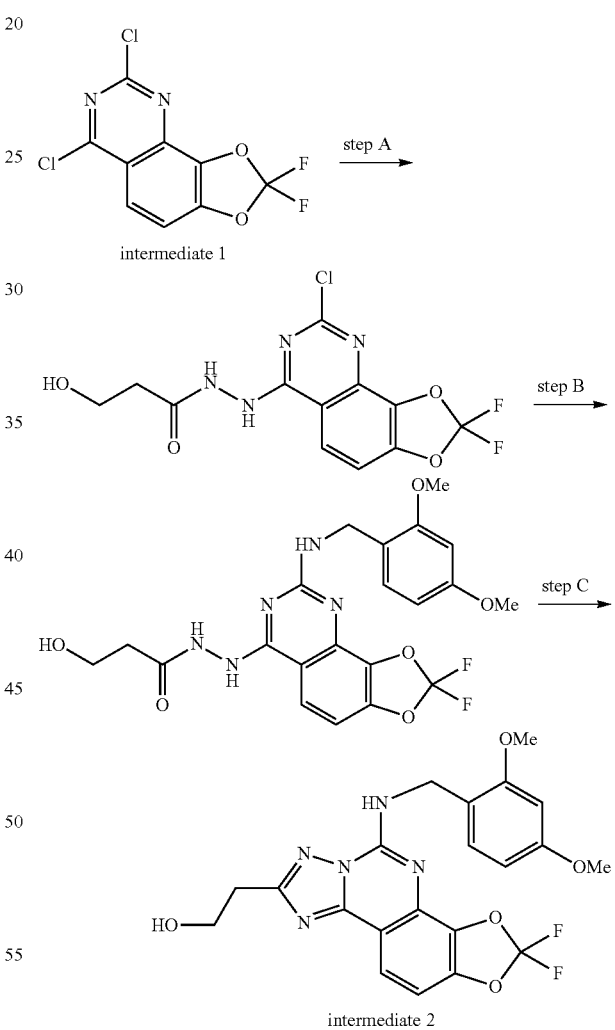

2-(5-((2,4-dimethoxybenzyl)amino)-2,2-difluoro-[1,3]dioxolo[4,5-h][1,2,4]triazolo[1,5-c]quinazolin-8-yl)ethanol

Step A: N'-(8-chloro-2,2-difluoro-[1,3]dioxolo[4,5-h]quinazolin-6-yl)-3-hydroxypropanehydrazide To a 150-mL sealed tube with 6,8-dichloro-2,2-difluoro-[1,3]dioxolo[4,5-h]quinazoline (1.7 g, 6.1 mmol, intermediate 1), 3-hydroxypropanehydrazide (0.7 g, 6.7 mmol, 1.1 equiv.) and N,N-diisopropylethylamine (2.1 mL, 12 mmol, 2.0 equiv.) was charged dry tetrahydrofuran (60 mL). The reaction mixture was heated at 65° C. for 22 hours and then cooled to room temperature. It was concentrated in vacuo to afford the title compound as a crude solid. LC/MS=347 [M+1].

Step B: N'-(8-((2,4-dimethoxybenzyl)amino)-2,2-difluoro-[1,3]dioxolo[4,5-h]quinazolin-6-yl)-3-hydroxypropanehydrazide In a 250-mL round bottomed flask with N'-(8-chloro-2,2-difluoro-[1,3]dioxolo[4,5-h]quinazolin-6-yl)-3-hydroxypropanehydrazide (6.1 mmol, step A), 2,4-dimethoxybenzylamine (1.8 mL, 12 mmol, 2.0 equiv.) and N,N-diisopropylethylamine (3.2 mL, 18 mmol, 3.0 equiv.) was charged dry dioxane (100 mL). The resulting mixture was heated at 120° C. for 18 hours and then cooled to room temperature. It was concentrated in vacuo to afford a crude solid. Water was added to the crude solid, and the mixture was extracted with dichloromethane twice. Hexanes was added to the combined organic extracts, and the precipitate was filtered off, washed with hexanes and dried to afford the title compound as an orange solid. LC/MS=478 [M+1].

Step C: 2-(5-((2,4-dimethoxybenzyl)amino)-2,2-difluoro-[1,3]dioxolo[4,5-h][1,2,4]triazolo[1,5-c]quinazolin-8-yl)ethanol In a 150-mL sealed tube, N-(8-((2,4-dimethoxybenzyl)amino)-2,2-difluoro-[1,3]dioxolo[4,5-h]quinazolin-6-yl)-3-hydroxypropanehydrazide (1.7 g, 6.1 mmol, step B) and N,O-bis(trimethylsilyl)acetamide (50 mL). The resulting mixture was heated at 140° C. for 16 hours and then cooled to room temperature. Volatiles were removed in vacuo at 70° C., and the residue was charged with toluene (100 mL) and concentrated in vacuo. Methanol (8 mL) was added, followed by concentrated hydrochloric acid (0.2 mL), and the resulting mixture was stirred at room temperature for 10 minutes. A 0.05 M aqueous solution of sodium hydrogencarbonate (75 mL) was added, and the resulting mixture was stirred for 5 minutes. After 2 hours, filtration of the mixture afforded the title compound as a yellow solid. LC/MS=460 [M+1].

Intermediate 3

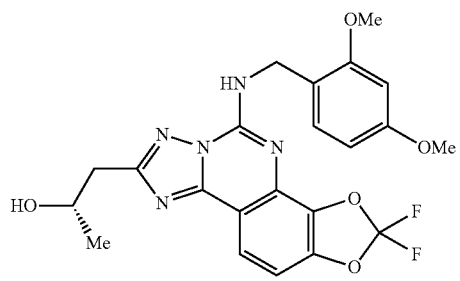 [SMILES: COc1ccc(CNc2nc3c4c(ccc3c3nc(C[C@H](C)O)nn23)OC(F)(F)O4)c(OC)c1]

(S)-1-(5-((2,4-dimethoxybenzyl)amino)-2,2-difluoro-[1,3]dioxolo[4,5-h][1,2,4]triazolo[1,5-c]quinazolin-8-yl)propan-2-ol The title compound was synthesized by following the procedures described in intermediate 2, substituting (S)-3-hydroxybutanehydrazide for 3-hydroxypropanehydrazide in step A. LC/MS=474 [M+1].

Intermediate 4

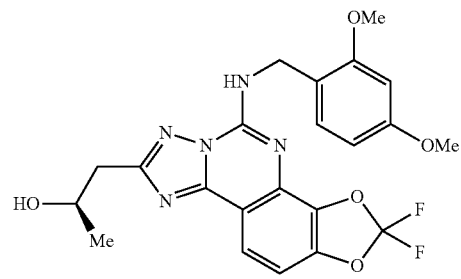 [SMILES: COc1ccc(CNc2nc3c4c(ccc3c3nc(C[C@@H](C)O)nn23)OC(F)(F)O4)c(OC)c1]

(R)-1-(5-((2,4-dimethoxybenzyl)amino)-2,2-difluoro-[1,3]dioxolo[4,5-h][1,2,4]triazolo[1,5-c]quinazolin-8-yl)propan-2-ol The title compound was synthesized by following the procedures described in intermediate 2, substituting (R)-3-hydroxybutanehydrazide for 3-hydroxypropanehydrazide in step A. LC/MS=474 [M+1].

Intermediate 5

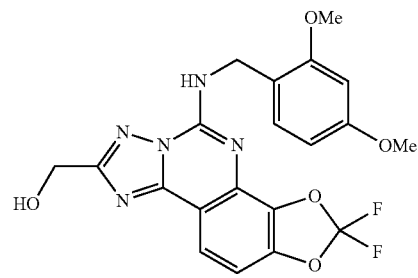 [SMILES: COc1ccc(CNc2nc3c4c(ccc3c3nc(CO)nn23)OC(F)(F)O4)c(OC)c1]

(5-((2,4-dimethoxybenzyl)amino)-2,2-difluoro-[1,3]dioxolo[4,5-h][1,2,4]triazolo[1,5-c]quinazolin-8-yl)methanol The title compound was synthesized by following the procedures described in intermediate 2, substituting 2-hydroxyacetohydrazide for 3-hydroxypropanehydrazide in step A. LC/MS=446 [M+1].

Intermediate 6

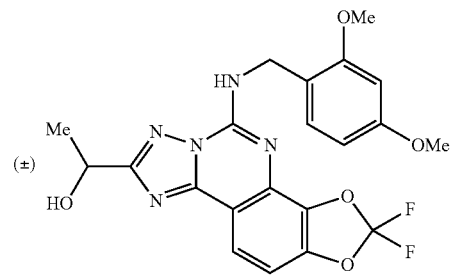 [SMILES: COc1ccc(CNc2nc3c4c(ccc3c3nc(C(C)O)nn23)OC(F)(F)O4)c(OC)c1]

(±)-1-(5-((2,4-dimethoxybenzyl)amino)-2,2-difluoro-[1,3]dioxolo[4,5-h][1,2,4]triazolo[1,5-c]quinazolin-8-yl)ethanol The title compound was synthesized by following the procedures described in intermediate 2, substituting (±)-2-hydroxypropanehydrazide for 3-hydroxypropanehydrazide in step A. LC/MS=460 [M+1].

Intermediate 7

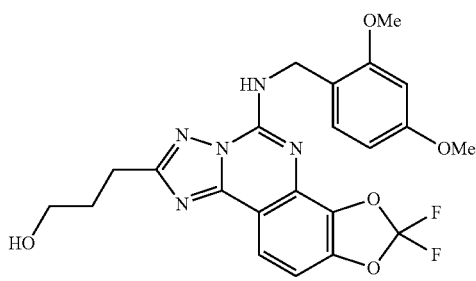 [SMILES: COc1ccc(CNc2nc3c4c(ccc3c3nc(CCCO)nn23)OC(F)(F)O4)c(OC)c1]

3-(5-((2,4-dimethoxybenzyl)amino)-2,2-difluoro-[1,3]dioxolo[4,5-h][1,2,4]triazolo[1,5-c]quinazolin-8-yl)propan-1-ol The title compound was synthesized by following the procedures described in intermediate 2, substituting 4-hydroxybutanehydrazide for 3-hydroxypropanehydrazide in step A. LC/MS=474 [M+1].

Intermediate 8

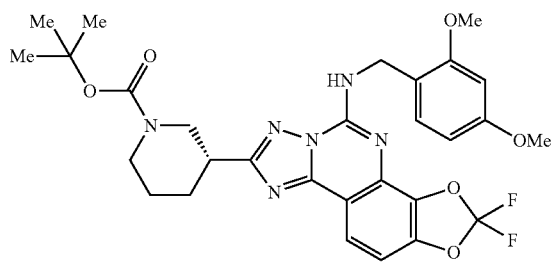 [SMILES: COc1ccc(CNc2nc3c4c(ccc3c3nc([C@@H]5CCCN(C(=O)OC(C)(C)C)C5)nn23)OC(F)(F)O4)c(OC)c1]

(R)-tert-butyl 3-(5-((2,4-dimethoxybenzyl)amino)-2,2-difluoro-[1,3]dioxolo[4,5-h][1,2,4]triazolo[1,5-c]quinazolin-8-yl)piperidine-1-carboxylate The title compound was synthesized by following the procedures described in intermediate 2, substituting (R)-tert-butyl 3-(hydrazinecarbonyl)piperidine-1-carboxylate for 3-hydroxypropanehydrazide in step A. LC/MS=599 [M+1].

Example 1

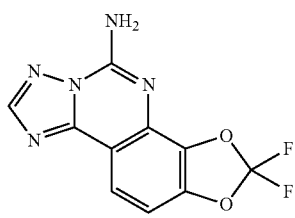 [SMILES: Nc1nc2c3c(ccc2c2ncnn12)OC(F)(F)O3]

2,2-difluoro-[1,3]dioxolo[4,5-h][1,2,4]triazolo[1,5-c]quinazolin-5-amine

Step A: 8-chloro-2,2-difluoro-6-hydrazinyl-[1,3]dioxolo[4,5-h]quinazoline

To a stirring tetrahydrofuran (36 mL) solution of 6,8-dichloro-2,2-difluoro-[1,3]dioxolo[4,5-h]quinazoline (1.0 g, 3.6 mmol, intermediate 1) was added hydrazine hydrate (0.34 mL, 5.4 mmol) and N,N-diisopropylethylamine (0.75 mL, 4.3 mmol) at room temperature. The reaction mixture was stirred for 4 hours and concentrated in vacuo to afford the crude product. Chromatography over silica gel, eluting with hexanes/ethyl acetate and dichloromethane/methanol, afforded the title compound. LC/MS=275 [M+1].

Step B: 5-chloro-2,2-difluoro-[1,3]dioxolo[4,5-h][1,2,4]triazolo[4,3-c]quinazoline To a stirring dichloromethane (20 mL) solution of 8-chloro-2,2-difluoro-6-hydrazinyl-[1,3]dioxolo[4,5-h]quinazoline (900 mg, 3.3 mmol, step A) at room temperature was added trimethyl orthoformate (1100 µL, 9.8 mmol). The reaction mixture was stirred at room temperature for 2 hours. Trifluoroacetic acid (760 µL, 9.8 mmol) was added, and the reaction mixture was stirred for 12 hours. The reaction mixture was diluted with dichloromethane and charged with aqueous sodium hydrogencarbonate. The aqueous layer was extracted with dichloromethane, and the combined organic extracts were washed with brine, dried (magnesium sulfate), filtered and concentrated in vacuo to afford the crude product. Chromatography over silica gel, eluting with dichloromethane/methanol, afforded the title compound as a white solid. LC/MS=285 [M+1].

Step C: N-(2,4-dimethoxybenzyl)-2,2-difluoro-[1,3]dioxolo[4,5-h][1,2,4]triazolo[4,3-c]quinazolin-5-amine To a stirred dioxane (34 mL) solution of 5-chloro-2,2-difluoro-[1,3]dioxolo[4,5-h][1,2,4]triazolo[4,3-c]quinazoline (960 mg, 3.4 mmol, step B) was added 2,4-dimethoxybenzylamine (1,100 mg, 6.8 mmol) and N,N-diisopropylethylamine (1.8 mL, 10 mmol) at room temperature. It was heated to 85° C. and stirred for 12 hours. After the reaction mixture was cooled down to room temperature, it was concentrated in vacuo and redissolved in ethyl acetate. The organic phase was washed with aqueous sodium hydrogencarbonate, brine, dried (magnesium sulfate), filtered and concentrated in vacuo to afford the crude product. Chromatography over silica gel, eluting with hexanes/ethyl acetate, afforded the title compound. LC/MS=416 [M+1].

Step D: N-(2,4-dimethoxybenzyl)-2,2-difluoro-[1,3]dioxolo[4,5-h][1,2,4]triazolo[1,5-c]quinazolin-5-amine In a microwave tube, N-(2,4-dimethoxybenzyl)-2,2-difluoro-[1,3]dioxolo[4,5-h][1,2,4]triazolo[1,5-c]quinazolin-5-amine (1.2 g, 2.9 mmol, step C) was charged with N,O-bis(trimethylsilyl)acetamide (8.8 g, 43 mmol). The tube was capped and heated to 120° C. for 12 hours. After the reaction mixture was cooled down, it was heated to 55° C. in vacuo to remove the volatiles. The residue was dissolved in ethyl acetate. The solution thus obtained was washed with aqueous ammonium chloride solution, brine, dried (magnesium sulfate), filtered and concentrated in vacuo to afford the crude product. Chromatography over silica gel, eluting with hexanes/ethyl acetate, afforded the title compound. LC/MS=416 [M+1].

Step E: 2,2-difluoro-[1,3]dioxolo[4,5-h][1,2,4]triazolo[1,5-c]quinazolin-5-amine In a round-bottom-flask, N-(2,4-dimethoxybenzyl)-2,2-difluoro-[1,3]dioxolo[4,5-h][1,2,4]triazolo[1,5-c]quinazolin-5-amine (25 mg, 0.060 mmol, step D) was charged with trifluoroacetic acid (600 µL) at room temperature. The reaction mixture was heated to 50° C. for 2 hours. Solvent was removed in vacuo, and the crude product was diluted with dichloromethane and neutralized with a 7.0 N methanolic solution of ammonia. Concentration of the mixture afforded the crude product. Preparative thin-layer chromatography (dichloromethane/methanol; hexanes/ethyl acetate) afforded the title compound as a white solid. LC/MS=266 [M+1].

Example 2

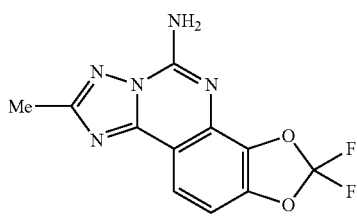 [SMILES: Cc1nc2c3ccc4c(c3nc(N)n2n1)OC(F)(F)O4]

2,2-difluoro-8-methyl-[1,3]dioxolo[4,5-h][1,2,4]triazolo[1,5-c]quinazolin-5-amine Step A: N'-(8-chloro-2,2-difluoro-[1,3]dioxolo[4,5-h]quinazolin-6-yl)acetohydrazide To a stirring tetrahydrofuran (48 mL) solution of 6,8-dichloro-2,2-difluoro-[1,3]dioxolo[4,5-h]quinazoline (2.0 g, 7.2 mmol, intermediate 1) at room temperature was added N,N-diisopropylethylamine (1.5 mL, 8.6 mmol) and acetohydrazide (0.59 g, 7.2 mmol). The reaction mixture was stirred for 12 hours. Concentration of the reaction mixture in vacuo afforded the title compound as a crude solid, which was used in the subsequent step without further purification. LC/MS=317 [M+1].

Step B: N'-(8-((2,4-dimethoxybenzyl)amino)-2,2-difluoro-[1,3]dioxolo[4,5-h]quinazolin-6-yl)acetohydrazide To a stirring dioxane (70 mL) solution of N'-(8-chloro-2,2-difluoro-[1,3]dioxolo[4,5-h]quinazolin-6-yl)acetohydrazide (2.2 g, 7.0 mmol, step A) was added N,N-diisopropylethylamine (3.6 mL, 21 mmol) and 2,4-dimethoxybenzylamine (2.3 g, 14 mmol). The reaction mixture was heated to 95° C. for 12 hours. After the reaction mixture was cooled down, it was filtered and concentrated in vacuo. The residue was dissolved in ethyl acetate, and the organic phase was washed with aqueous sodium hydrogencarbonate and filtered. Concentration of the reaction mixture in vacuo afforded the title compound as a crude solid, which was used in the subsequent step without further purification. LC/MS=448 [M+1].

Step C: N-(2,4-dimethoxybenzyl)-2,2-difluoro-8-methyl-[1,3]dioxolo[4,5-h][1,2,4]triazolo[1,5-c]quinazolin-5-amine In a microwave tube, N'-(8-(2,4-dimethoxybenzyl)amino)-2,2-difluoro-[1,3]dioxolo[4,5-h]quinazolin-6-yl)acetohydrazide (3.0 g, 6.7 mmol, step B) was charged with N,O-bis(trimethylsilyl)acetamide (20 g, 100 mmol). The tube was capped and heated to 120° C. for 12 hours. After the reaction mixture was cooled down, it was heated to 55° C. in vacuo to remove the volatiles. The residue was dissolved in ethyl acetate. The solution thus obtained was washed with aqueous ammonium chloride solution, brine, dried (magnesium sulfate), filtered and concentrated in vacuo to afford the crude product. Chromatography over silica gel, eluting with hexanes/ethyl acetate, afforded the title compound. LC/MS=430 [M+1].

Step D: 2,2-difluoro-8-methyl-[1,3]dioxolo[4,5-h][1,2,4]triazolo[1,5-c]quinazolin-5-amine In a round-bottom-flask, N-(2,4-dimethoxybenzyl)-2,2-difluoro-8-methyl-[1,3]dioxolo[4,5-h][1,2,4]triazolo[1,5-c]quinazolin-5-amine (22 mg, 0.051 mmol, step C) was charged with trifluoroacetic acid (500 µL) at room temperature. The reaction mixture was heated to 50° C. for 2 hours. Solvent was removed in vacuo, and the crude product was diluted with dichloromethane and neutralized with a 7.0 N methanolic solution of ammonia. Concentration of the mixture afforded the crude product. Preparative thin-layer chromatography (dichloromethane/methanol) afforded the title compound as a white solid. LC/MS=280 [M+1].

Example 3

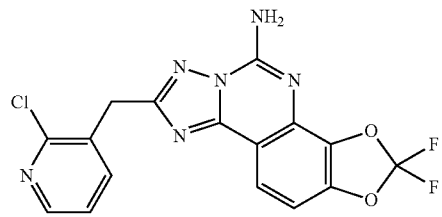 [SMILES: Nc1nc2c3c(ccc2c2nc(Cc4cccnc4Cl)nn12)OC(F)(F)O3]

8-2-chloropyridin-3-yl)methyl)-2,2-difluoro-[1,3]dioxolo[4,5-h][1,2,4]triazolo[1,5-c]quinazolin-5-amine Step A: 2-(2-chloropyridin-3-yl)acetohydrazide A 150-mL sealed tube was charged with ethyl 2-(2-chloropyridin-3-yl)acetate (3.1 g, 15 mmol), hydrazine monohydrate (2.0 mL, 31 mmol, 2.0 equiv.) and methanol (25 mL). The resulting mixture was heated at 85° C. for 43 hours and then cooled to room temperature. Concentration in vacuo afforded the title compound as a white solid. $^1$H NMR (500 MHz, d$_6$-DMSO) δ 9.3 (s, 1H), 8.3 (s, 1H), 7.8 (s, 1H), 7.4 (s, 1H), 4.3 (s, 2H), 3.5 (s, 2H).

Step B: N'-(8-chloro-2,2-difluoro-[1,3]dioxolo[4,5-h]quinazolin-6-yl)-2-(2-chloropyridin-3-yl)acetohydrazide A 150-mL sealed tube with 6,8-dichloro-2,2-difluoro-[1,3]dioxolo[4,5-h]quinazoline (860 mg, 3.1 mmol, intermediate 1), 2-(2-chloropyridin-3-yl)acetohydrazide (630 mg, 3.4 mmol, 1.1 equiv., step A) and N,N-diisopropylethylamine (1.1 mL, 6.2 mmol, 2.0 equiv.) was charged with dry tetrahydrofuran (30 mL), and the resulting mixture was heated at 85° C. for 16 hours. It was cooled to room temperature and concentrated in vacuo to afford a crude solid. Chromatography over silica gel, eluting with dichloromethane/methanol, afforded the title compound as a yellow solid. LC/MS=429 [M+1].

Step C: 2-(2-chloropyridin-3-yl)-N'-(8-((2,4-dimethoxybenzyl)amino)-2,2-difluoro-[1,3]dioxolo[4,5-h]quinazolin-6-yl)acetohydrazide To a 150-mL sealed tube with N'-(8-chloro-2,2-difluoro-[1,3]dioxolo[4,5-h]quinazolin-6-yl)-2-(2-chloropyridin-3- yl)acetohydrazide (1.5 g, 3.6 mmol, step B), 2,4-dimethoxybenzylamine (0.81 mL, 5.4 mmol, 1.5 equiv.) and N,N-diisopropylethylamine (1.9 mL, 11 mmol, 3.0 equiv.) was charged dry dioxane (15 mL). The resulting mixture was heated at 100° C. for 19 hours and then cooled to room temperature. After standing at room temperature for more than 4 hours, the reaction mixture was filtered to remove a white solid, and the filtrate was concentrated in vacuo to afford the title compound as an orange solid. LC/MS=559 [M+1].

Step D: 8-((2-chloropyridin-3-yl)methyl)-N-(2,4-dimethoxybenzyl)-2,2-difluoro-[1,3]dioxolo[4,5-h][1,2,4]triazolo[1,5-c]quinazolin-5-amine In a 15-mL sealed tube, 2-(2-chloropyridin-3-yl)-N'-(8-((2,4-dimethoxybenzyl)amino)-2,2-difluoro-[1,3]dioxolo[4,5-h]quinazolin-6-yl)acetohydrazide (350 mg, 0.62 mmol, step C) was charged with N,O-bis(trimethylsilyl)acetamide (8 mL). The resulting mixture was heated at 140° C. for 15 hours and then cooled to room temperature. Volatiles were removed in vacuo at 70° C. to afford a crude solid. Chromatography over silica gel, eluting with hexanes/ethyl acetate, afforded the title compound as a white solid. LC/MS=541 [M+1].

Step E: 8-((2-chloropyridin-3-yl)methyl)-2,2-difluoro-[1,3]dioxolo[4,5-h][1,2,4]triazolo[1,5-c]quinazolin-5-amine In a round bottomed flask, 8-((2-chloropyridin-3-yl)methyl)-N-(2,4-dimethoxybenzyl)-2,2-difluoro-[1,3]dioxolo[4,5-h][1,2,4]triazolo[1,5-c]quinazolin-5-amine (200 mg, 0.37 mmol, step D) was charged with trifluoroacetic acid (7 mL). The resulting mixture was stirred at room temperature for 20 hours. Solvent was removed in vacuo, and aqueous ammonia was added. The mixture was extracted with dichloromethane, and the combined organic phases was dried and concentrated in vacuo to afford a pale yellow crude solid. It was first purified by flash chromatography over silica gel, eluting with dichloromethane/methanol, followed by reversed-phase HPLC, eluting with water/acetonitrile with trifluoroacetic acid, afforded the title compound as a white solid. LC/MS=391 [M+1].

Example 4

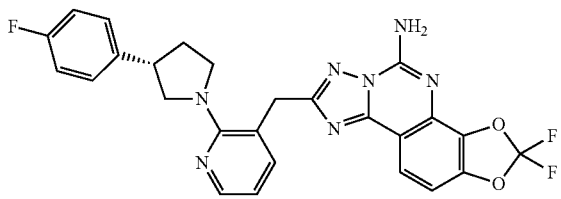 [SMILES: Nc1nc2c3c(ccc2c2nc(Cc4cccnc4N4CC[C@@H](c5ccc(F)cc5)C4)nn12)OC(F)(F)O3]

(S)-2,2-difluoro-8-((2-(3-(4-fluorophenyl)pyrrolidin-1-yl)pyridin-3-yl)methyl)-[1,3]dioxolo[4,5-h][1,2,4]triazolo[1,5-c]quinazolin-5-amine In a conical microwave vial, a mixture of crude 8-((2-chloropyridin-3-yl)methyl)-2,2-difluoro-[1,3]dioxolo[4,5-h][1,2,4]triazolo[1,5-c]quinazolin-5-amine (17%, 260 mg, 0.11 mmol, EXAMPLE 3), (S)-3-(4-fluorophenyl)pyrrolidine (66 mg, 0.40 mmol, 3.5 equiv.) and N,N-diisopropylethylamine (100 µL, 0.57 mmol, 5.1 equiv.) was charged with dry N-methylpyrrolidinone (1 mL). The resulting mixture was irradiated with microwaves at 220° C. for 6 hours and then cooled to room temperature. Water was added, and the mixture was extracted with dichloromethane. The combined organic phase was dried and concentrated in vacuo to afford a crude solid. Reversed-phase HPLC, eluting with water/acetonitrile with trifluoroacetic acid, afforded the title compound as a pale yellow solid. LC/MS=520 [M+1].

Example 5

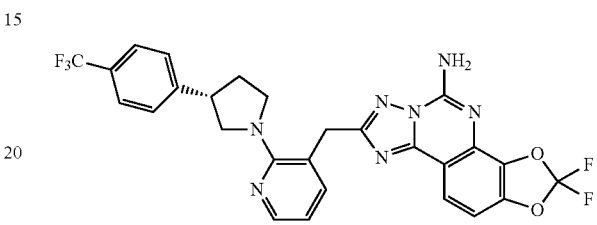

(S)-2,2-difluoro-8-((2-(3-(4-(trifluoromethyl)phenyl)pyrrolidin-1-yl)pyridin-3-yl)methyl)-[1,3]dioxolo[4,5-h][1,2,4]triazolo[1,5-c]quinazolin-5-amine The title compound was synthesized by following the procedures described in example 4, substituting (S)-3-(4-(trifluoromethyl)phenyl)pyrrolidine for (S)-3-(4-fluorophenyl)pyrrolidine. LC/MS=570 [M+1].

Example 6

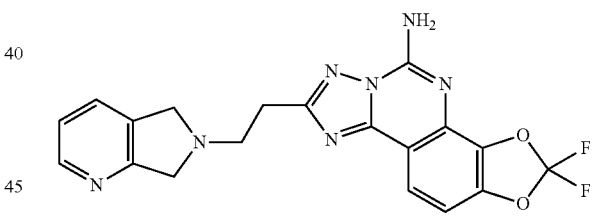

(8-(2-(5H-pyrrolo[3,4-b]pyridin-6(7H)-yl)ethyl)-2,2-difluoro-[1,3]dioxolo[4,5-h][1,2,4]triazolo[1,5-c]quinazolin-5-amine Step A: 2-(5-((2,4-dimethoxybenzyl)amino)-2,2-difluoro-[1,3]dioxolo[4,5-h][1,2,4]triazolo[1,5-c]quinazolin-8-yl)ethyl methanesulfonate To a stirring dichloromethane (5 mL) suspension of 2-(5-((2,4-dimethoxybenzyl)amino)-2,2-difluoro-[1,3]dioxolo[4,5-h][1,2,4]triazolo[1,5-c]quinazolin-8-yl)ethanol (120 mg, 0.26 mmol, intermediate 2) at 0° C. was added triethylamine (0.12 mL, 0.83 mmol, 3.2 equiv.), followed by methanesulfonyl chloride (0.044 mL, 0.57 mmol, 2.2 equiv.). The resulting reaction mixture was warmed up to room temperature and stirred for 30 minutes. It was washed with 1N aqueous sodium hydroxide, dried, and concentrated in vacuo to afford the title compound as yellow crystals. LC/MS=538 [M+1].

Step B: 2-(5-amino-2,2-difluoro-[1,3]dioxolo[4,5-h][1,2,4]triazolo[1,5-c]quinazolin-8-yl)ethyl methanesulfonate In a 15-mL sealed tube, a mixture of 2-(5-((2,4-dimethoxybenzyl)amino)-2,2-difluoro-[1,3]dioxolo[4,5-h][1,2,4]triazolo[1,5-c]quinazolin-8-yl)ethyl methanesulfonate (132 mg, 0.246 mmol, step A) and trifluoroacetic acid (1 mL) was charged with dichloromethane (1 mL). The resulting mixture was heated at 65° C. for 16 hours and then cooled to room temperature. It was concentrated in vacuo, and the residue was redissolved in dichloromethane and washed with aqueous sodium hydroxide. The aqueous layer was extracted twice with dichloromethane, and the combined organic extracts were concentrated in vacuo to afford the title compound as a crude yellow solid. It was used in the subsequent step without further purification. LC/MS=388 [M+1].

Step C: (8-(2-(5H-pyrrolo[3,4-b]pyridin-6(7H)-yl)ethyl)-2,2-difluoro-[1,3]dioxolo[4,5-h][1,2,4]triazolo[1,5-c]quinazolin-5-amine In a 15-mL sealed tube, a mixture of 2-(5-amino-2,2-difluoro-[1,3]dioxolo[4,5-h][1,2,4]triazolo[1,5-c]quinazolin-8-yl)ethyl methanesulfonate (110 mg, 0.28 mmol, step B), N,N-diisopropylethylamine (0.099 mL, 0.57 mmol, 2.0 equiv.), potassium iodide (52 mg, 0.31 mmol, 1.1 equiv.), 6,7-dihydro-5H-pyrrolo[3,4-b]pyridine (68 mg, 0.57 mmol, 2.0 equiv.) was charged with dry N,N-dimethylformamide (5 mL). The resulting mixture was heated at 80° C. for 16 hours and then cooled to room temperature. It was concentrated in vacuo, and the residue was redissolved in dichloromethane and washed with aqueous sodium hydroxide. The aqueous layer was extracted twice with dichloromethane, and the combined organic extracts were concentrated in vacuo to afford the crude solid. Chromatography over silica gel, eluting with dichloromethane/methanol, afforded the title compound as a brown solid. LC/MS=412 [M+1].

The compounds in Table 2 were prepared by using methods described in Example 6, substituting the appropriate amine for 6,7-dihydro-5H-pyrrolo[3,4-b]pyridine.

TABLE 2

| Ex. No. | Structure | IUPAC Name | Exact Mass [M + H]+ |
|---|---|---|---|
| 7 | 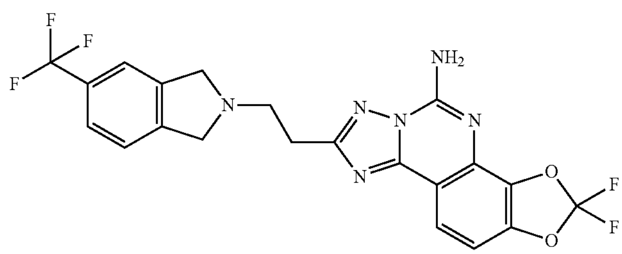 [SMILES: Nc1nc2c3c(ccc2c2nc(CCN4Cc5ccc(C(F)(F)F)cc5C4)nn12)OC(F)(F)O3] | 2,2-difluoro-8-{2-[5-(trifluoromethyl)-1,3-dihydro-2H-isoindol-2-yl]ethyl}[1,3]-dioxolo[4,5-h][1,2,4]triazolo[1,5-c]quinazolin-5-amine | 479 |
| 8 | 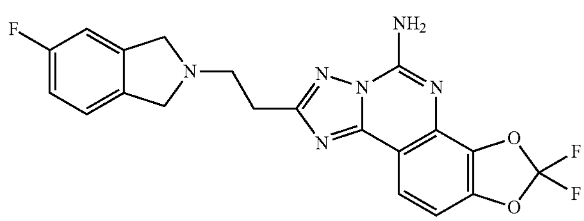 [SMILES: Nc1nc2c3c(ccc2c2nc(CCN4Cc5ccc(F)cc5C4)nn12)OC(F)(F)O3] | 2,2-difluoro-8-[2-(5-fluoro-1,3-dihydro-2H-isoindol-2-yl)ethyl][1,3]dioxolo[4,5-h][1,2,4]triazolo[1,5-c]quinazolin-5-amine | 429 |
| 9 | 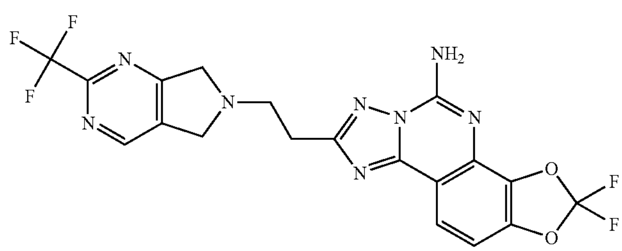 [SMILES: Nc1nc2c3c(ccc2c2nc(CCN4Cc5cnc(C(F)(F)F)nc5C4)nn12)OC(F)(F)O3] | 2,2-difluoro-8-{2-[2-(trifluoromethyl)-5,7-dihydro-6H-pyrrolo[3,4-d]pyrimidin-6-yl]ethyl}[1,3]dioxolo[4,5-h][1,2,4]triazolo[1,5-c]quinazolin-5-amine | 481 |
| 10 | 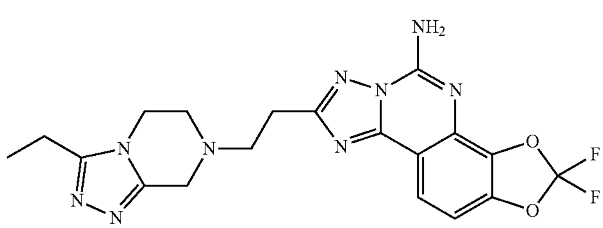 [SMILES: CCc1nnc2n1CCN(CCc1nc3c4ccc5c(c4nc(N)n3n1)OC(F)(F)O5)C2] | 8-[2-(3-ethyl-5,6-dihydro[1,2,4]triazolo[4,3-a]pyrazin-7(8H)-yl)ethyl]-2,2-difluoro[1,3]dioxolo[4,5-h][1,2,4]triazolo[1,5-c]quinazolin-5-amine | 444 |

TABLE 2-continued

| Ex. No. | Structure | IUPAC Name | Exact Mass [M + H]+ |
|---|---|---|---|
| 11 | 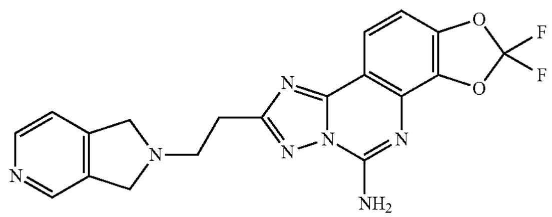 [SMILES: Nc1nc2c3c(ccc2c2nc(CCN4Cc5ccncc5C4)nn12)OC(F)(F)O3] | 8-[2-(1,3-dihydro-2H-pyrrolo[3,4-c]pyridin-2-yl)ethyl]-2,2-difluoro[1,3]dioxolo[4,5-h][1,2,4]triazolo[1,5-c]quinazolin-5-amine | 412 |
| 12 | 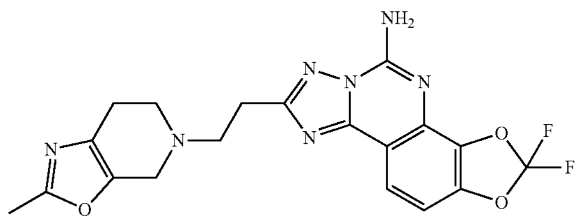 [SMILES: Cc1nc2c(o1)CN(CCc1nc3c4ccc5c(c4nc(N)n3n1)OC(F)(F)O5)CC2] | 2,2-difluoro-8-[2-(2-methyl-6,7-dihydro[1,3]oxazolo[5,4-c]pyridin-5(4H)-yl)ethyl][1,3]dioxolo[4,5-h][1,2,4]triazolo[1,5-c]quinazolin-5-amine | 430 |
| 13 | 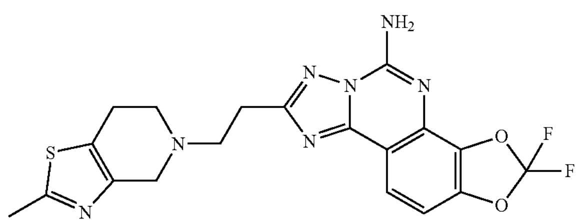 [SMILES: Cc1nc2c(s1)CCN(CCc1nc3c4ccc5c(c4nc(N)n3n1)OC(F)(F)O5)C2] | 2,2-difluoro-8-[2-(2-methyl-6,7-dihydro[1,3]thiazolo[4,5-c]pyridin-5(4H)-yl)ethyl][1,3]dioxolo[4,5-h][1,2,4]triazolo[1,5-c]quinazolin-5-amine | 446 |
| 14 | 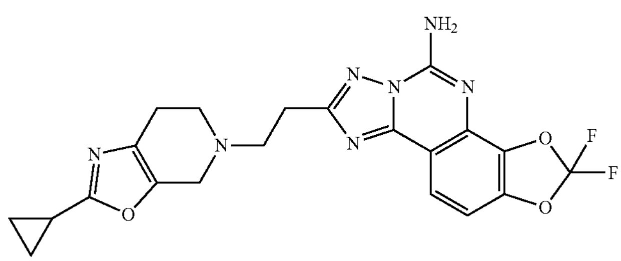 [SMILES: Nc1nc2c3c(ccc2c2nc(CCN4CCc5nc(C6CC6)oc5C4)nn12)OC(F)(F)O3] | 8-[2-(2-cyclopropyl-6,7-dihydro[1,3]oxazolo[5,4-c]pyridin-5(4H)-yl)ethyl]-2,2-difluoro[1,3]dioxolo[4,5-h][1,2,4]triazolo[1,5-c]quinazolin-5-amine | 456 |
| 15 | 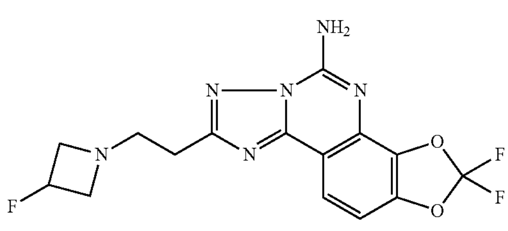 [SMILES: Nc1nc2c3c(ccc2c2nc(CCN4CC(F)C4)nn12)OC(F)(F)O3] | 2,2-difluoro-8-[2-(3-fluoroazetidin-1-yl)ethyl][1,3]dioxolo[4,5-h][1,2,4]triazolo[1,5-c]quinazolin-5-amine | 367 |
| 16 | 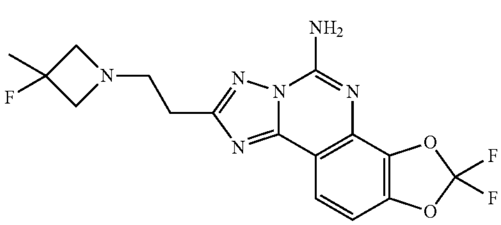 [SMILES: CC1(F)CN(CCc2nc3c4ccc5c(c4nc(N)n3n2)OC(F)(F)O5)C1] | 2,2-difluoro-8-[2-(3-fluoro-3-methylazetidin-1-yl)ethyl][1,3]dioxolo[4,5-h][1,2,4]triazolo[1,5-c]quinazolin-5-amine | 381 |

TABLE 2-continued

| Ex. No. | Structure | IUPAC Name | Exact Mass [M + H]+ |
|---|---|---|---|
| 17 | 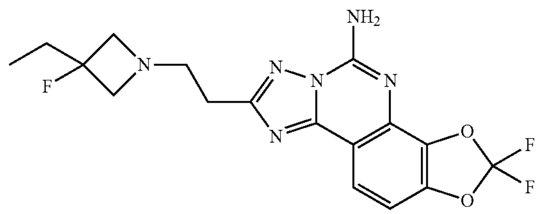 [SMILES: CCC1(F)CN(CCc2nc3c4ccc5c(c4nc(N)n3n2)OC(F)(F)O5)C1] | 8-[2-(3-ethyl-3-fluoroazetidin-1-yl)ethyl]-2,2-difluoro[1,3]dioxolo[4,5-h][1,2,4]triazolo[1,5-c]quinazolin-5-amine | 395 |
| 18 | 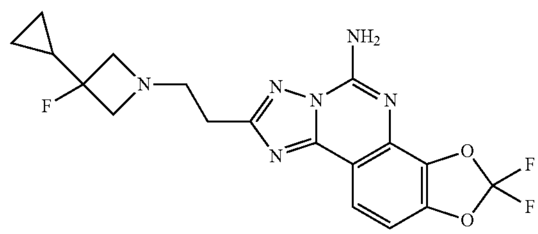 [SMILES: Nc1nc2c3c(ccc2c2nc(CCN4CC(F)(C5CC5)C4)nn12)OC(F)(F)O3] | 8-[2-(3-cyclopropyl-3-fluoroazetidin-1-yl)ethyl]-2,2-difluoro[1,3]dioxolo[4,5-h][1,2,4]triazolo[1,5-c]quinazolin-5-amine | 407 |
| 19 | 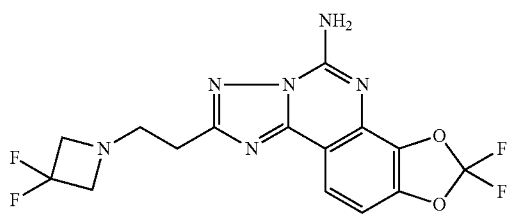 [SMILES: Nc1nc2c3c(ccc2c2nc(CCN4CC(F)(F)C4)nn12)OC(F)(F)O3] | 8-[2-(3,3-difluoroazetidin-1-yl)ethyl]-2,2-difluoro[1,3]dioxolo[4,5-h][1,2,4]triazolo[1,5-c]quinazolin-5-amine | 385 |
| 20 | 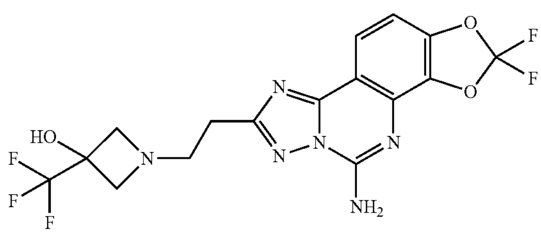 [SMILES: Nc1nc2c3c(ccc2c2nc(CCN4CC(O)(C(F)(F)F)C4)nn12)OC(F)(F)O3] | 1-[2-(5-amino-2,2-difluoro[1,3]diozolo[4,5-h][1,2,4]triazolo[1,5-c]quinazolin-8-yl)ethyl]-3-(trifluoromethyl)azetidin-3-ol | 433 |
| 21 | 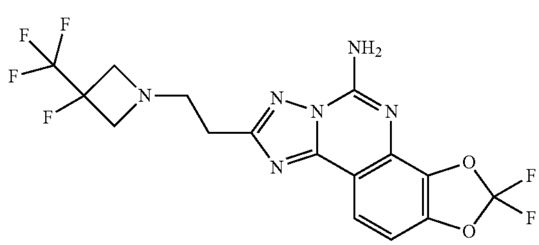 [SMILES: Nc1nc2c3c(ccc2c2nc(CCN4CC(F)(C(F)(F)F)C4)nn12)OC(F)(F)O3] | 2,2-difluoro-8-{2-[3-fluoro-3-(trifluoromethyl)azetidin-1-yl]ethyl}[1,3]dioxolo[4,5-h][1,2,4]triazolo[1,5-c]quinazolin-5-amine | 435 |
| 22 | 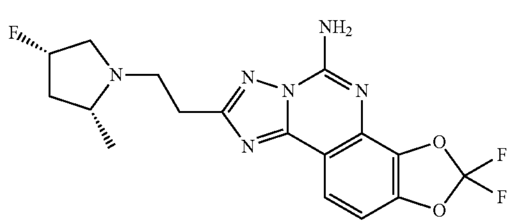 [SMILES: C[C@@H]1C[C@H](F)CN1CCc1nc2c3ccc4c(c3nc(N)n2n1)OC(F)(F)O4] | 2,2-difluoro-8-{2-[(2R,4S)-4-fluoro-2-methylpyrrolidin-1-yl]ethyl}[1,3]dioxolo[4,5-h][1,2,4]triazolo[1,5-c]quinazolin-5-amine | 395 |

TABLE 2-continued

| Ex. No. | Structure | IUPAC Name | Exact Mass [M + H]+ |
|---|---|---|---|
| 23 | 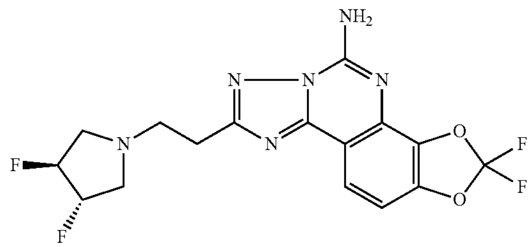 [SMILES: Nc1nc2c3c(ccc2c2nc(CCN4C[C@H](F)[C@@H](F)C4)nn12)OC(F)(F)O3] | 8-{2-[(3S,4S)-3,4-difluoropyrrolidin-1-yl]ethyl}-2,2-difluoro[1,3]dioxolo[4,5-h][1,2,4]triazolo[1,5-c]quinazolin-5-amine | 399 |
| 24 | 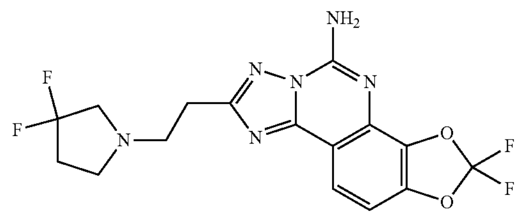 [SMILES: Nc1nc2c3c(ccc2c2nc(CCN4CCC(F)(F)C4)nn12)OC(F)(F)O3] | 8-[2-(3,3-difluoropyrrolidin-1-yl)ethyl]-2,2-difluoro[1,3]dioxolo[4,5-h][1,2,4]triazolo[1,5-c]quinazolin-5-amine | 399 |
| 25 | 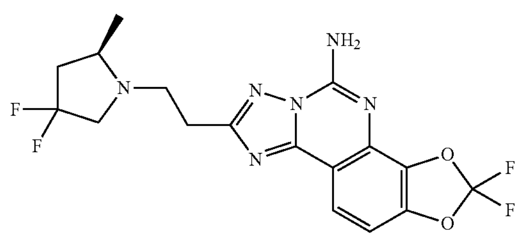 [SMILES: C[C@@H]1CC(F)(F)CN1CCc1nc2c3ccc4c(c3nc(N)n2n1)OC(F)(F)O4] | 8-{2-[(2R)-4,4-difluoro-2-methylpyrrolidin-1-yl]ethyl}-2,2-difluoro[1,3]dioxolo[4,5-h][1,2,4]triazolo[1,5-c+quinazolin-5-amine | 413 |
| 26 | 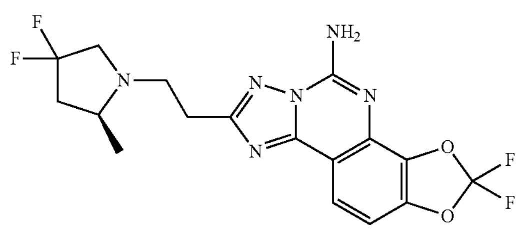 [SMILES: C[C@H]1CC(F)(F)CN1CCc1nc2c3ccc4c(c3nc(N)n2n1)OC(F)(F)O4] | 8-{2-[(2S)-4,4-difluoro-2-methylpyrrolidin-1-yl]ethyl}-2,2-difluoro[1,3]dioxolo[4,5-h][1,2,4]triazolo[1,5-c]quinazolin-5-amine | 413 |
| 27 | 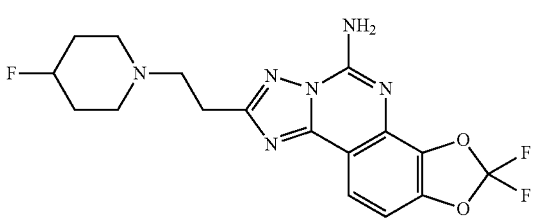 [SMILES: Nc1nc2c3c(ccc2c2nc(CCN4CCC(F)CC4)nn12)OC(F)(F)O3] | 2,2-difluoro-8-[2-(4-fluoropiperidin-1-yl)ethyl][1,3]dioxolo[4,5-h][1,2,4]triazolo[1,5-c]quinazolin-5-amine | 395 |
| 28 | 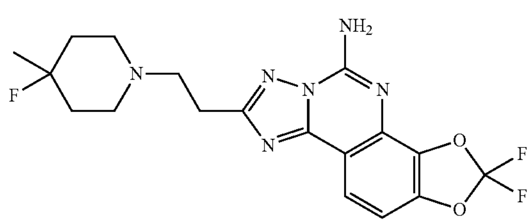 | 2,2-difluoro-8-[2-(4-fluoro-4-methylpiperidin-1-yl)ethyl][1,3]dioxolo[4,5-h][1,2,4]triazolo[1,5-c]quinazolin-5-amine | 409 |

TABLE 2-continued

| Ex. No. | Structure | IUPAC Name | Exact Mass [M + H]+ |
|---|---|---|---|
| 29 | 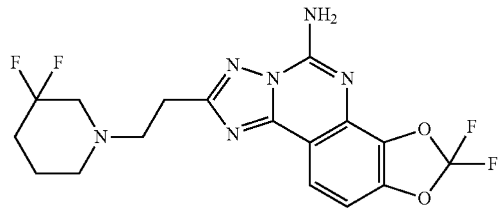 [SMILES: Nc1nc2c3c(ccc2c2nc(CCN4CCCC(F)(F)C4)nn12)OC(F)(F)O3] | 8-[2-(3,3-difluoropiperidin-1-yl)ethyl]-2,2-difluoro[1,3]dioxolo[4,5-h][1,2,4]triazolo[1,5-c]quinazolin-5-amine | 413 |
| 30 | 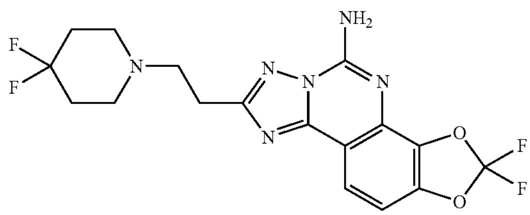 [SMILES: Nc1nc2c3c(ccc2c2nc(CCN4CCC(F)(F)CC4)nn12)OC(F)(F)O3] | 8-[2-(4,4-difluoropiperidin-1-yl)ethyl]-2,2-difluoro[1,3]dioxolo[4,5-h][1,2,4]triazolo[1,5-c]quinazolin-5-amine | 413 |
| 31 | 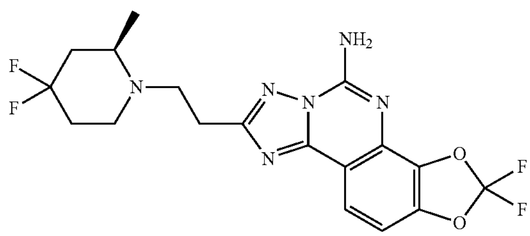 [SMILES: C[C@@H]1CC(F)(F)CCN1CCc1nc2c3ccc4c(c3nc(N)n2n1)OC(F)(F)O4] | 8-{2-[(2R)-4,4-difluoro-2-methylpiperidin-1-yl]ethyl}-2,2-difluoro[1,3]dioxolo[4,5-h][1,2,4]triazolo[1,5-c]quinazolin-5-amine | 427 |
| 32 | 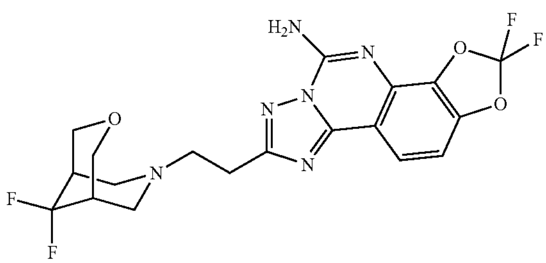 [SMILES: Nc1nc2c3c(ccc2c2nc(CCN4CC5COCC(C4)C5(F)F)nn12)OC(F)(F)O3] | 8-[2-(9,9-difluoro-3-oxa-7-azabicyclo[3.3.1]non-7-yl)ethyl]-2,2-difluoro[1,3]dioxolo[4,5-h][1,2,4]triazolo[1,5-c]quinazolin-5-amine | 455 |
| 33 | 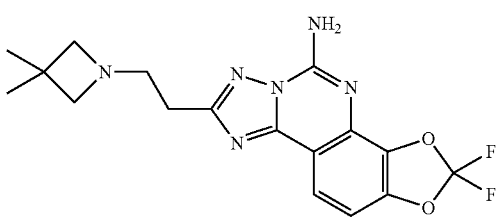 [SMILES: CC1(C)CN(CCc2nc3c4ccc5c(c4nc(N)n3n2)OC(F)(F)O5)C1] | 8-[2-(3,3-dimethylazetidin-1-yl)ethyl]-2,2-difluoro[1,3]dioxolo[4,5-h][1,2,4]triazolo[1,5-c]quinazolin-5-amine | 377 |
| 34 | 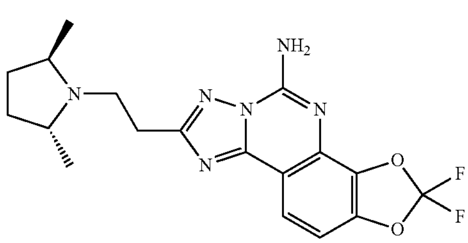 [SMILES: C[C@@H]1CC[C@@H](C)N1CCc1nc2c3ccc4c(c3nc(N)n2n1)OC(F)(F)O4] | 8-{2-[(2R,5R)-2,5-dimethylpyrrolidin-1-yl]ethyl}-2,2-difluoro[1,3]dioxolo[4,5-h][1,2,4]triazolo[1,5-c]quinazolin-5-amine | 391 |

TABLE 2-continued

| Ex. No. | Structure | IUPAC Name | Exact Mass [M + H]+ |
|---|---|---|---|
| 35 | 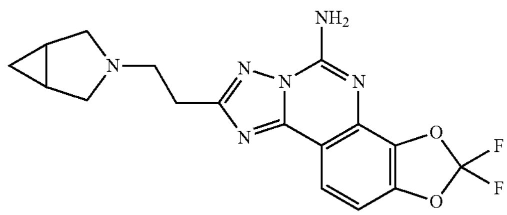 [SMILES: Nc1nc2c3c(ccc2c2nc(CCN4CC5CC5C4)nn12)OC(F)(F)O3] | 8-[2-(3-azabicyclo[3.1.0]hex-3-yl)ethyl]-2,2-difluoro[1,3]dioxolo[4,5-h][1,2,4]triazolo[1,5-c]quinazolin-5-amine | 375 |
| 36 | 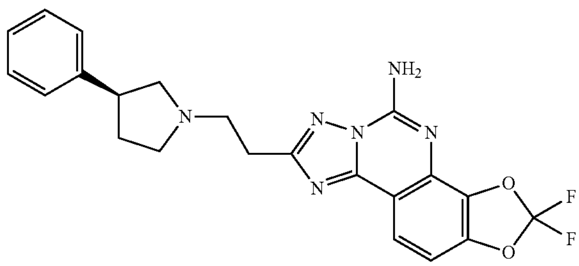 [SMILES: Nc1nc2c3c(ccc2c2nc(CCN4CC[C@@H](c5ccccc5)C4)nn12)OC(F)(F)O3] | 2,2-difluoro-8-{2-[(3S)-3-phenylpyrrolidin-1-yl]ethyl}[1,3]dioxolo[4,5-h][1,2,4]triazolo[1,5-c]quinazolin-5-amine | 439 |
| 37 | 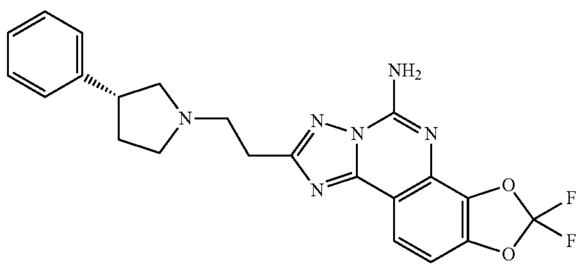 [SMILES: Nc1nc2c3c(ccc2c2nc(CCN4CC[C@H](c5ccccc5)C4)nn12)OC(F)(F)O3] | 2,2-difluoro-8-{2-[(3R)-3-phenylpyrrolidin-1-yl]ethyl}[1,3]dioxolo[4,5-h][1,2,4]triazolo[1,5-c]quinazolin-5-amine | 439 |
| 38 | 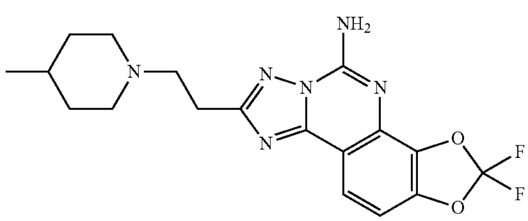 [SMILES: CC1CCN(CCc2nc3c4ccc5c(c4nc(N)n3n2)OC(F)(F)O5)CC1] | 2,2-difluoro-8-[2-(4-methylpiperidin-1-yl)ethyl][1,3]dioxolo[4,5-h][1,2,4]triazolo[1,5-c]quinazolin-5-amine | 391 |
| 39 | 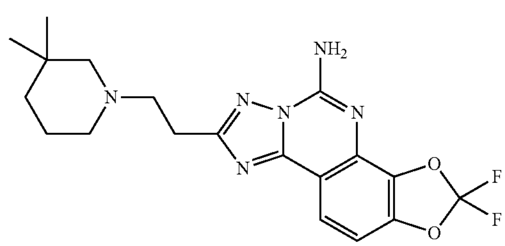 [SMILES: CC1(C)CCCN(CCc2nc3c4ccc5c(c4nc(N)n3n2)OC(F)(F)O5)C1] | 8-[2-(3,3-dimethylpiperidin-1-yl)ethyl]-2,2-difluoro[1,3]dioxolo[4,5-h][1,2,4]triazolo[1,5-c]quinazolin-5-amine | 405 |
| 40 | 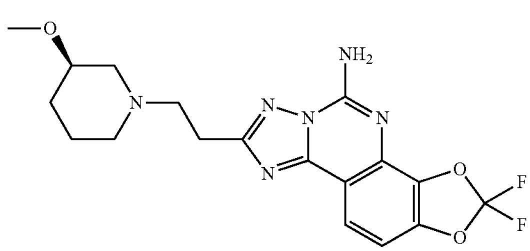 [SMILES: CO[C@@H]1CCCN(CCc2nc3c4ccc5c(c4nc(N)n3n2)OC(F)(F)O5)C1] | 2,2-difluoro-8-{2-[(3R)-3-methoxypiperidin-1-yl]ethyl}[1,3]dioxolo[4,5-h][1,2,4]triazolo[1,5-c]quinazolin-5-amine | 407 |

TABLE 2-continued

| Ex. No. | Structure | IUPAC Name | Exact Mass [M + H]+ |
|---|---|---|---|
| 41 | 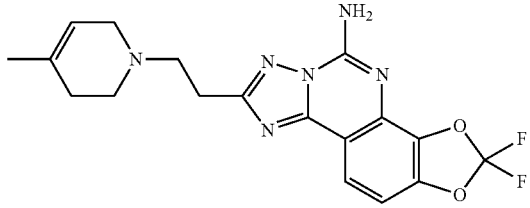 [SMILES: CC1=CCN(CCc2nc3c4ccc5c(c4nc(N)n3n2)OC(F)(F)O5)CC1] | 2,2-difluoro-8-[2-(4-methyl-3,6-dihydropyridin-1(2H)-yl)ethyl][1,3]dioxolo[4,5-h][1,2,4]triazolo[1,5-c]quinazolin-5-amine | 389 |
| 42 | 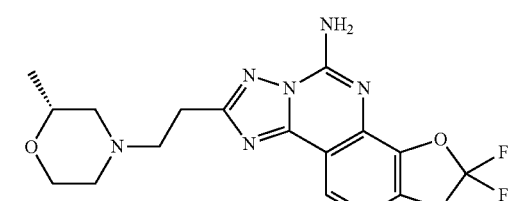 | 2,2-difluoro-8-{2-[(2R)-2-methylmorpholin-4-yl]ethyl}[1,3]dioxolo[4,5-h][1,2,4]triazolo[1,5-c]quinazolin-5-amine | 393 |
| 43 | 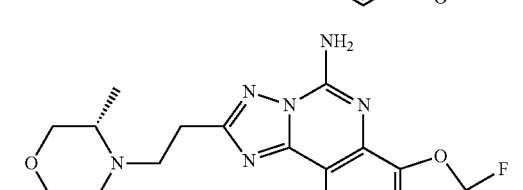 | 2,2-difluoro-8-{2-[(3S)-3-methylmorpholin-4-yl]ethyl}[1,3]dioxolo[4,5-h][1,2,4]triazolo[1,5-c]quinazolin-5-amine | 393 |
| 44 | 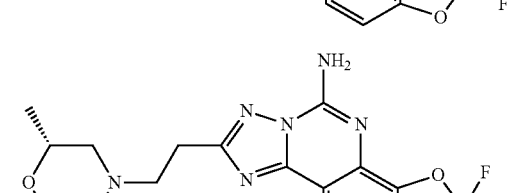 | 8-{2-[(2R,6S)-2,6-dimethylmorpholin-4-yl]ethyl}-2,2-difluoro[1,3]dioxolo[4,5-h][1,2,4]triazolo[1,5-c]quinazolin-5-amine | 407 |
| 45 | 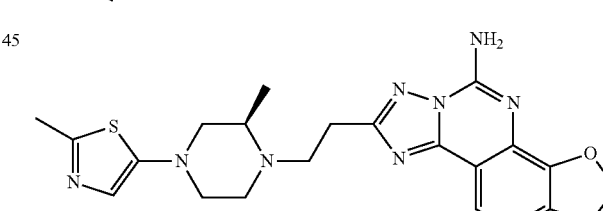 | 2,2-difluoro-8-{2-[(2R)-2-methyl-4-(2-methyl-1,3-thiazol-5-yl)piperazin-1-yl]ethyl}[1,3]dioxolo[4,5-h][1,2,4]triazolo[1,5-c]quinazolin-5-amine | 489 |
| 46 | 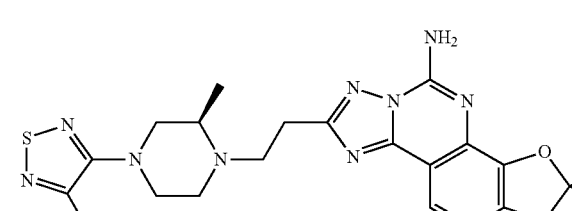 | 8-{2-[(2R)-4-(4-chloro-1,2,5-thiadiazol-3-yl)-2-methylpiperazin-1-yl]ethyl}-2,2-difluoro[1,3]dioxolo[4,5-h][1,2,4]triazolo[1,5-c]quinazolin-5-amine | 510 |
| 47 | 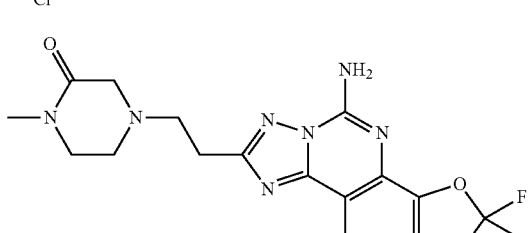 | 4-[2-(5-amino-2,2-difluoro[1,3]dioxolo[4,5-h][1,2,4]triazolo[1,5-c]quinazolin-8-yl)ethyl]-1-methylpiperazin-2-one | 406 |

TABLE 2-continued

| Ex. No. | Structure | IUPAC Name | Exact Mass [M + H]+ |
|---|---|---|---|
| 48 | 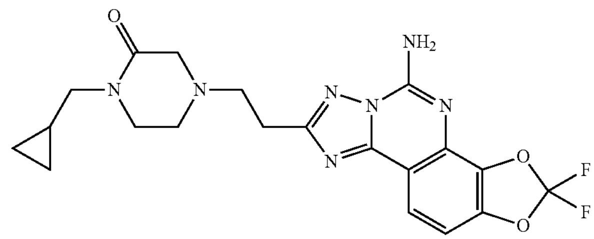 [SMILES: Nc1nc2c3c(ccc2c2nc(CCN4CCN(CC5CC5)C(=O)C4)nn12)OC(F)(F)O3] | 4-[2-(5-amino-2,2-difluoro[1,3]dioxolo[4,5-h][1,2,4]triazolo[1,5-c]quinazolin-8-yl)ethyl]-1-(cyclopropylmethyl)piperazin-2-one | 446 |
| 49 | 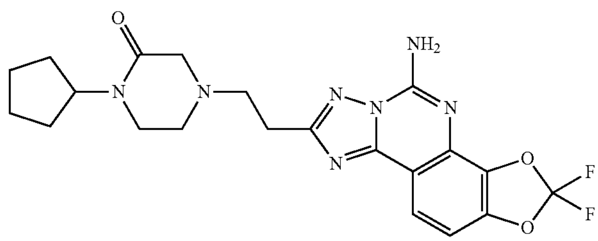 [SMILES: Nc1nc2c3c(ccc2c2nc(CCN4CCN(C5CCCC5)C(=O)C4)nn12)OC(F)(F)O3] | 4-[2-(5-amino-2,2-difluoro[1,3]dioxolo[4,5-h][1,2,4]triazolo[1,5-c]quinazolin-8-yl)ethyl]-1-cyclopentylpiperazin-2-one | 460 |
| 50 | 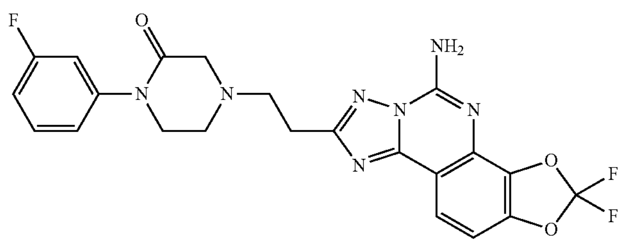 [SMILES: Nc1nc2c3c(ccc2c2nc(CCN4CCN(c5cccc(F)c5)C(=O)C4)nn12)OC(F)(F)O3] | 4-[2-(5-amino-2,2-difluoro[1,3]dioxolo[4,5-h][1,2,4]triazolo[1,5-c]quinazolin-8-yl)ethyl]-1-(3-fluorophenyl)piperazin-2-one | 486 |
| 51 | 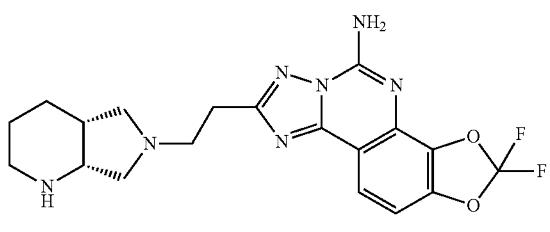 [SMILES: Nc1nc2c3c(ccc2c2nc(CCN4C[C@H]5CCCN[C@H]5C4)nn12)OC(F)(F)O3] | 2,2-difluoro-8-{2-[(4aR,7aR)-octahydro-6H-pyrrolo[3,4-b]pyridin-6-yl]ethyl}[1,3]dioxolo[4,5-h][1,2,4]triazolo[1,5-c]quinazolin-5-amine | 418 |
| 52 | 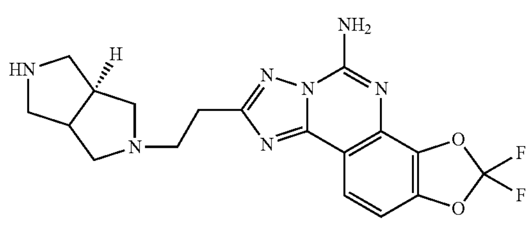 [SMILES: Nc1nc2c3c(ccc2c2nc(CCN4CC5CNC[C@H]5C4)nn12)OC(F)(F)O3] | 2,2-difluoro-8-{2-[(3aS)-hexahydropyrrolo[3,4-c]pyrrol-2(1H)-yl]ethyl}[1,3]dioxolo[4,5-h][1,2,4]triazolo[1,5-c]quinazolin-5-amine | 404 |
| 53 | 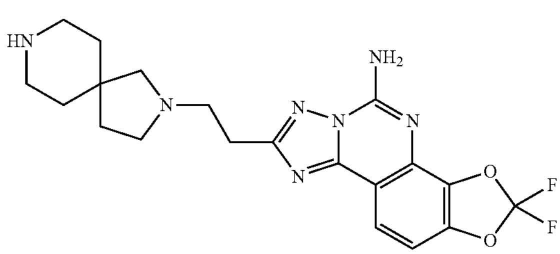 [SMILES: Nc1nc2c3c(ccc2c2nc(CCN4CCC5(CCNCC5)C4)nn12)OC(F)(F)O3] | 8-[2-(2,8-diazaspiro[4.5]dec-2-yl)ethyl]-2,2-difluoro[1,3]dioxolo[4,5-h][1,2,4]triazolo[1,5-c]quinazolin-5-amine | 432 |

TABLE 2-continued

| Ex. No. | Structure | IUPAC Name | Exact Mass [M + H]+ |
|---|---|---|---|
| 54 | 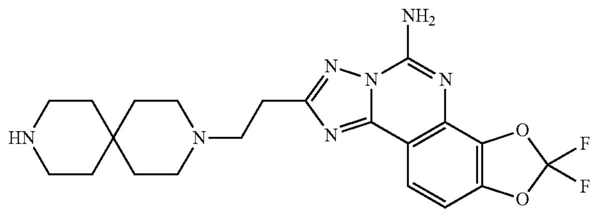 [SMILES: Nc1nc2c3c(ccc2c2nc(CCN4CCC5(CCNCC5)CC4)nn12)OC(F)(F)O3] | 8-[2-(3,9-diazaspiro[5.5]undec-3-yl)ethyl]-2,2-difluoro[1,3]dioxolo[4,5-h][1,2,4]triazolo[1,5-c]quinazolin-5-amine | 446 |
| 55 | 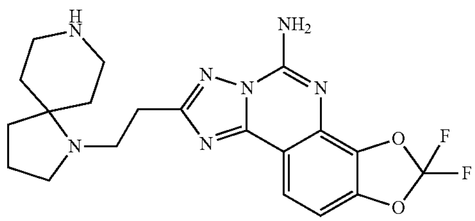 [SMILES: Nc1nc2c3c(ccc2c2nc(CCN4CCCC45CCNCC5)nn12)OC(F)(F)O3] | 8-[2-(1,8-diazaspiro[4.5]dec-1-yl)ethyl]-2,2-difluoro[1,3]dioxolo[4,5-h][1,2,4]triazolo[1,5-c]quinazolin-5-amine | 432 |
| 56 | 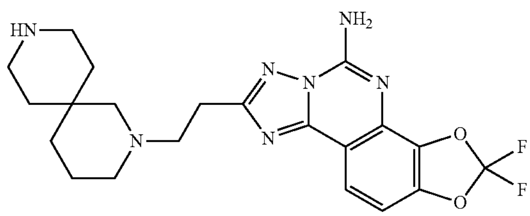 [SMILES: Nc1nc2c3c(ccc2c2nc(CCN4CCCC5(CCNCC5)C4)nn12)OC(F)(F)O3] | 8-[2-(2,9-diazaspiro[5.5]undec-2-yl)ethyl]-2,2-difluoro[1,3]dioxolo[4,5-h][1,2,4]triazolo[1,5-c]quinazolin-5-amine | 446 |
| 57 | 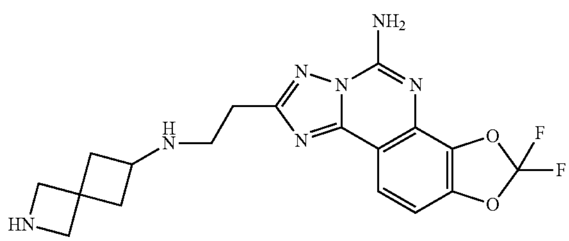 [SMILES: Nc1nc2c3c(ccc2c2nc(CCNC4CC5(CNC5)C4)nn12)OC(F)(F)O3] | 8-[2-(2-azaspiro[3.3]hept-6-ylamino)ethyl]-2,2-difluoro[1,3]dioxolo[4,5-h][1,2,4]triazolo[1,5-c]quinazolin-5-amine | 404 |
| 58 | 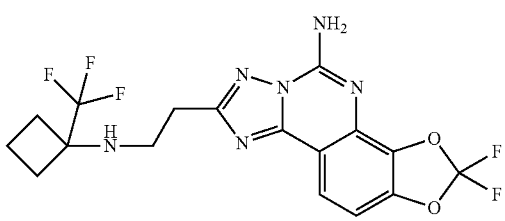 [SMILES: Nc1nc2c3c(ccc2c2nc(CCNC4(C(F)(F)F)CCC4)nn12)OC(F)(F)O3] | 2,2-difluoro-8-(2-{[1-(trifluoromethyl)cyclobutyl]amino}ethyl)[1,3]dioxolo[4,5-h][1,2,4]triazolo[1,5-c]quinazolin-5-amine | 431 |
| 59 | 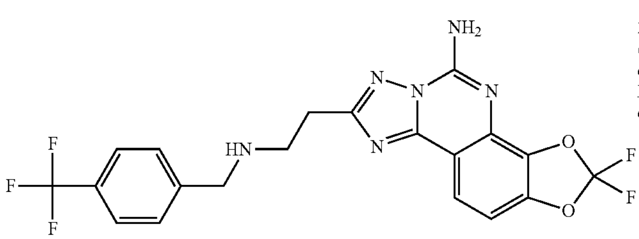 [SMILES: Nc1nc2c3c(ccc2c2nc(CCNCc4ccc(C(F)(F)F)cc4)nn12)OC(F)(F)O3] | 2,2-difluoro-8-(2-{[4-(trifluoromethyl)benzyl]amino}ethyl)[1,3]dioxolo[4,5-h][1,2,4]triazolo[1,5-c]quinazolin-5-amine | 467 |

TABLE 2-continued

| Ex. No. | Structure | IUPAC Name | Exact Mass [M + H]+ |
|---|---|---|---|
| 60 | 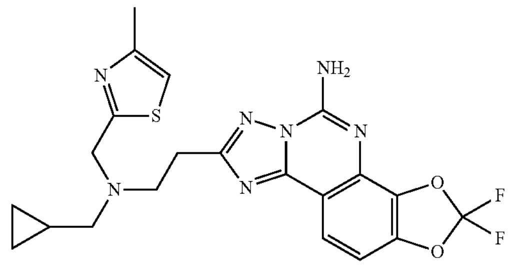 [SMILES: Cc1csc(CN(CCc2nc3c4ccc5c(c4nc(N)n3n2)OC(F)(F)O5)CC2CC2)n1] | 8-(2-{(cyclopropylmethyl)[(4-methyl-1,3-thiazol-2-yl)methyl]amino}ethyl)-2,2-difluoro[1,3]dioxolo[4,5-h][1,2,4]triazolo[1,5-c]quinazolin-5-amine | 474 |
| 61 | 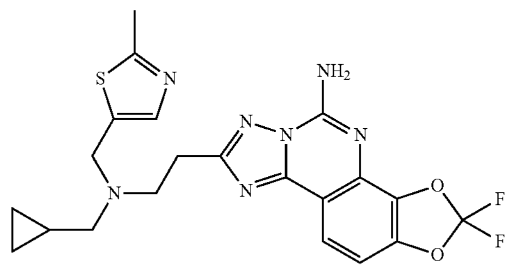 [SMILES: Cc1ncc(CN(CCc2nc3c4ccc5c(c4nc(N)n3n2)OC(F)(F)O5)CC2CC2)s1] | 8-(2-{(cyclopropylmethyl)[(2-methyl-1,3-thiazol-5-yl)methyl]amino}ethyl)-2,2-difluoro[1,3]dioxolo[4,5-h][1,2,4]triazolo[1,5-c]quinazolin-5-amine | 474 |

The compounds in Table 3 were prepared by using methods described in Example 6, substituting the appropriate racemic amine for 6,7-dihydro-5H-pyrrolo[3,4-b]pyridine. If feasible, the racemic products were separated into their enantiomers by chiral HPLC. Where the stereochemistry of a particular stereocenter in an isolated enantiomer is unknown, the stereocenter(s) is designated by an "*"

TABLE 3

| Ex. No. | Structure | IUPAC Name | Exact Mass [M + H]+ |
|---|---|---|---|
| 62 | 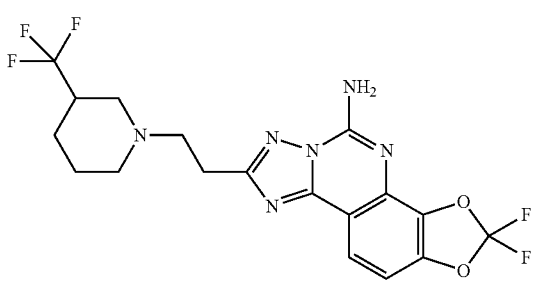 [SMILES: Nc1nc2c3c(ccc2c2nc(CCN4CCCC(C(F)(F)F)C4)nn12)OC(F)(F)O3] | 2,2-difluoro-8-{2-[3-(trifluoromethyl)piperidin-1-yl]ethyl}[1,3]dioxolo[4,5-h][1,2,4]triazolo[1,5-c]quinazolin-5-amine | 445 |
| 63 | 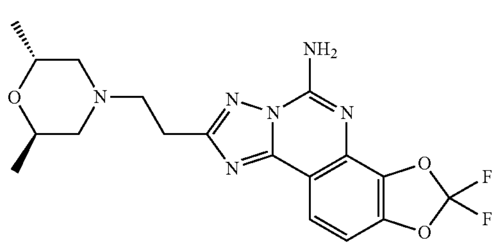 [SMILES: C[C@@H]1CN(CCc2nc3c4ccc5c(c4nc(N)n3n2)OC(F)(F)O5)C[C@@H](C)O1] | 8-{2-[(2R,6R)-2,6-dimethylmorpholin-4-yl]ethyl}-2,2-difluoro[1,3]dioxolo[4,5-h][1,2,4]triazolo[1,5-c]quinazolin-5-amine | 407 |

TABLE 3-continued

| Ex. No. | Structure | IUPAC Name | Exact Mass [M + H]+ |
|---|---|---|---|
| 64 | 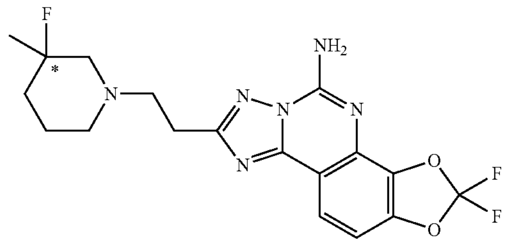 [SMILES: CC1(F)CCCN(CCc2nc3c4ccc5c(c4nc(N)n3n2)OC(F)(F)O5)C1] | (R or S)-2,2-difluoro-8-[2-(3-fluoro-3-methylpiperidin-1-yl)ethyl][1,3]dioxolo[4,5-h][1,2,4]triazolo[1,5-c]quinazolin-5-amine (faster eluting [a]) | 409 |
| 65 | 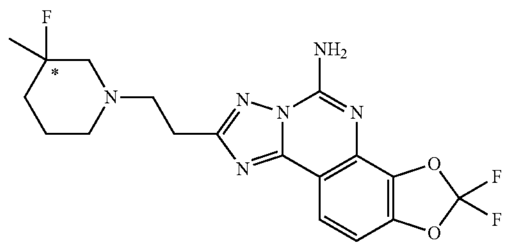 [SMILES: CC1(F)CCCN(CCc2nc3c4ccc5c(c4nc(N)n3n2)OC(F)(F)O5)C1] | (R or S)-2,2-difluoro-8-[2-(3-fluoro-3-methylpiperidin-1-yl)ethyl][1,3]dioxolo[4,5-h][1,2,4]triazolo[1,5-c]quinazolin-5-amine (slower eluting [a]) | 409 |
| 66 | 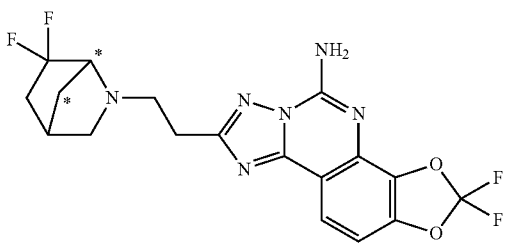 [SMILES: Nc1nc2c3c(ccc2c2nc(CCN4CC5CC4C(F)(F)C5)nn12)OC(F)(F)O3] | (R or S)-8-[2-(6,6-difluoro-2-azabicyclo[2.2.1]hept-2-yl)ethyl]-2,2-difluoro[1,3]dioxolo[4,5-h][1,2,4]triazolo[1,5-c]quinazolin-5-amine (faster eluting [b]) | 425 |
| 67 | 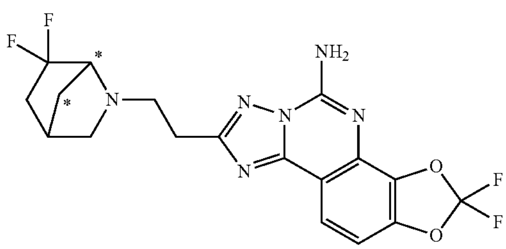 [SMILES: Nc1nc2c3c(ccc2c2nc(CCN4CC5CC4C(F)(F)C5)nn12)OC(F)(F)O3] | (R or S)-8-[2-(6,6-difluoro-2-azabicyclo[2.2.1]hept-2-yl)ethyl]-2,2-difluoro[1,3]dioxolo[4,5-h][1,2,4]triazolo[1,5-c]quinazolin-5-amine (slower eluting [b]) | 425 |
| 68 | 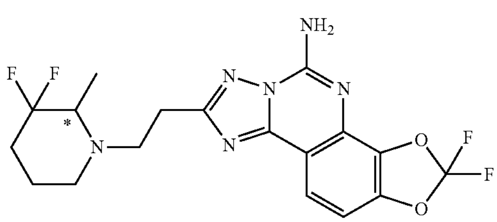 [SMILES: CC1N(CCc2nc3c4ccc5c(c4nc(N)n3n2)OC(F)(F)O5)CCCC1(F)F] | (R or S)-8-[2-(3,3-difluoro-2-methylpiperidin-1-yl)ethyl]-2,2-difluoro[1,3]dioxolo[4,5-h][1,2,4]triazolo[1,5-c]quinazolin-5-amine (faster eluting [c]) | 427 |
| 69 | 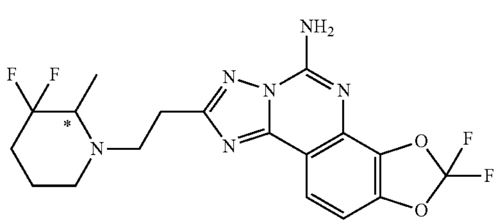 [SMILES: CC1N(CCc2nc3c4ccc5c(c4nc(N)n3n2)OC(F)(F)O5)CCCC1(F)F] | (R or S)-8-[2-(3,3-difluoro-2-methylpiperidin-1-yl)ethyl]-2,2-difluoro[1,3]dioxolo[4,5-h][1,2,4]triazolo[1,5-c]quinazolin-5-amine (slower eluting [c]) | 427 |

[a] HPLC: Chiralpak IC (methanol/supercritical carbon dioxide)
[b] HPLC: Chiralcel OD (methanol/acetonitrile/supercritical carbon dioxide)
[c] HPLC: Chiralcel OJ (isopropanol/supercritical carbon dioxide)

Example 70

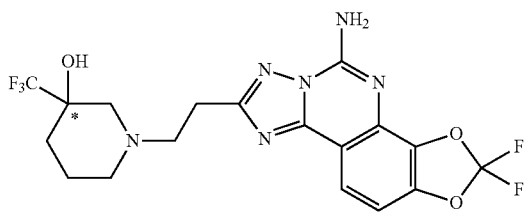 [SMILES: Nc1nc2c3c(ccc2c2nc(CCN4CCCC(O)(C(F)(F)F)C4)nn12)OC(F)(F)O3]

(R or S)-1-(2-(5-amino-2,2-difluoro-[1,3]dioxolo[4,
5-h][1,2,4]triazolo[1,5-c]quinazolin-8-yl)ethyl)-3-
(trifluoromethyl)piperidin-3-ol (faster eluting)

The stereochemistry of the stereocenter designated by an
"*" in this isolated enantiomer is unknown.

Step A: tert-butyl 3-hydroxy-3-(trifluoromethyl) piperidine-1-carboxylate

To a tetrahydrofuran (50 mL) solution of tert-butyl 3-oxopiperidine-1-carboxylate (4.0 g, 20 mmol) at 0° C. was added a tetrahydrofuran (10 mL) solution of trimethyl (trifluoromethyl)silane (3.4 g, 24 mmol, 1.2 equiv.) dropwise. The reaction mixture was stirred for 30 minutes. Tetrabutylammonium fluoride (10 g, 40 mmol, 2.0 equiv.) was added to the reaction mixture, which was stirred at room temperature for 12 hours. Solvent was removed in vacuo, and the residue was redissolved in ethyl acetate. The solution was washed with brine, dried (magnesium sulfate), filtered and concentrated in vacuo to afford the crude product. Chromatography over silica gel, eluting with hexanes/ethyl acetate, afforded the title compound as white solid. Chromatography of the racemic mixture over Chiralpak AD column, eluting with isopropanol/acetonitrile/supercritical carbon dioxide, afforded the separate enantiomers.

Step B: 3-hydroxy-3-(trifluoromethyl)piperidin-1-ium chloride

To a dichloromethane (6.0 mL) solution of the fast enantiomer of tert-butyl 3-hydroxy-3-(trifluoromethyl)piperidine-1-carboxylate (0.54 g, 2.0 mmol) was added a 4 M dioxane solution of hydrochloric acid (3.0 mL, 12 mmol). The reaction mixture was stirred at room temperature for 4 hours. Solvent was removed in vacuo to afford the title compound, which was used in the subsequent step without further purification.

Step C: 1-(2-(5-((2,4-dimethoxybenzyl)amino)-2,2-difluoro-[1,3]dioxolo[4,5-h][1,2,4]triazolo[1,5-c]quinazolin-8-yl)ethyl)-3-(trifluoromethyl)piperidin-3-ol To a mixture of 2-(5-((2,4-dimethoxybenzyl)amino)-2,2-difluoro-[1,3]dioxolo[4,5-h][1,2,4]triazolo[1,5-c]quinazolin-8-yl)ethyl methanesulfonate (0.40 g, 0.75 mmol, EXAMPLE 6 STEP A), 3-hydroxy-3-(trifluoromethyl)piperidin-1-ium chloride prepared in step B (0.23 g, 1.1 mmol), potassium iodide (0.37 g, 2.3 mmol) and potassium carbonate (0.26 g, 1.9 mmol) was charged acetonitrile (10 mL). The reaction mixture was stirred at 80° C. for 4 hours. Solvent was removed in vacuo, and the residue was redissolved in dichloromethane. The organic phase was washed with water, dried (magnesium sulfate), filtered, and concentrated in vacuo to afford a crude product. Chromatography over silica gel, eluting with dichloromethane/methanol, afforded the title compound as a white solid. LC/MS=611 [M+1].

Step D: 1-(2-(5-amino-2,2-difluoro-[1,3]dioxolo[4,5-h][1,2,4]triazolo[1,5-c]quinazolin-8-yl)ethyl)-3-(trifluoromethyl)piperidin-3-ol To 1-(2-(5-((2,4-dimethoxybenzyl)amino)-2,2-difluoro-[1,3]dioxolo[4,5-h][1,2,4]triazolo[1,5-c]quinazolin-8-yl) ethyl)-3-(trifluoromethyl)piperidin-3-ol (0.15 g, 0.25 mmol) was charged trifluoroacetic acid (1.0 mL), and the reaction mixture was stirred at room temperature for 12 hours. Solvent was removed in vacuo, and the residue was redissolved in dichloromethane. The organic phase was washed with aqueous sodium carbonate and concentrated in vacuo to afford a crude product. Purification by reversed-phase HPLC, eluting with acetonitrile/water, afforded the title compound as pale yellow solid. LC/MS=461 [M+1].

Example 71

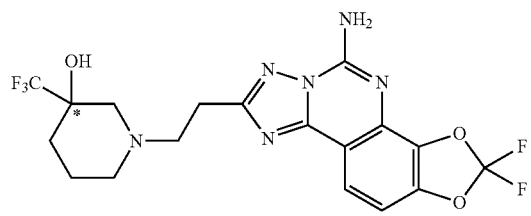 [SMILES: Nc1nc2c3c(ccc2c2nc(CCN4CCCC(O)(C(F)(F)F)C4)nn12)OC(F)(F)O3]

(R or S)-1-(2-(5-amino-2,2-difluoro-[1,3]dioxolo[4,
5-h][1,2,4]triazolo[1,5-c]quinazolin-8-yl)ethyl)-3-
(trifluoromethyl)piperidin-3-ol (slower eluting)

The stereochemistry of the stereocenter designated by an
"*" in this isolated enantiomer is unknown.

EXAMPLE 71, the opposite enantiomer of EXAMPLE 70, was synthesized by following the procedures described in Example 70, substituting the slow enantiomer of tert-butyl 3-hydroxy-3-(trifluoromethyl)piperidine-1-carboxylate for the fast enantiomer of tert-butyl 3-hydroxy-3-(trifluoromethyl)piperidine-1-carboxylate in step B. LC/MS=461 [M+1].

Example 72

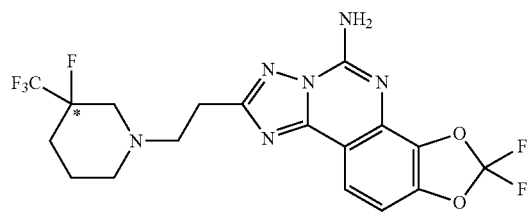 [SMILES: Nc1nc2c3c(ccc2c2nc(CCN4CCCC(F)(C(F)(F)F)C4)nn12)OC(F)(F)O3]

(R or S)-2,2-difluoro-8-(2-(3-fluoro-3-(trifluoromethyl)piperidin-1-yl)ethyl)-[1,3]dioxolo[4,5-h][1,2,4]
triazolo[1,5-c]quinazolin-5-amine (faster eluting)

The stereochemistry of the stereocenter designated by an
"*" in this isolated enantiomer is unknown.

Step A: N-(2,4-dimethoxybenzyl)-2,2-difluoro-8-(2-(3-fluoro-3-(trifluoromethyl)piperidin-1-yl)ethyl)-[1,3]dioxolo[4,5-h][1,2,4]triazolo[1,5-c]quinazolin-5-amine To a stirring dichloromethane (5 mL) solution of 1-(2-(5-((2,4-dimethoxybenzyl)amino)-2,2-difluoro-[1,3]dioxolo[4,5-h][1,2,4]triazolo[1,5-c]quinazolin-8-yl)ethyl)-3-(trifluoromethyl)piperidin-3-ol (0.28 g, 0.46 mmol, EXAMPLE 70, STEP C) at −20° C. was added (diethylamino)sulfur trifluoride (0.073 mL, 0.55 mmol). It was slowly warmed up to room temperature and stirred for 12 hours. The mixture was diluted with dichloromethane and washed with saturated aqueous sodium carbonate solution and brine. The aqueous layer was extracted with dichloromethane, and the combined organic extracts were dried (magnesium sulfate), filtered, and concentrated in vacuo to afford the title compound as yellowish oil. The material will be used in the subsequent reaction without further purification. LC/MS=613 [M+1].

Step B: 2,2-difluoro-8-(2-(3-fluoro-3-(trifluoromethyl)piperidin-1-yl)ethyl)-[1,3]dioxolo[4,5-h][1,2,4]triazolo[1,5-c]quinazolin-5-amine N-(2,4-dimethoxybenzyl)-2,2-difluoro-8-(2-(3-fluoro-3-(trifluoromethyl)piperidin-1-yl)ethyl)-[1,3]dioxolo[4,5-h][1,2,4]triazolo[1,5-c]quinazolin-5-amine (0.25 g, 0.41 mmol, step A) was charged with trifluoroacetic acid (1.0 mL), and the reaction mixture was stirred at 50° C. for 2 hours. Solvent was removed in vacuo, and the residue was redissolved in dichloromethane. The organic phase was washed with aqueous sodium carbonate and concentrated in vacuo to afford a crude product. Purification by reversed-phase HPLC, eluting with acetonitrile/water, afforded the title compound as pale yellow solid. LC/MS=463 [M+1].

Example 73

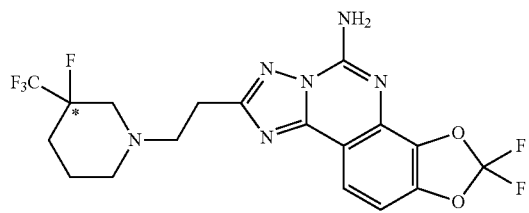 [SMILES: Nc1nc2c3c(ccc2c2nc(CCN4CCCC(F)(C(F)(F)F)C4)nn12)OC(F)(F)O3]

(R or S)-2,2-difluoro-8-(2-(3-fluoro-3-(trifluoromethyl)piperidin-1-yl)ethyl)-[1,3]dioxolo[4,5-h][1,2,4]triazolo[1,5-c]quinazolin-5-amine (slower eluting)

The stereochemistry of the stereocenter designated by an "*" in this isolated enantiomer is unknown.

EXAMPLE 73, the opposite enantiomer of EXAMPLE 72, was synthesized by following the procedures described in example 72, substituting the intermediate 1-(2-(5-((2,4-dimethoxybenzyl)amino)-2,2-difluoro-[1,3]dioxolo[4,5-h][1,2,4]triazolo[1,5-c]quinazolin-8-yl)ethyl)-3-(trifluoromethyl)piperidin-3-ol from EXAMPLE 71 for the intermediate used in EXAMPLE 70. LC/MS=463 [M+1].

Example 74

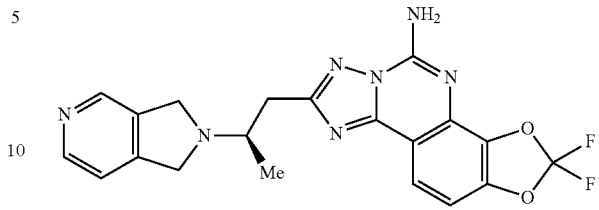

(R)-8-(2-(1H-pyrrolo[3,4-c]pyridin-2(3H)-yl)propyl)-2,2-difluoro-[1,3]dioxolo[4,5-h][1,2,4]triazolo[1,5-c]quinazolin-5-amine

Step A: (S)-1-(5-((2,4-dimethoxybenzyl)amino)-2,2-difluoro-[1,3]dioxolo[4,5-h][1,2,4]triazolo[1,5-c]quinazolin-8-yl)propan-2-yl methanesulfonate To a stirring dichloromethane (100 mL) suspension of (S)-1-(5-((2,4-dimethoxybenzyl)amino)-2,2-difluoro-[1,3]dioxolo[4,5-h][1,2,4]triazolo[1,5-c]quinazolin-8-yl)propan-2-ol (6.6 g, 14 mmol, intermediate 3) at room temperature was added triethylamine (3.9 mL, 28 mmol, 2.0 equiv.), followed by methanesulfonyl chloride (1.5 mL, 19 mmol, 1.4 equiv.). The resulting reaction mixture stirred for 2 hours. It was washed with saturated aqueous sodium hydrogencarbonate, dried (magnesium sulfate), and concentrated in vacuo to afford the title compound as a crude product, which was used in the subsequent reaction without further purification. LC/MS=552 [M+1].

Step B: (S)-1-(5-amino-2,2-difluoro-[1,3]dioxolo[4,5-h][1,2,4]triazolo[1,5-c]quinazolin-8-yl)propan-2-yl methanesulfonate To a stirring dichloromethane (50 mL) solution of (S)-1-(5-((2,4-dimethoxybenzyl)amino)-2,2-difluoro-[1,3]dioxolo[4,5-h][1,2,4]triazolo[1,5-c]quinazolin-8-yl)propan-2-yl methanesulfonate (7.7 g, 14 mmol, step A) at room temperature was added trifluoroacetic acid (5.4 mL, 70 mmol, 5.0 equiv.). The reaction mixture was heated to reflux (40° C.), stirred for 18 hours, and cooled to room temperature. It was diluted with dichloromethane (150 mL) and filtered. The filtrate was washed with 1N sodium hydroxide solution (100 mL), dried (magnesium sulfate), and concentrated in vacuo to afford the title compound as a white solid. LC/MS=402 [M+1].

Step C: (R)-8-(2-(1H-pyrrolo[3,4-c]pyridin-2(3H-y)propyl)-2,2-difluoro-[1,3]dioxol[4,5-h][1,2,4]triazolo[1,5-c]quinazolin-5-amine To an aqueous (0.25 mL) solution of 2,3-dihydro-1H-pyrrolo[3,4-c]pyridine hydrochloride (105 mg, 0.670 mmol) was added N,N-diisopropylethylamine (0.15 mL, 0.86 mmol), and the reaction mixture was heated to 100° C. A dioxane (0.75 mL) solution of (S)-1-(5-amino-2,2-difluoro-[1,3]dioxolo[4,5-h][1,2,4]triazolo[1,5-c]quinazolin-8-yl)propan-2-yl methanesulfonate (54 mg, 0.13 mmol, step B) was added dropwise to the above reaction mixture over 15 minutes. The reaction mixture was stirred at 100° C. for 2 hours. It was cooled to room temperature and filtered by syringe filter. Purification of this crude mixture by reversed-phase HPLC, eluting with acetonitrile/water, afforded the title compound. LC/MS=426 [M+1].

The compounds in Table 4 were prepared by using methods described in Example 74, substituting the appropriate amine for 2,3-dihydro-1H-pyrrolo[3,4-c]pyridine. In cases where diastereomeric mixtures were formed in the final synthetic step, the diastereomeric products were separated into their diastereomers by HPLC. Where the stereochemistry of a particular stereocenter in an isolated diastereomer is unknown, the stereocenter is designated by an "*".

TABLE 5

| Ex. No. | Structure | IUPAC Name | Exact Mass [M + H]+ |
|---|---|---|---|
| 75 | 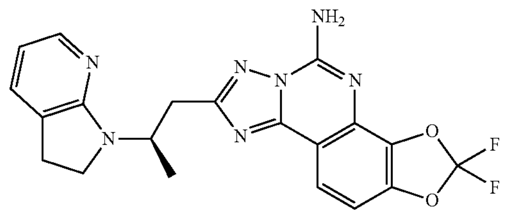 [SMILES: C[C@H](Cc1nc2c3ccc4c(c3nc(N)n2n1)OC(F)(F)O4)N1CCc2cccnc21] | 8-[(2R)-2-(2,3-dihydro-1H-pyrrolo[2,3-b]pyridin-1-yl)propyl]-2,2-difluoro[1,3]dioxolo[4,5-h][1,2,4]triazolo[1,5-c]quinazolin-5-amine | 426 |
| 76 | 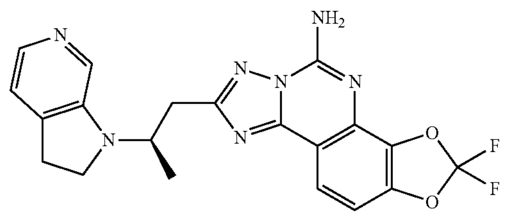 [SMILES: C[C@H](Cc1nc2c3ccc4c(c3nc(N)n2n1)OC(F)(F)O4)N1CCc2ccncc21] | 8-[(2R)-2-(2,3-dihydro-1H-pyrrolo[2,3-c]pyridin-1-yl)propyl]-2,2-difluoro[1,3]dioxolo[4,5-h][1,2,4]triazolo[1,5-c]quinazolin-5-amine | 426 |
| 77 | 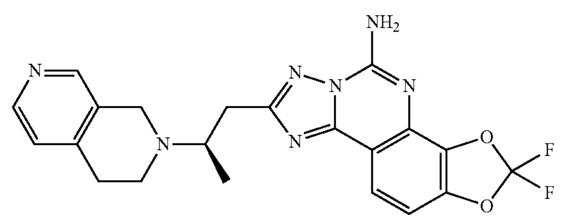 [SMILES: C[C@H](Cc1nc2c3ccc4c(c3nc(N)n2n1)OC(F)(F)O4)N1CCc2ccncc2C1] | 8-[(2R)-2-(3,4-dihydro-2,7-naphthyridin-2(1H)-yl)propyl]-2,2-difluoro[1,3]dioxolo[4,5-h][1,2,4]triazolo[1,5-c]quinazolin-5-amine | 440 |
| 78 | 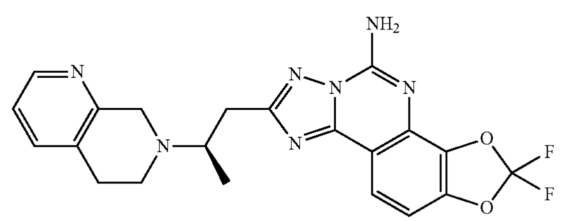 [SMILES: C[C@H](Cc1nc2c3ccc4c(c3nc(N)n2n1)OC(F)(F)O4)N1CCc2cccnc2C1] | 8-[(2R)-2-(5,8-dihydro-1,7-naphthyridin-7(6H)-yl)propyl]-2,2-difluoro[1,3]dioxolo[4,5-h][1,2,4]triazolo[1,5-c]quinazolin-5-amine | 440 |
| 79 | 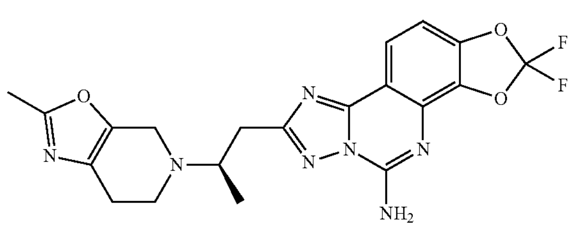 [SMILES: Cc1nc2c(o1)CN([C@H](C)Cc1nc3c4ccc5c(c4nc(N)n3n1)OC(F)(F)O5)CC2] | 2,2-difluoro-8-[(2R)-2-(2-methyl-6,7-dihydro[1,3]oxazolo[5,4-c]pyridine-5(4H)-yl)propyl][1,3]dioxolo[4,5-h][1,2,4]triazolo[1,5-c]quinazolin-5-amine | 444 |
| 80 | 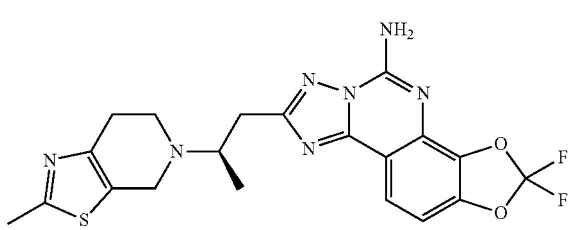 [SMILES: Cc1nc2c(s1)CN([C@H](C)Cc1nc3c4ccc5c(c4nc(N)n3n1)OC(F)(F)O5)CC2] | 2,2-difluoro-8-[(2R)-2-(2-methyl-6,7-dihydro[1,3]thiazolo[5,4-c]pyridin-5(4H)-yl)propyl][1,3]dioxolo[4,5-h][1,2,4]triazolo[1,5-c]quinazolin-5-amine | 460 |

TABLE 5-continued

| Ex. No. | Structure | IUPAC Name | Exact Mass [M + H]+ |
|---|---|---|---|
| 81 | 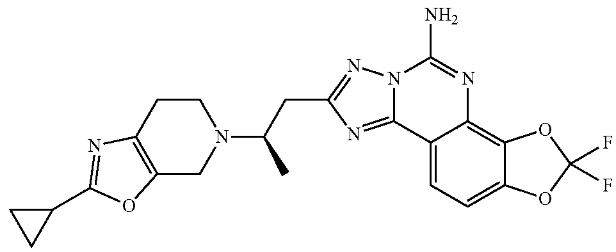 [SMILES: C[C@H](Cc1nc2c3ccc4c(c3nc(N)n2n1)OC(F)(F)O4)N1CCc2nc(C3CC3)oc2C1] | 8-[(2R)-2-(2-cyclopropyl-6,7-dihydro[1,3]oxazolo[5,4-c]pyridin-5(4H)-yl)propyl]-2,2-difluoro[1,3]dioxolo[4,5-h][1,2,4]triazolo[1,5-c]quinazolin-5-amine | 470 |
| 82 | 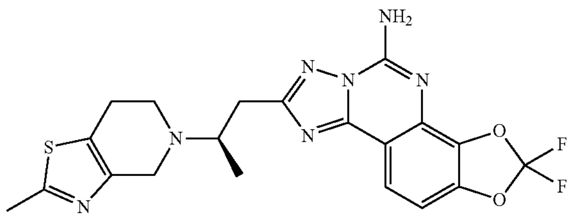 [SMILES: Cc1nc2c(s1)CCN([C@H](C)Cc1nc3c4ccc5c(c4nc(N)n3n1)OC(F)(F)O5)C2] | 2,2-difluoro-8-[(2R)-2-(2-methyl-6,7-dihydro[1,3]thiazolo[4,5-c]pyridin-5(4H)-yl)propyl][1,3]dioxolo[4,5-h][1,2,4]triazolo[1,5-c]quinazolin-5-amine | 460 |
| 83 | 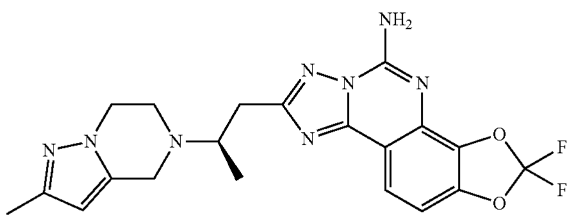 [SMILES: Cc1cc2n(n1)CCN([C@H](C)Cc1nc3c4ccc5c(c4nc(N)n3n1)OC(F)(F)O5)C2] | 2,2-difluoro-8-[(2R)-2-(2-methyl-6,7-dihydropyrazolo[1,5-a]pyrazin-5(4H)-yl)propyl][1,3]dioxolo[4,5-h][1,2,4]triazolo[1,5-c]quinazolin-5-amine | 443 |
| 84 | 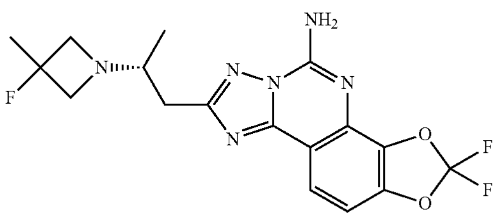 [SMILES: C[C@H](Cc1nc2c3ccc4c(c3nc(N)n2n1)OC(F)(F)O4)N1CC(C)(F)C1] | 2,2-difluoro-8-[(2R)-2-(3-fluoro-3-methylazetidin-1-yl)propyl][1,3]dioxolo[4,5-h][1,2,4]triazolo[1,5-c]quinazolin-5-amine | 395 |
| 85 | 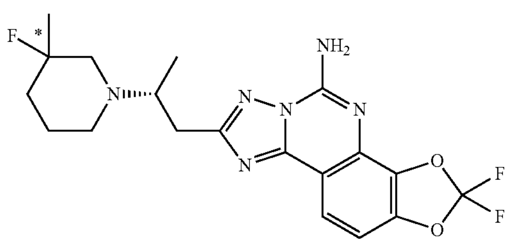 [SMILES: C[C@H](Cc1nc2c3ccc4c(c3nc(N)n2n1)OC(F)(F)O4)N1CCCC(C)(F)C1] | 2,2-difluoro-8-{(2R)-2-[(3R or 3S)-3-fluoro-3-methylpiperidin-1-yl]propyl}[1,3]dioxolo[4,5-h][1,2,4]triazolo[1,5-c]quinazolin-5-amine (faster eluting ᵃ) | 423 |
| 86 | 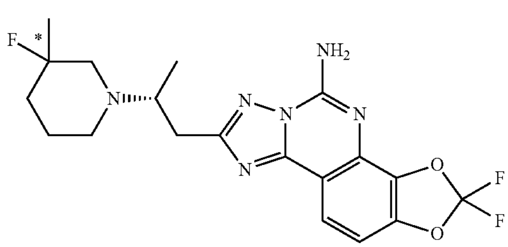 [SMILES: C[C@H](Cc1nc2c3ccc4c(c3nc(N)n2n1)OC(F)(F)O4)N1CCCC(C)(F)C1] | 2,2-difluoro-8-{(2R)-2-[(3R or 3S)-3-fluoro-3-methylpiperidin-1-yl]propyl}[1,3]dioxolo[4,5-h][1,2,4]triazolo[1,5-c]quinazolin-5-amine (slower eluting ᵃ) | 423 |

ᵃ HPLC: Sunfire C18 (acetonitrile/water)

Example 87

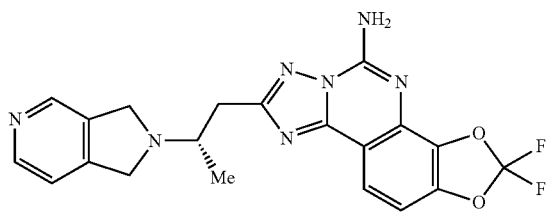 [SMILES: C[C@@H](Cc1nc2c3ccc4c(c3nc(N)n2n1)OC(F)(F)O4)N1Cc2ccncc2C1]

(S)-8-(2-(1H-pyrrolo[3,4-c]pyridin-2(3H)-yl)propyl)-2,2-difluoro-[1,3]dioxolo[4,5-h][1,2,4]triazolo[1,5-c]quinazolin-5-amine The title compound was synthesized by following the procedures described in EXAMPLE 74, substituting (R)-1-(5-((2,4-dimethoxybenzyl)amino)-2,2-difluoro-[1,3]dioxolo[4,5-h][1,2,4]triazolo[1,5-c]quinazolin-8-yl)propan-2-yl methanesulfonate for (S)-1-(5-((2,4-dimethoxybenzyl)amino)-2,2-difluoro-[1,3]dioxolo[4,5-h][1,2,4]triazolo[1,5-c]quinazolin-8-yl)propan-2-yl methanesulfonate in step A. LC/MS=426 [M+1].

The compounds in Table 5 were prepared by using methods described in Example 87, substituting the appropriate amine for 2,3-dihydro-1H-pyrrolo[3,4-c]pyridine. Where the stereochemistry of a particular stereocenter in an isolated diastereomer is unknown, the stereocenter is designated by an "*".

TABLE 5

| Ex. No. | Structure | IUPAC Name | Exact Mass [M + H]+ |
|---|---|---|---|
| 88 | 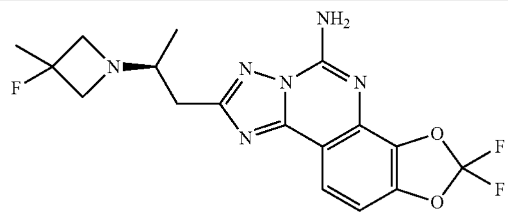 [SMILES: C[C@@H](Cc1nc2c3ccc4c(c3nc(N)n2n1)OC(F)(F)O4)N1CC(C)(F)C1] | 2,2-difluoro-8-[(2S)-2-(3-fluoro-3-methylazetidin-1-yl)propyl][1,3]dioxolo[4,5-h][1,2,4]triazolo[1,5-c]quinazolin-5-amine | 395 |
| 89 | 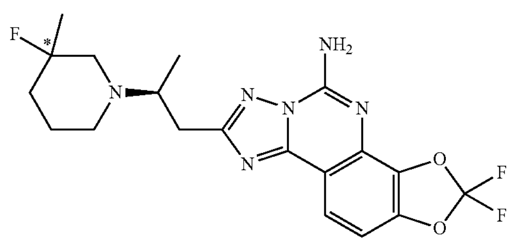 [SMILES: C[C@@H](Cc1nc2c3ccc4c(c3nc(N)n2n1)OC(F)(F)O4)N1CCCC(C)(F)C1] | 2,2-difluoro-8-{(2S)-2-[(3R or 3S)-3-fluoro-3-methylpiperidin-1-yl]propyl}[1,3] dioxolo[4,5-h][1,2,4]triazolo[1,5-c]quinazolin-5-amine (faster eluting $^a$) | 423 |
| 90 | 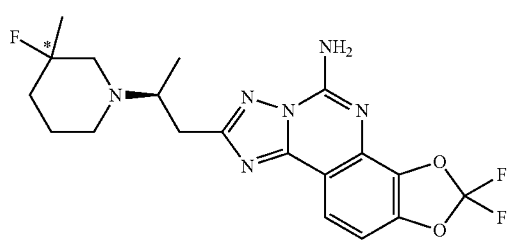 [SMILES: C[C@@H](Cc1nc2c3ccc4c(c3nc(N)n2n1)OC(F)(F)O4)N1CCCC(C)(F)C1] | 2,2-difluoro-8-{(2S)-2-[(3R or 3S)-3-fluoro-3-methylpiperidin-1-yl]propyl}[1,3] dioxolo[4,5-h][1,2,4]triazolo[1,5-c]quinazolin-5-amine (slower eluting $^a$) | 423 |

$^a$ HPLC: Sunfire C18 (acetonitrile/water)

The compounds in Table 6 were prepared by using methods described in Example 74, substituting (±)-1-(5-((2,4-dimethoxybenzyl)amino)-2,2-difluoro-[1,3]dioxolo[4,5-h][1,2,4]triazolo[1,5-c]quinazolin-8-yl)propan-2-yl methanesulfonate for (S)-1-(5-((2,4-dimethoxybenzyl)amino)-2,2-difluoro-[1,3]dioxolo[4,5-h][1,2,4]triazolo[1,5-c]quinazolin-8-yl)propan-2-yl methanesulfonate in step A and the appropriate amine for 2,3-dihydro-1H-pyrrolo[3,4-c]pyridine in step C. The racemic products were then separated into their enantiomers by chiral HPLC. Where the stereochemistry of a particular stereocenter in an isolated enantiomer is unknown, the stereocenter is designated by an "*".

TABLE 6

| Ex. No. | Structure | IUPAC Name | Exact Mass [M + H]+ |
|---|---|---|---|
| 91 | 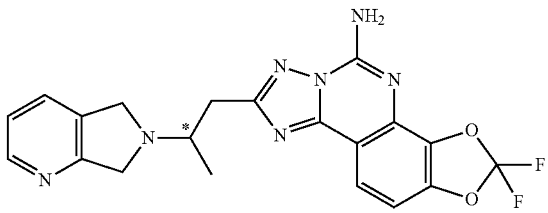 [SMILES: CC(Cc1nc2c3ccc4c(c3nc(N)n2n1)OC(F)(F)O4)N1Cc2cccnc2C1] | 8-[(2R or 2S)-2-(5,7-dihydro-6H-pyrrolo[3,4-b]pyridin-6-yl)propyl]-2,2-difluoro[1,3]dioxolo[4,5-h][1,2,4]triazolo[1,5-c]quinazolin-5-amine (faster eluting [a]) | 426 |
| 92 | 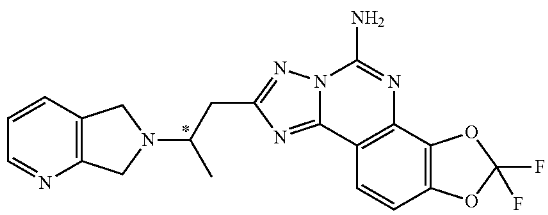 [SMILES: CC(Cc1nc2c3ccc4c(c3nc(N)n2n1)OC(F)(F)O4)N1Cc2cccnc2C1] | 8-[(2R or 2S)-2-(5,7-dihydro-6H-pyrrolo[3,4-b]pyridin-6-yl)propyl]-2,2-difluoro[1,3]dioxolo[4,5-h][1,2,4]triazolo[1,5-c]quinazolin-5-amine (slower eluting [a]) | 426 |
| 93 | 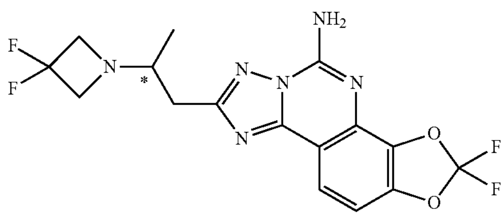 [SMILES: CC(Cc1nc2c3ccc4c(c3nc(N)n2n1)OC(F)(F)O4)N1CC(F)(F)C1] | (R or S)-8-[2-(3,3-difluoroazetidin-1-yl)propyl]-2,2-difluoro[1,3]dioxolo[4,5-h][1,2,4]triazolo[1,5-c]quinazolin-5-amine (faster eluting [b]) | 399 |
| 94 | 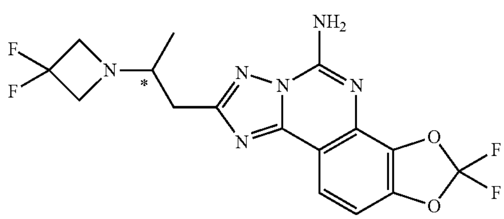 [SMILES: CC(Cc1nc2c3ccc4c(c3nc(N)n2n1)OC(F)(F)O4)N1CC(F)(F)C1] | (R or S)-8-[2-(3,3-difluoroazetidin-1-yl)propyl]-2,2-difluoro[1,3]dioxolo[4,5-h][1,2,4]triazolo[1,5-c]quinazolin-5-amine (slower eluting [b]) | 399 |
| 95 | 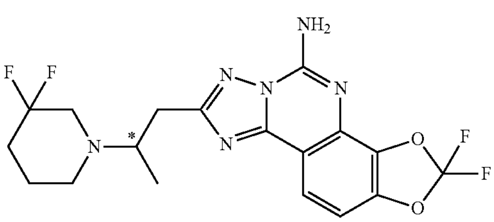 [SMILES: CC(Cc1nc2c3ccc4c(c3nc(N)n2n1)OC(F)(F)O4)N1CCCC(F)(F)C1] | (R or S)-8-[2-(3,3-difluoropiperidin-1-yl)propyl]-2,2-difluoro[1,3]dioxolo[4,5-h][1,2,4]triazolo[1,5-c]quinazolin-5-amine (faster eluting [c]) | 427 |
| 96 | 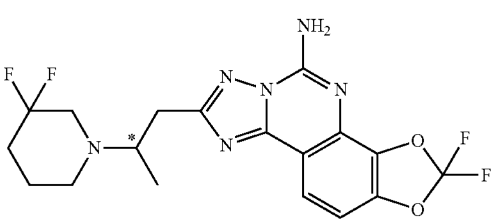 [SMILES: CC(Cc1nc2c3ccc4c(c3nc(N)n2n1)OC(F)(F)O4)N1CCCC(F)(F)C1] | (R or S)-8-[2-(3,3-difluoropiperidin-1-yl)propyl]-2,2-difluoro[1,3]dioxolo[4,5-h][1,2,4]triazolo[1,5-c]quinazolin-5-amine (slower eluting [c]) | 427 |

[a] HPLC: Chiralpak AD-H (methanol/supercritical carbon dioxide)
[b] HPLC: Chiralcel OJ-H (methanol/supercritical carbon dioxide)
[c] HPLC: Lux Cellulose-4 (methanol/supercritical carbon dioxide)

Example 97

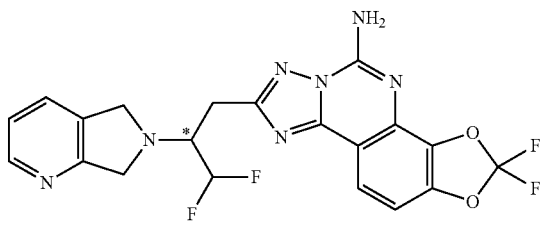 [SMILES: Nc1nc2c3c(ccc2c2nc(CC(C(F)F)N4Cc5cccnc5C4)nn12)OC(F)(F)O3]

(R or S)-8-(3,3-difluoro-2-(5H-pyrrolo[3,4-b]pyridin-6(7H)-yl)propyl)-2,2-difluoro-[1,3]dioxolo[4,5-h][1,2,4]triazolo[1,5-c]quinazolin-5-amine (faster eluting)

The stereochemistry of the stereocenter designated by an "*" in this isolated enantiomer is unknown.

Step A: (±)-ethyl 4,4-difluoro-3-(5H-pyrrolo[3,4-b]pyridin-6(7H)-yl)butanoate

To an acetonitrile (17.5 mL) solution of 6,7-dihydro-5H-pyrrolo[3,4-b]pyridine (525 mg, 4.37 mmol) was added 1,8-diazabicyclo[5.4.0]undec-7-ene (329 μL, 2.19 mmol, 0.5 equiv.), followed by ethyl 4,4-difluorobut-2-enoate (984 mg, 6.55 mmol, 1.5 equiv.). The reaction mixture was stirred at reflux for 12 hours. Concentration in vacuo afforded the title compound as the crude product, which was used in the subsequent reaction without further purification. LC/MS=271 [M+1].

Step B: (±)-4,4-difluoro-3-(5H-pyrrolo[3,4-b]pyridin-6(7H-yl)butanehydrazide

To an ethanolic (22 mL) solution of (±)-ethyl 4,4-difluoro-3-(5H-pyrrolo[3,4-b]pyridin-6(7H)-yl)butanoate (1.18 g, 4.37 mmol, step A) was added hydrazine hydrate (1.49 mL, 30.6 mmol, 7.0 equiv.). The reaction mixture was heated to reflux for 7 hours. Concentration in vacuo (~70° C., ~7 mmHg) afforded the title compound as the crude product, which was used in the subsequent reaction without further purification. LC/MS=257 [M+1].

Step C: (±)-8-(3,3-difluoro-2-(5H-pyrrolo[3,4-b]pyridin-6(7H)-yl)propyl)-2,2-difluoro-[1,3]dioxolo[4,5-h][1,2,4]triazolo[1,5-c]quinazolin-5-amine The title compound was synthesized by following the procedures described from step B through step E in example 3, substituting (±)-4,4-difluoro-3-(5H-pyrrolo[3,4-b]pyridin-6(7H)-yl)butanehydrazide for 2-(2-chloropyridin-3-yl)acetohydrazide. LC/MS=462 [M+1].

Step D: 8-(3,3-difluoro-2-(5H-pyrrolo[3,4-b]pyridin-6(7H)-yl)propyl)-2,2-difluoro-[1,3]dioxolo[4,5-h][1,2,4]triazolo[1,5-c]quinazolin-5-amine The fast enantiomer of the title compound was obtained by chiral HPLC separation of the racemic compound (Chiralpak AS, 20% methanol/supercritical carbon dioxide).

Example 98

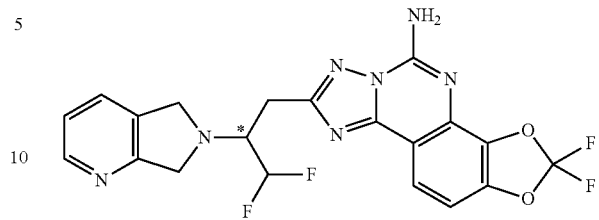

(R or S)-8-(3,3-difluoro-2-(5H-pyrrolo[3,4-b]pyridin-6(7H)-yl)propyl)-2,2-difluoro-[1,3]dioxolo[4,5-h][1,2,4]triazolo[1,5-c]quinazolin-5-amine (slower eluting)

The stereochemistry of the stereocenter designated by an "*" in this isolated enantiomer is unknown.

The opposite enantiomer of EXAMPLE 97 was obtained as the slow enantiomer in the chiral separation as described in EXAMPLE 97, STEP D.

Example 99

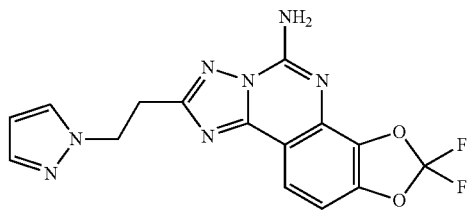 [SMILES: Nc1nc2c3c(ccc2c2nc(CCn4cccn4)nn12)OC(F)(F)O3]

8-(2-(1H-pyrazol-1-yl)ethyl)-2,2-difluoro-[1,3]dioxolo[4,5-h][1,2,4]triazolo[1,5-c]quinazolin-5-amine The title compound was synthesized by following the procedures described in EXAMPLE 97, substituting pyrazole for 6,7-dihydro-5H-pyrrolo[3,4-b]pyridine and ethyl acrylate for ethyl 4,4-difluorobut-2-enoate in step A. LC/MS=360 [M+1].

Example 100

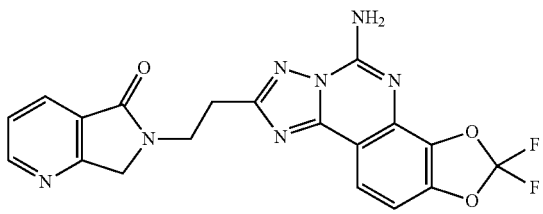 [SMILES: Nc1nc2c3c(ccc2c2nc(CCN4Cc5ncccc5C4=O)nn12)OC(F)(F)O3]

6-(2-(5-amino-2,2-difluoro-[1,3]dioxolo[4,5-h][1,2,4]triazolo[1,5-c]quinazolin-8-yl)ethyl)-6,7-dihydro-5H-pyrrolo[3,4-b]pyridin-5-one Step A: ethyl 3-(5-oxo-5H-pyrrolo[3,4-b]pyridin-6(7H)-yl)propanoate To a stirring methanol (47 mL) solution of β-alanine ethyl ester hydrochloride (2.36 g, 15.4 mmol) was added triethylamine (10.7 mL, 77.0 mmol, 5.0 equiv.), followed by 2-(bromomethyl)-3-(ethoxycarbonyl)pyridinium bromide (5.00 g, 15.4 mmol, 1.0 equiv.). The reaction mixture was heated to reflux for 4 hours and concentrated in vacuo to afford the crude product. Chromatography over silica gel, eluting with methanol/ethyl acetate, afforded the title compound. $^1$H NMR (499 MHz, CDCl$_3$, 6): 1.25 (t, J=7.1 Hz, 3H), 2.75 (t, J=6.6 Hz, 2H), 3.95 (t, J=6.6 Hz, 2H), 4.53 (s, 2H), 7.40 (dd, J=5.0, 7.7 Hz, 1H), 8.11 (d, J=7.7 Hz, 1H), 8.73 (d, J=5.0 Hz, 1H).

Step B: 6-(2-(5-amino-2,2-difluoro-[1,3]dioxolo[4,5-h][1,2,4]triazolo[1,5-c]quinazolin-8-yl)ethyl)-6,7-dihydro-5H-pyrrolo[3,4-b]pyridin-5-one The title compound was synthesized by following the procedures described in EXAMPLE 97, steps B and C, substituting ethyl 3-(5-oxo-5H-pyrrolo[3,4-b]pyridin-6(7H)-yl)propanoate for (±)-ethyl 4,4-difluoro-3-(5H-pyrrolo[3,4-b]pyridin-6(7H)-yl)butanoate in step B. LC/MS=376 [M+1].

Example 101

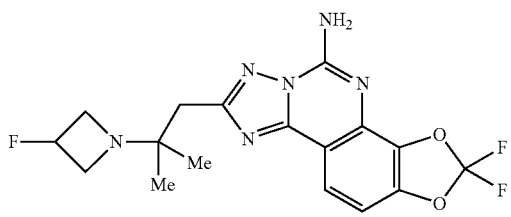 [SMILES: CC(C)(Cc1nc2c3ccc4c(c3nc(N)n2n1)OC(F)(F)O4)N1CC(F)C1]

2,2-difluoro-8-(2-(3-fluoroazetidin-1-yl)-2-methylpropyl)-[1,3]dioxolo[4,5-h][1,2,4]triazolo[1,5-c]quinazolin-5-amine Step A: ethyl 3-(3-hydroxyazetidin-1-yl)-3-methylbutanoate To an acetonitrile (55 mL) suspension of the hydrochloride salt of ethyl 3-amino-3-methylbutanoate (5.00 g, 27.5 mmol) was added potassium carbonate (3.80 g, 27.5 mmol, 1.0 equiv.), followed by 2-(chloromethyl)oxirane (4.31 mL, 55.0 mmol, 1.0 equiv.). After 60 hours, the reaction mixture was filtered and concentrated in vacuo. Chromatography over silica gel, eluting with methanol/ethyl acetate, afforded the title compound as a clear oil. LC/MS=202 [M+1].

Step B: 1-(1-(5-((2,4-dimethoxybenzyl)amino)-2,2-difluoro-[1,3]dioxolo[4,5-h][1,2,4]triazolo[1,5-c]quinazolin-8-yl)-2-methylpropan-2-yl)azetidin-3-ol The title compound was synthesized by following the procedures described in EXAMPLE 3, steps A through D, substituting ethyl 3-(3-hydroxyazetidin-1-yl)-3-methylbutanoate for ethyl 2-(2-chloropyridin-3-yl)acetate in step A. LC/MS=543 [M+1].

Step C: N-(2,4-dimethoxybenzyl)-2,2-difluoro-8-(2-(3-fluoroazetidin-1-yl)-2-methylpropyl)-[1,3]dioxolo[4,5-h][1,2,4]triazolo[1,5-c]quinazolin-5-amine To a stirring dichloromethane (8.1 mL) solution of 1-(1-(5-((2,4-dimethoxybenzyl)amino)-2,2-difluoro-[1,3]dioxolo[4,5-h][1,2,4]triazolo[1,5-c]quinazolin-8-yl)-2-methylpropan-2-yl)azetidin-3-ol (220 mg, 0.41 mmol) was added (diethylamino)sulfur trifluoride (55 µL, 0.42 mmol, 1.0 equiv.) dropwise at room temperature. The reaction mixture was stirred at room temperature for 12 hours and concentrated in vacuo to afford the crude product. Chromatography over silica gel, eluting with methanol/ethyl acetate, afforded the title compound. LC/MS=545 [M+1].

Step D: 2,2-difluoro-8-(2-(3-fluoroazetidin-1-yl)-2-methylpropyl)-[1,3]dioxolo[4,5-h][1,2,4]triazolo[1,5-c]quinazolin-5-amine The title compound was synthesized by following the procedure described in EXAMPLE 3, step E, substituting N-(2,4-dimethoxybenzyl)-2,2-difluoro-8-(2-(3-fluoroazetidin-1-yl)-2-methylpropyl)-[1,3]dioxolo[4,5-h][1,2,4]triazolo[1,5-c]quinazolin-5-amine for 8-((2-chloropyridin-3-yl)methyl)-N-(2,4-dimethoxybenzyl)-2,2-difluoro-[1,3]dioxolo[4,5-h][1,2,4]triazolo[1,5-c]quinazolin-5-amine. LC/MS=395 [M+1].

Example 102

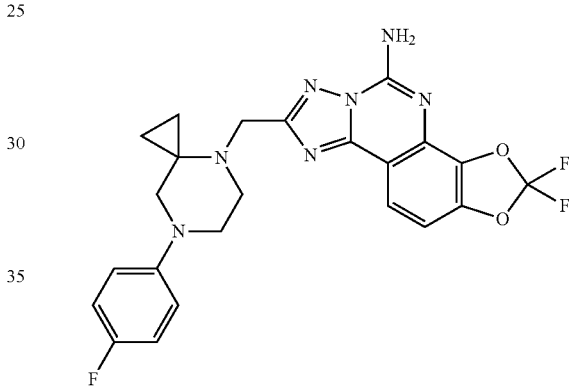

2,2-difluoro-8-((7-(4-fluorophenyl)-4,7-diazaspiro[2.5]octan-4-yl)methyl)-[1,3]dioxolo[4,5-h][1,2,4]triazolo[1,5-c]quinazolin-5-amine Step A: (5-amino-2,2-difluoro-[1,3]dioxolo[4,5-h][1,2,4]triazolo[1,5-c]quinazolin-8-yl)methanol In a round-bottom flask, (5-((2,4-dimethoxybenzyl)amino)-2,2-difluoro-[1,3]dioxolo[4,5-h][1,2,4]triazolo[1,5-c]quinazolin-8-yl)methanol (1.2 g, 2.7 mmol, INTERMEDIATE 5) was charged with trifluoroacetic acid (9.0 mL) at room temperature. The reaction mixture was stirred at 50° C. for 2 hours. After the reaction mixture was cooled down to room temperature, it was concentrated in vacuo to remove the trifluoroacetic acid, and saturated aqueous sodium hydrogencarbonate was added. The white precipitate thus obtained was washed with water and dichloromethane, and dried in vacuo to afford the title compound. LC/MS=296 [M+1].

Step B: 8-(chloromethyl)-2,2-difluoro-[1,3]dioxolo[4,5-h][1,2,4]triazolo[1,5-c]quinazolin-5-amine hydrochloride A mixture of (5-amino-2,2-difluoro-[1,3]dioxolo[4,5-h][1,2,4]triazolo[1,5-c]quinazolin-8-yl)methanol (800 mg, 2.7 mmol, STEP A) and thionyl chloride (4.0 mL, 54 mmol, 20 equiv.) was heated at 65° C. for 5 hours. The thionyl chloride was then distilled off at 60° C., and the crude material was cooled to room temperature. Diethyl ether was added, and the pale yellow precipitate thus generated was washed with more diethyl ether and dried in vacuo to afford the title compound. LC/MS=314 [M+1].

Step C: tert-butyl 7-(4-fluorophenyl)-4,7-diazaspiro[2.5]octane-4-carboxylate

In a microwave tube at room temperature, a toluene (2.6 mL) solution of tert-butyl 4,7-diazaspiro[2.5]octane-4-carboxylate (110 mg, 0.52 mmol) was charged with 1-bromo-4-fluorobenzene (181 mg, 1.0 mmol, 2.0 equiv.), tris(dibenzylideneacetone) dipalladium-chloroform adduct (16 mg, 0.016 mmol, 0.03 equiv.), 2-dicyclohexylphosphino-2',6'-diisopropoxybiphenyl (15 mg, 0.031 mmol, 0.06 equiv.) and potassium tert-butoxide (145 mg, 1.30 mmol, 2.5 equiv.). The microwave tube was sealed and heated to 110° C. for 12 hours. After the reaction mixture was cooled down to room temperature, it was concentrated in vacuo. The residue was redissolved in ethyl acetate, and the organic layer was washed with water, dried (magnesium sulfate), filtered and concentrated in vacuo to afford the crude product. Chromatography over silica gel, eluting with ethyl acetate/hexanes, afforded the title compound. LC/MS=307 [M+1].

Step D: 7-(4-fluorophenyl)-4,7-diazaspiro[2.5]octane hydrochloride

In a round-bottom flask at room temperature, tert-butyl 7-(4-fluorophenyl)-4,7-diazaspiro[2.5]octane-4-carboxylate (150 mg, 0.50 mmol, STEP C) was charged with 4N hydrochloric acid (1.25 mL, 5.0 mmol, 10 equiv.). The reaction mixture was stirred at room temperature for 12 hours. It was then concentrated in vacuo to afford the title compound, which was used in the subsequent step without further purification. LC/MS=207 [M+1].

Step E: 2,2-difluoro-8-((7-(4-fluorophenyl)-4,7-diazaspiro[2.5]octan-4-yl)methyl)-[1,3]dioxolo[4,5-h][1,2,4]triazolo[1,5-c]quinazolin-5-amine To a N,N-dimethylformamide (2.9 mL) suspension of 8-(chloromethyl)-2,2-difluoro-[1,3]dioxolo[4,5-h][1,2,4]triazolo[1,5-c]quinazolin-5-amine hydrochloride (100 mg, 0.29 mmol, STEP B) at room temperature was added 7-(4-fluorophenyl)-4,7-diazaspiro[2.5]octane hydrochloride (100 mg, 0.43 mmol, 1.5 equiv., STEP D), N,N-diisopropylethylamine (150 µL, 0.86 mmol, 3.0 equiv.) and potassium iodide (47 mg, 0.29 mmol, 1.0 equiv.). The reaction mixture was heated to 70° C. for 12 hours. After it was cooled down to room temperature, it was charged with saturated aqueous sodium hydrogencarbonate and extracted with ethyl acetate. The combined organic extracts were dried (magnesium sulfate) and concentrated in vacuo to afford a crude product. Chromatography over silica gel, eluting with ethyl acetate/hexanes afforded the title compound. LC/MS=484[M+1].

The compounds in Table 7 were prepared by using methods described in Example 102, substituting the appropriate Boc-protected piperazine for tert-butyl 4,7-diazaspiro[2.5]octane-4-carboxylate and the appropriate heteroaryl halide for 1-bromo-4-fluorobenzene in step C.

TABLE 7

| Ex. No. | Structure | IUPAC Name | Exact Mass [M + H]+ |
|---|---|---|---|
| 103 | 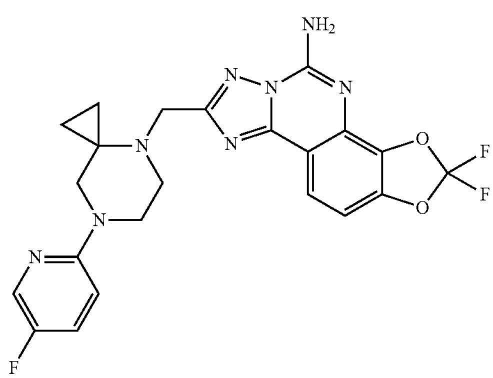 [SMILES: Nc1nc2c3c(ccc2c2nc(CN4CCN(c5ccc(F)cn5)CC45CC5)nn12)OC(F)(F)O3] | 2,2-difluoro-8-{[7-(5-fluoropyridin-2-yl)-4,7-diazaspiro[2.5]oct-4-yl]methyl}[1,3]dioxolo[4,5-h][1,2,4]triazolo[1,5-c]quinazolin-5-amine | 485 |
| 104 | 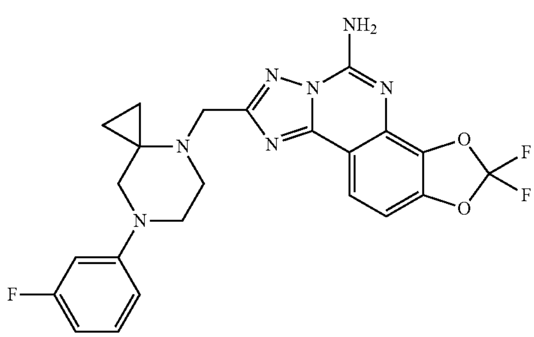 [SMILES: Nc1nc2c3c(ccc2c2nc(CN4CCN(c5cccc(F)c5)CC45CC5)nn12)OC(F)(F)O3] | 2,2-difluoro-8-{[7-(3-fluorophenyl)-4,7-diazaspiro[2.5]oct-4-yl]methyl}[1,3]dioxolo[4,5-h][1,2,4]triazolo[1,5-c]quinazolin-5-amine | 484 |

TABLE 7-continued

| Ex. No. | Structure | IUPAC Name | Exact Mass [M + H]+ |
|---|---|---|---|
| 105 | 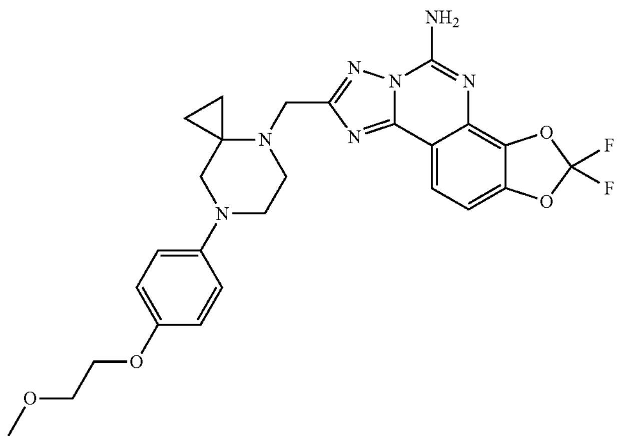 [SMILES: COCCOc1ccc(N2CCN(Cc3nc4c5ccc6c(c5nc(N)n4n3)OC(F)(F)O6)C3(CC3)C2)cc1] | 2,2-difluoro-8-({7-[4-(2-methoxyethoxy)phenyl]-4,7-diazaspiro[2.5]oct-4-yl}methyl)[1,3]dioxolo[4,5-h][1,2,4]triazolo[1,5-c]quinazolin-5-amine | 540 |
| 106 | 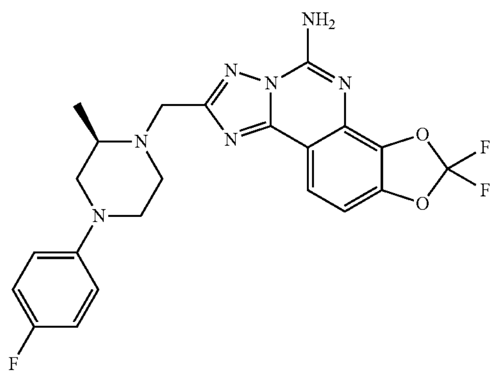 [SMILES: C[C@@H]1CN(c2ccc(F)cc2)CCN1Cc1nc2c3ccc4c(c3nc(N)n2n1)OC(F)(F)O4] | 2,2-difluoro-8-{[(2R)-4-(4-fluorophenyl)-2-methylpiperazin-1-yl]methyl}[1,3]dioxolo[4,5-h][1,2,4]triazolo[1,5-c]quinazolin-5-amine | 472 |
| 107 | 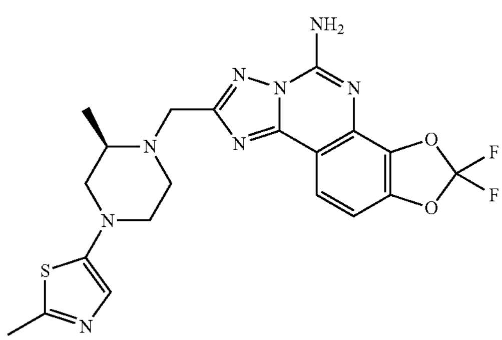 [SMILES: Cc1ncc(N2CCN(Cc3nc4c5ccc6c(c5nc(N)n4n3)OC(F)(F)O6)[C@H](C)C2)s1] | 2,2-difluoro-8-{[(2R)-2-methyl-4-(2-methyl-1,3-thiazol-5-yl)piperazin-1-yl]methyl}[1,3]dioxolo[4,5-h][1,2,4]triazolo[1,5-c]quinazolin-5-amine | 475 |
| 108 | 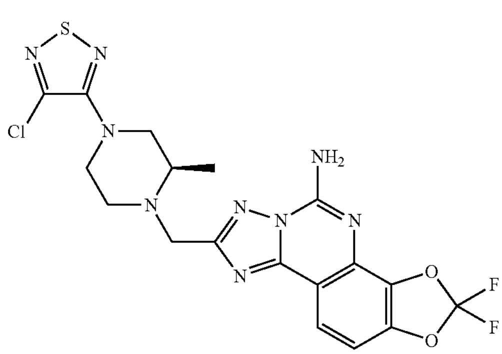 [SMILES: C[C@@H]1CN(c2nsnc2Cl)CCN1Cc1nc2c3ccc4c(c3nc(N)n2n1)OC(F)(F)O4] | 8-{[(2R)-4-(4-chloro-1,2,5-thiadiazol-3-yl)-2-methylpiperazin-1-yl]methyl}-2,2-difluoro[1,3]dioxolo[4,5-h][1,2,4]triazolo[1,5-c]quinazolin-5-amine | 496 |

Example 109

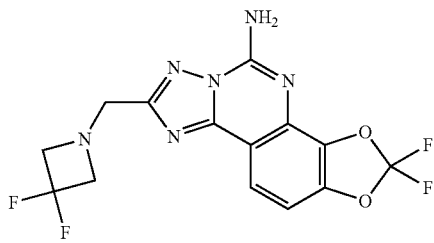 [SMILES: Nc1nc2c3c(ccc2c2nc(CN4CC(F)(F)C4)nn12)OC(F)(F)O3]

8-((3,3-difluoroazetidin-1-yl)methyl)-2,2-difluoro-[1,3]dioxolo[4,5-h][1,2,4]triazolo[1,5-c]quinazolin-5-amine

Step A: (5-((2,4-dimethoxybenzyl)amino)-2,2-difluoro-[1,3]dioxolo[4,5-h][1,2,4]triazolo[1,5-c]quinazolin-8-yl)methyl methanesulfonate To a dichloromethane (5 mL) solution of (5-((2,4-dimethoxybenzyl)amino)-2,2-difluoro-[1,3]dioxolo[4,5-h][1,2,4]triazolo[1,5-c]quinazolin-8-yl)methanol (200 mg, 0.454 mmol, INTERMEDIATE 5) and N,N-diisopropylethylamine (0.16 mL, 0.92 mmol, 2.0 equiv.) was added methanesulfonyl chloride (42 µL, 0.54 mmol, 1.2 equiv.). The reaction mixture was stirred at room temperature for 1 hour, washed with water and brine, dried (sodium sulfate) and concentrated in vacuo to afford the title compound. LC/MS=523 [M+1].

Step B: 8-(chloromethyl)-N-(2,4-dimethoxybenzyl)-2,2-difluoro-[1,3]dioxolo[4,5-h][1,2,4]triazolo[1,5-c]quinazolin-5-amine To an acetone (5 mL) solution of (5-((2,4-dimethoxybenzyl)amino)-2,2-difluoro-[1,3]dioxolo[4,5-h][1,2,4]triazolo[1,5-c]quinazolin-8-yl)methyl methanesulfonate (182 mg, 0.348 mmol, STEP A) was added lithium chloride (73.7 mg, 1.74 mmol, 5.0 equiv.). The reaction was refluxed for 4 hours, concentrated in vacuo, and redissolved in dichloromethane. The organic layer was washed with saturated aqueous sodium hydrogencarbonate, dried (magnesium sulfate), and concentrated in vacuo to afford the title compound, which was used in the subsequent step without further purification. LC/MS=464 [M+1].

Step C: 8-((3,3-difluoroazetidin-1-yl)methyl)-N-(2,4-dimethoxybenzyl)-2,2-difluoro-[1,3]dioxolo[4,5-h][1,2,4]triazolo[1,5-c]quinazolin-5-amine To a dioxane (5 mL) solution of 8-(chloromethyl)-N-(2,4-dimethoxybenzyl)-2,2-difluoro-[1,3]dioxolo[4,5-h][1,2,4]triazolo[1,5-c]quinazolin-5-amine (120 mg, 0.26 mmol, STEP B), 3,3-difluoroazetidine hydrochloride (41 mg, 0.32 mmol), cesium carbonate (270 mg, 0.84 mmol), and potassium iodide (50 mg, 0.301 mmol) was added water (0.5 mL). The reaction mixture was heated to 100° C. for 24 hours, forming a homogeneous solution. It was cooled to room temperature, diluted with water, and extracted with ethyl acetate twice. The combined organic extracts were washed with brine, dried (potassium carbonate), and concentrated in vacuo to afford a crude product. Chromatography over silica gel, eluting with ethyl acetate/hexanes, afforded the title compound. LC/MS=521 [M+1].

Step D: 8-((3,3-difluoroazetidin-1-yl)methyl)-2,2-difluoro-[1,3]dioxolo[4,5-h][1,2,4]triazolo[1,5-c]quinazolin-5-amine To 8-((3,3-difluoroazetidin-1-yl)methyl)-N-(2,4-dimethoxybenzyl)-2,2-difluoro-[1,3]dioxolo[4,5-h][1,2,4]triazolo[1,5-c]quinazolin-5-amine (92.6 mg, 0.178 mmol, STEP C) was charged trifluoroacetic acid (4 mL). The reaction mixture was heated at 50° C. for 12 hours. Solvent was then removed in vacuo, and the residue was charged with a 2N methanol solution of ammonia, forming a white precipitate. The filtrate was concentrated in vacuo to afford a crude product. Chromatography over silica gel, eluting with ethyl acetate/hexanes, afforded the title compound. LC/MS=371 [M+1].

The compounds in Table 8 were prepared by using methods described in Example 109, substituting the appropriate amine for 3,3-difluoroazetidine in step C.

TABLE 8

| Ex. No. | Structure | IUPAC Name | Exact Mass [M + H]+ |
|---|---|---|---|
| 110 | 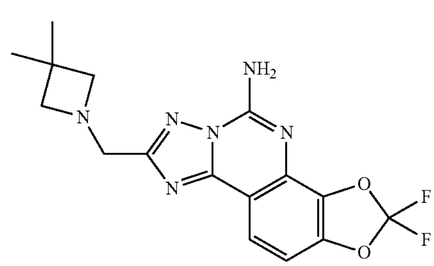 [SMILES: CC1(C)CN(Cc2nc3c4ccc5c(c4nc(N)n3n2)OC(F)(F)O5)C1] | 8-[(3,3-dimethylazetidin-1-yl)methyl]-2,2-difluoro[1,3]dioxolo[4,5-h][1,2,4]triazolo[1,5-c]quinazolin-5-amine | 363 |

TABLE 8-continued

| Ex. No. | Structure | IUPAC Name | Exact Mass [M + H]+ |
|---|---|---|---|
| 111 | 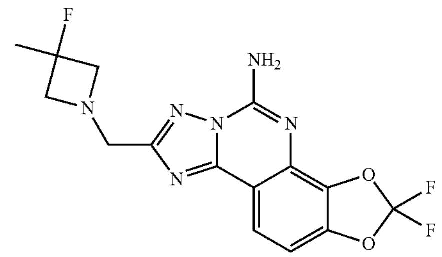 [SMILES: CC1(F)CN(Cc2nc3c4ccc5c(c4nc(N)n3n2)OC(F)(F)O5)C1] | 2,2-difluoro-8-[(3-fluoro-3-methylazetidin-1-yl)methyl][1,3]dioxolo[4,5-h][1,2,4]triazolo[1,5-c]quinazolin-5-amine | 367 |
| 112 | 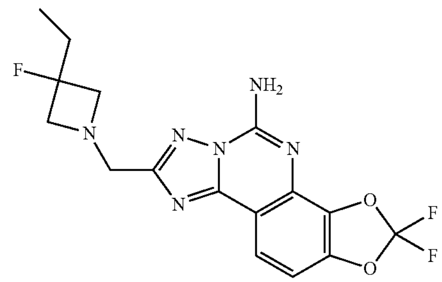 [SMILES: CCC1(F)CN(Cc2nc3c4ccc5c(c4nc(N)n3n2)OC(F)(F)O5)C1] | 8-[(3-ethyl-3-fluoroazetidin-1-yl)methyl]-2,2-difluoro[1,3]dioxolo[4,5-h][1,2,4]triazolo[1,5-c]quinazolin-5-amine | 381 |
| 113 | 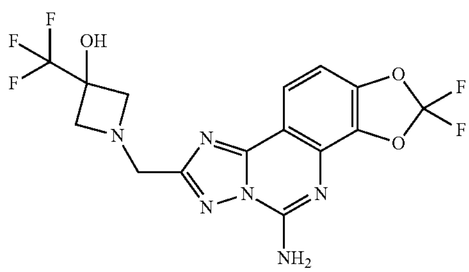 [SMILES: Nc1nc2c3c(ccc2c2nc(CN4CC(O)(C(F)(F)F)C4)nn12)OC(F)(F)O3] | 11-[(5-amino-2,2-difluoro[1,3]dioxolo[4,5-h][1,2,4]triazolo[1,5-c]quinazolin-8-yl)methyl]-3-(trifluoromethyl)azetidin-3-ol | 419 |
| 114 | 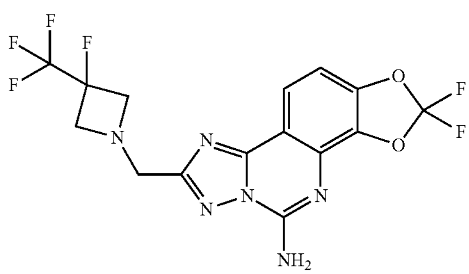 [SMILES: Nc1nc2c3c(ccc2c2nc(CN4CC(F)(C(F)(F)F)C4)nn12)OC(F)(F)O3] | 2,2-difluoro-8-{[3-fluoro-3-(trifluoromethyl)azetidin-1-yl]methyl}[1,3]dioxolo[4,5-h][1,2,4]triazolo[1,5-c]quinazolin-5-amine | 421 |
| 115 | 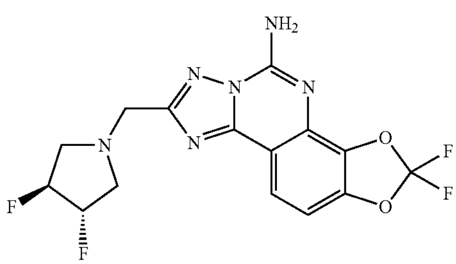 [SMILES: Nc1nc2c3c(ccc2c2nc(CN4C[C@H](F)[C@@H](F)C4)nn12)OC(F)(F)O3] | 8-{[(3S,4S)-3,4-difluoropyrrolidin-1-yl]methyl}-2,2-difluoro[1,3]dioxolo[4,5-h][1,2,4]triazolo[1,5-c]quinazolin-5-amine | 385 |
| 116 | 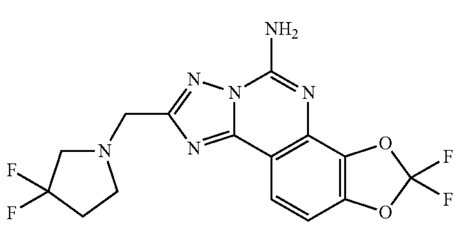 [SMILES: Nc1nc2c3c(ccc2c2nc(CN4CCC(F)(F)C4)nn12)OC(F)(F)O3] | 8-[(3,3-difluoropyrrolidin-1-yl)methyl]-2,2-difluoro[1,3]dioxolo[4,5-h][1,2,4]triazolo[1,5-c]quinazolin-5-amine | 385 |

TABLE 8-continued

| Ex. No. | Structure | IUPAC Name | Exact Mass [M + H]+ |
|---|---|---|---|
| 117 | 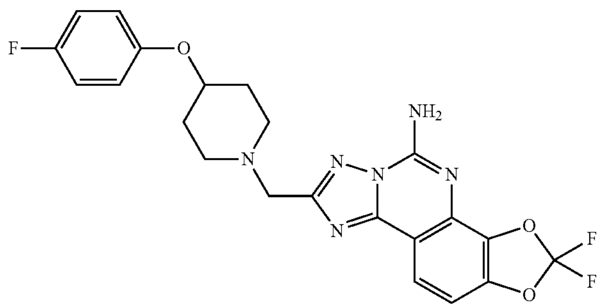 [SMILES: Nc1nc2c3c(ccc2c2nc(CN4CCC(Oc5ccc(F)cc5)CC4)nn12)OC(F)(F)O3] | 2,2-difluoro-8-{[4-(4-fluorophenoxy) piperidin-1-yl]methyl}[1,3]dioxolo [4,5-h][1,2,4]triazolo[1,5-c]quinazolin-5-amine | 473 |
| 118 | 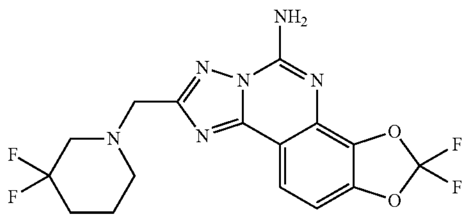 [SMILES: Nc1nc2c3c(ccc2c2nc(CN4CCCC(F)(F)C4)nn12)OC(F)(F)O3] | 8-[(3,3-difluoropiperidin-1-yl)methyl]-2,2-difluoro[1,3]dioxolo[4,5-h][1,2,4]triazolo[1,5-c]quinazolin-5-amine | 399 |
| 119 | 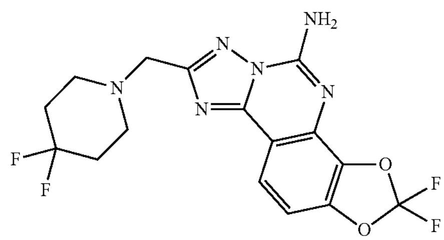 [SMILES: Nc1nc2c3c(ccc2c2nc(CN4CCC(F)(F)CC4)nn12)OC(F)(F)O3] | 8-[(4,4-difluoropiperidin-1-yl)methyl]-2,2-difluoro[1,3]dioxolo[4,5-h][1,2,4]triazolo[1,5-c]quinazolin-5-amine | 399 |
| 120 | 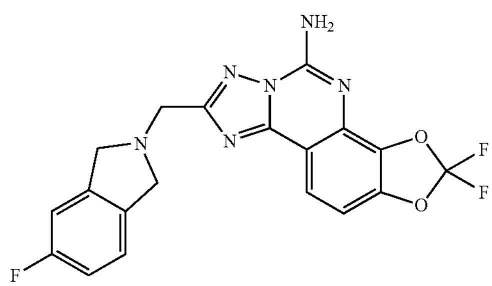 [SMILES: Nc1nc2c3c(ccc2c2nc(CN4Cc5ccc(F)cc5C4)nn12)OC(F)(F)O3] | 2,2-difluoro-8-[(5-fluoro-1,3-dihydro-2H-isoindol-2-yl)methyl][1,3]dioxolo[4,5-h][1,2,4]triazolo[1,5-c]quinazolin-5-amine | 415 |
| 121 | 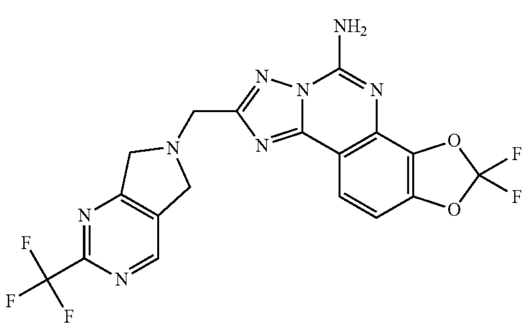 [SMILES: Nc1nc2c3c(ccc2c2nc(CN4Cc5cnc(C(F)(F)F)nc5C4)nn12)OC(F)(F)O3] | 2,2-difluoro-8-{[2-(trifluoromethyl)-5,7-dihydro-6H-pyrrolo[3,4-d]pyrimidin-6-yl]methyl}[1,3]dioxolo[4,5-h][1,2,4]triazolo[1,5-c]quinazolin-5-amine | 467 |

TABLE 8-continued

| Ex. No. | Structure | IUPAC Name | Exact Mass [M + H]+ |
|---|---|---|---|
| 122 | 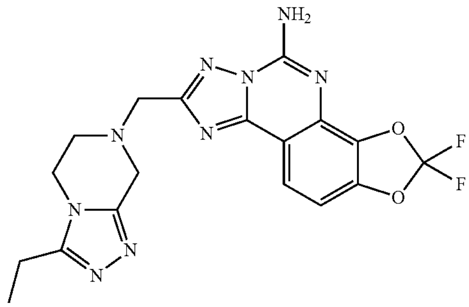 [SMILES: CCc1nnc2n1CCN(Cc1nc3c4ccc5c(c4nc(N)n3n1)OC(F)(F)O5)C2] | 8-[(3-ethyl-5,6-dihydro[1,2,4]triazolo[4,3-a]pyrazin-7(8H)-yl)methyl]-2,2-difluoro[1,3]dioxolo[4,5-h][1,2,4]triazolo[1,5-c]quinazolin-5-amine | 430 |
| 123 | 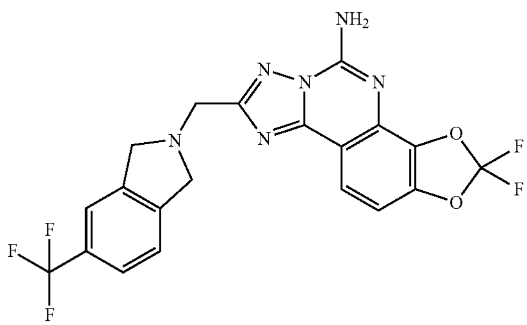 [SMILES: Nc1nc2c3c(ccc2c2nc(CN4Cc5ccc(C(F)(F)F)cc5C4)nn12)OC(F)(F)O3] | 2,2-difluoro-8-{[5-(trifluoromethyl)-1,3-dihydro-2H-isoindol-2-yl]methyl}[1,3]dioxolo[4,5-h][1,2,4]triazolo[1,5-c]quinazolin-5-amine | 465 |
| 124 | 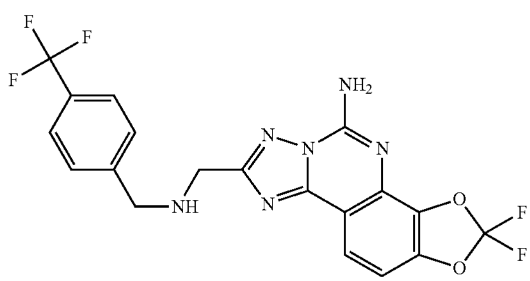 [SMILES: Nc1nc2c3c(ccc2c2nc(CNCc4ccc(C(F)(F)F)cc4)nn12)OC(F)(F)O3] | 2,2-difluoro-8-({[4-(trifluoromethyl)benzyl]amino}methyl)[1,3]dioxolo[4,5-h][1,2,4]triazolo[1,5-c]quinazolin-5-amine | 453 |
| 125 | 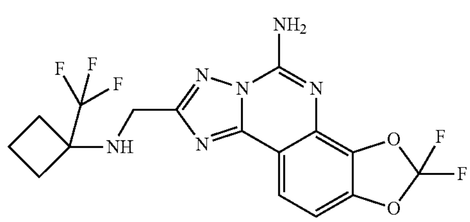 [SMILES: Nc1nc2c3c(ccc2c2nc(CNC4(C(F)(F)F)CCC4)nn12)OC(F)(F)O3] | 2,2-difluoro-8-({[1-(trifluoromethyl)cyclobutyl]amino}methyl)[1,3]dioxolo[4,5-h][1,2,4]triazolo[1,5-c]quinazolin-5-amine | 417 |
| 126 | 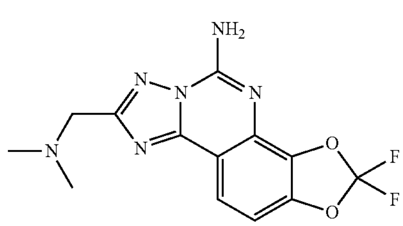 [SMILES: CN(C)Cc1nc2c3ccc4c(c3nc(N)n2n1)OC(F)(F)O4] | 8-[(dimethylamino)methyl]-2,2-difluoro[1,3]dioxolo[4,5-h][1,2,4]triazolo[1,5-c]quinazolin-5-amine | 323 |

TABLE 8-continued

| Ex. No. | Structure | IUPAC Name | Exact Mass [M + H]+ |
|---|---|---|---|
| 127 | 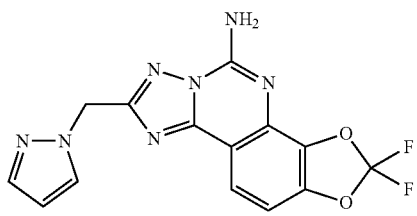 [SMILES: Nc1nc2c3c(ccc2c2nc(Cn4cccn4)nn12)OC(F)(F)O3] | 8-({(cyclopropylmethyl)[(4-methyl-1,3-thiazol-2-yl)methyl]amino}methyl)-2,2-difluoro[1,3]dioxolo[4,5-h][1,2,4]triazolo[1,5-c]quinazolin-5-amine | 460 |

Example 128

8-((1H-pyrazol-1-yl)methyl)-2,2-difluoro-[1,3]dioxolo[4,5-h][1,2,4]triazolo[1,5-c]quinazolin-5-amine Step A: 8-((1H-pyrazol-1-yl)methyl)-N-(2,4-dimethoxybenzyl)-2,2-difluoro-[1,3]dioxolo[4,5-h][1,2,4]triazolo[1,5-c]quinazolin-5-amine To a mixture of (5-((2,4-dimethoxybenzyl)amino)-2,2-difluoro-[1,3]dioxolo[4,5-h][1,2,4]triazolo[1,5-c]quinazolin-8-yl)methyl methanesulfonate (EXAMPLE 109 STEP A), pyrazole, potassium carbonate, and potassium iodide was charged acetonitrile. The reaction mixture was heated to 80° C. for 16 hours. It was cooled to room temperature, diluted with water, and extracted with ethyl acetate twice. The combined organic extracts were washed with brine, dried (potassium carbonate), and concentrated in vacuo to afford a crude product. Chromatography over silica gel, eluting with ethyl acetate/hexanes, afforded the title compound. LC/MS=496 [M+1].

Step B: 8-((1H-pyrazol-1-yl)methyl)-2,2-difluoro-[1,3]dioxolo[4,5-h][1,2,4]triazolo[1,5-c]quinazolin-5-amine The title compound was synthesized by following the procedures described in EXAMPLE 109, step D, substituting 8-((1H-pyrazol-1-yl)methyl)-N-(2,4-dimethoxybenzyl)-2,2-difluoro-[1,3]dioxolo[4,5-h][1,2,4]triazolo[1,5-c]quinazolin-5-amine for 8-((3,3-difluoroazetidin-1-yl)methyl)-N-(2,4-dimethoxybenzyl)-2,2-difluoro-[1,3]dioxolo[4,5-h][1,2,4]triazolo[1,5-c]quinazolin-5-amine. LC/MS=346 [M+1].

The compounds in Table 9 were prepared by using methods described in Example 128, substituting the appropriate pyrazole for pyrazole in step A

TABLE 9

| Ex. No. | Structure | IUPAC Name | Exact Mass [M + H]+ |
|---|---|---|---|
| 129 | 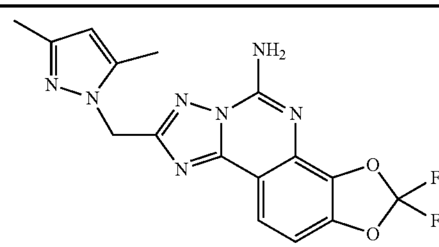 | 8-[(3,5-dimethyl-1H-pyrazol-1-yl)methyl]-2,2-difluoro[1,3]dioxolo[4,5-h][1,2,4]triazolo[1,5-c]quinazolin-5-amine | 374 |
| 130 | 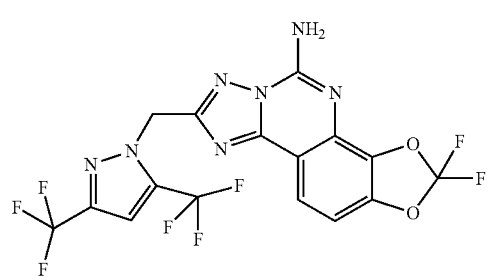 [SMILES: Nc1nc2c3c(ccc2c2nc(Cn4nc(C(F)(F)F)cc4C(F)(F)F)nn12)OC(F)(F)O3] | 8-{[3,5-bis(trifluoromethyl)-1H-pyrazol-1-yl]methyl}-2,2-difluoro[1,3]dioxolo[4,5-h][1,2,4]triazolo[1,5-c]quinazolin-5-amine | 482 |

The compounds in Table 10 were prepared by using methods described in Example 109, substituting (±)-1-(5-((2,4-dimethoxybenzyl)amino)-2,2-difluoro-[1,3]dioxolo[4,5-h][1,2,4]triazolo[1,5-c]quinazolin-8-yl)ethanol (INTERMEDIATE 6) for (5-((2,4-dimethoxybenzyl)amino)-2,2-difluoro-[1,3]dioxolo[4,5-h][1,2,4]triazolo[1,5-c]quinazolin-8-yl)methanol in step A, and the appropriate amine for 3,3-difluoroazetidine in step C. The racemic products were then separated into their enantiomers by chiral HPLC. Where the stereochemistry of a particular stereocenter in an isolated enantiomer is unknown, the stereocenter is designated by an "*".

TABLE 10

| Ex. No. | Structure | IUPAC Name | Exact Mass [M + H]+ |
|---|---|---|---|
| 131 | 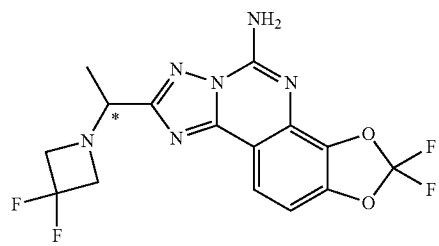 [SMILES: CC(c1nc2c3ccc4c(c3nc(N)n2n1)OC(F)(F)O4)N1CC(F)(F)C1] | (R or S)-8-[1-(3,3-difluoroazetidin-1-yl)ethyl]-2,2-difluoro[1,3]dioxolo[4,5-h][1,2,4]triazolo[1,5-c]quinazolin-5-amine (faster eluting [a]) | 385 |
| 132 | 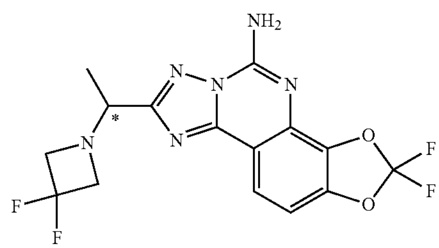 [SMILES: CC(c1nc2c3ccc4c(c3nc(N)n2n1)OC(F)(F)O4)N1CC(F)(F)C1] | (R or S)-8-[1-(3,3-difluoroazetidin-1-yl)ethyl]-2,2-difluoro[1,3]dioxolo[4,5-h][1,2,4]triazolo[1,5-c]quinazolin-5-amine (slower eluting [a]) | 385 |
| 133 | 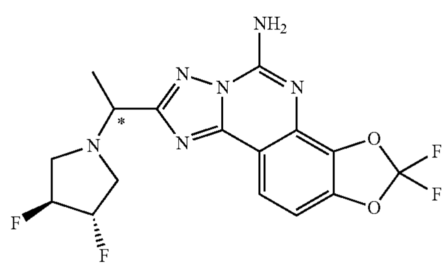 [SMILES: CC(c1nc2c3ccc4c(c3nc(N)n2n1)OC(F)(F)O4)N1C[C@H](F)[C@@H](F)C1] | (R or S)-8-{1-[(3S,4S)-3,4-difluoropyrrolidin-1-yl]ethyl}-2,2-difluoro[1,3]dioxolo[4,5-h][1,2,4]triazolo[1,5-c]quinazolin-5-amine (faster eluting [a]) | 399 |
| 134 | 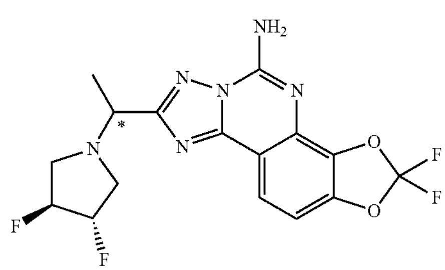 [SMILES: CC(c1nc2c3ccc4c(c3nc(N)n2n1)OC(F)(F)O4)N1C[C@H](F)[C@@H](F)C1] | (R or S)-8-{1-[(3S,4S)-3,4-difluoropyrrolidin-1-yl]ethyl}-2,2-difluoro[1,3]dioxolo[4,5-h][1,2,4]triazolo[1,5-c]quinazolin-5-amine (slower eluting [a]) | 399 |
| 135 | 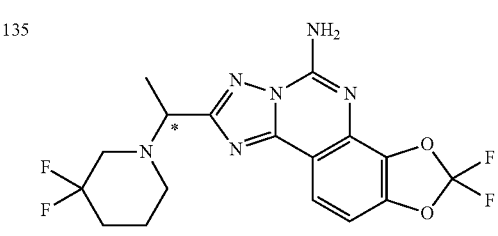 | 8-[(1S or 1R)-1-(3,3-difluoropiperidin-1-yl)ethyl]-2,2-difluoro[1,3]dioxolo[4,5-h][1,2,4]triazolo[1,5-c]quinazolin-5-amine (faster eluting [b]) | 413 |

TABLE 10-continued

| Ex. No. | Structure | IUPAC Name | Exact Mass [M + H]+ |
|---|---|---|---|
| 136 | 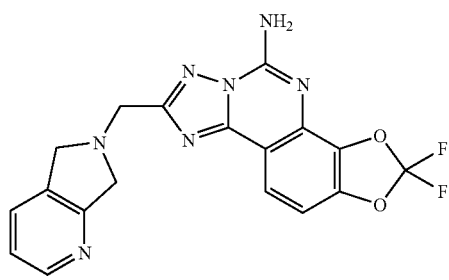 [SMILES: Nc1nc2c3c(ccc2c2nc(CN4Cc5cccnc5C4)nn12)OC(F)(F)O3] | 8-[(1S or 1R)-1-(3,3-difluoropiperidin-1-yl)ethyl]-2,2-difluoro[1,3]dioxolo[4,5-h][1,2,4]triazolo[1,5-c]quinazolin-5-amine (slower eluting [b]) | 413 |

[a] HPLC: Chiralcel OJ-H (methanol/supercritical carbon dioxide)
[b] HPLC: Chiralpak AD-H (isopropanol/supercritical carbon dioxide)

Example 137

8-(3-(5H-pyrrolo[3,4-b]pyridin-6(7H)-yl)propyl)-2,2-difluoro-[1,3]dioxolo[4,5-h][1,2,4]triazolo[1,5-c]quinazolin-5-amine The title compound was prepared by using methods described in Example 6, substituting 3-(5-((2,4-dimethoxybenzyl)amino)-2,2-difluoro-[1,3]dioxolo[4,5-h][1,2,4]triazolo[1,5-c]quinazolin-8-yl)propan-1-ol for 2-(5-((2,4-dimethoxybenzyl)amino)-2,2-difluoro-[1,3]dioxolo[4,5-h][1,2,4]triazolo[1,5-c]quinazolin-8-yl)ethanol in step A. LC/MS=426 [M+1].

Example 138

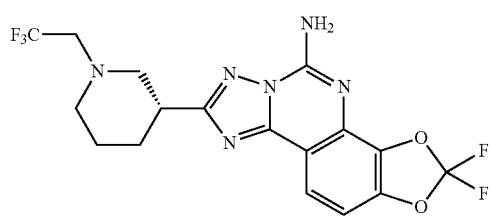 [SMILES: Nc1nc2c3c(ccc2c2nc([C@@H]4CCCN(CC(F)(F)F)C4)nn12)OC(F)(F)O3]

(R)-2,2-difluoro-8-(1-(2,2,2-trifluoroethyl)piperidin-3-yl)-[1,3]dioxolo[4,5-h][1,2,4]triazolo[1,5-c]quinazolin-5-amine Step A: (R)-tert-butyl 3-(5-amino-2,2-difluoro-[1,3]dioxolo[4,5-h][1,2,4]triazolo[1,5-c]quinazolin-8-yl)piperidine-1-carboxylate To an acetonitrile (5 mL)/water (1 mL) solution of (R)-tert-butyl 3-(5-((2,4-dimethoxybenzyl)amino)-2,2-difluoro-[1,3]dioxolo[4,5-h][1,2,4]triazolo[1,5-c]quinazolin-8-yl)piperidine-1-carboxylate (525 mg, 0.876 mmol, INTERMEDIATE 8) was added ammonium cerium(IV) nitrate (1200 mg, 2.19 mmol, 2.5 equiv.). The reaction mixture was stirred at room temperature for 10 minutes. It was diluted with water and extracted with ethyl acetate (2×). The combined organic extracts were washed with brine, dried (magnesium sulfate), filtered and concentrated in vacuo to afford a crude solid. Chromatography over silica gel, eluting with ethyl acetate/hexanes, afforded the title compound. LC/MS=449 [M+1].

Step B: (R)-2,2-difluoro-8-(piperidin-3-yl)-[1,3]dioxolo[4,5-h][1,2,4]triazolo[1,5-c]quinazolin-5-amine To a methanolic (5 mL) solution of (R)-tert-butyl 3-(5-amino-2,2-difluoro-[1,3]dioxolo[4,5-h][1,2,4]triazolo[1,5-c]quinazolin-8-yl)piperidine-1-carboxylate (248 mg, 0.553 mmol, STEP A) was added a 4.0 M dioxane solution of hydrogen chloride (2.0 mL, 8.0 mmol, 14 equiv.). The reaction mixture was stirred at room temperature for 5 hours. It was concentrated in vacuo to afford the title compound, which was used in the subsequent step without further purification. LC/MS=349 [M+1].

Step C: (R)-2,2-difluoro-8-(1-(2,2,2-trifluoroethyl)piperidin-3-yl)-[1,3]dioxolo[4,5-h][1,2,4]triazolo[1,5-c]quinazolin-5-amine To a N,N-dimethylformamide (1 mL) suspension of (R)-2,2-difluoro-8-(piperidin-3-yl)-[1,3]dioxolo[4,5-h][1,2,4]triazolo[1,5-c]quinazolin-5-amine (59.9 mg, 0.156 mmol, STEP B) and potassium carbonate (64.5 mg, 0.467 mmol, 3.0 equiv.) was added 2,2,2-trifluoroethyl trifluoromethanesulfonate (60 μL, 0.416 mmol, 2.7 equiv.). The reaction mixture was stirred at room temperature for 18 hours. It was diluted with ethyl acetate and washed with water. The aqueous layer was extracted once more with ethyl acetate. The combined organic extracts were washed with brine and concentrated in vacuo to a crude product. Chromatography over silica gel, eluting with ethyl acetate/hexanes, afforded the purified compound. It was further purified by supercritical fluid chromatography (Chiralcel OJ, methanol/supercritical carbon dioxide) to afford the title compound in enantiopure form. LC/MS=431 [M+1].

Example 139

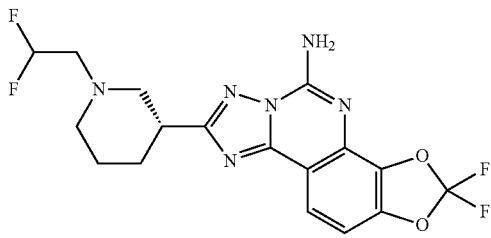 [SMILES: Nc1nc2c3c(ccc2c2nc([C@@H]4CCCN(CC(F)F)C4)nn12)OC(F)(F)O3]

(R)-8-(1-(2,2-difluoroethyl)piperidin-3-yl)-2,2-difluoro-[1,3]dioxolo[4,5-h][1,2,4]triazolo[1,5-c]quinazolin-5-amine The title compound was prepared by using methods described in Example 138, substituting 2,2-difluoroethyl trifluoromethanesulfonate for 2,2,2-trifluoroethyl trifluoromethanesulfonate in step C, and Chiralpak AD for Chiralcel OJ. LC/MS=413 [M+1].

Example 140

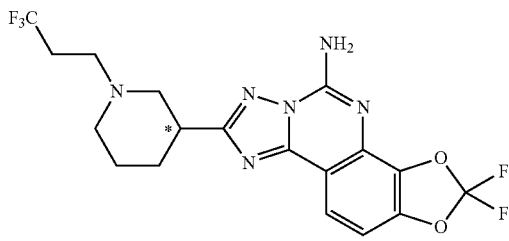 [SMILES: Nc1nc2c3c(ccc2c2nc(C4CCCN(CCC(F)(F)F)C4)nn12)OC(F)(F)O3]

(R or S)-2,2-difluoro-8-(1-(3,3,3-trifluoropropyl) piperidin-3-yl)-[1,3]dioxolo[4,5-h][1,2,4]triazolo[1, 5-c]quinazolin-5-amine (faster eluting)

The stereochemistry of the stereocenter designated by an "*" in this isolated enantiomer is unknown.

Step A: (±)-N-(2,4-dimethoxybenzyl)-2,2-difluoro-8-(piperidin-3-yl)-[1,3]dioxolo[4,5-h][1,2,4]triazolo[1,5-c]quinazolin-5-amine To a dichloromethane (30 mL) solution of (±)-tert-butyl 3-(5-(2,4-dimethoxybenzylamino)-2,2-difluoro-[1,3]dioxolo[4,5-h][1,2,4]triazolo[1,5-c]quinazolin-8-yl)piperidine-1-carboxylate (2.3 g, 3.9 mmol, INTERMEDIATE 9) at 0° C. was added trifluoroacetic acid (3 mL) dropwise. After the addition was completed, the reaction mixture was stirred at room temperature for 4 hours. The solution was washed with saturated aqueous sodium hydrogencarbonate (20 mL×3) and brine (20 mL). It was then concentrated in vacuo to afford the title compound as a yellow solid, which was used in the subsequent step without further purification. LC/MS=499 [M+1].

Step B: (±)-N-(2,4-dimethoxybenzyl)-2,2-difluoro-8-(1-(3,3,3-trifluoropropyl)piperidin-3-yl)-[1,3]dioxolo[4,5-h][1,2,4]triazolo[1,5-c]quinazolin-5-amine To a N,N-dimethylformamide (2.0 mL) solution of (±)-N-(2,4-dimethoxybenzyl)-2,2-difluoro-8-(piperidin-3-yl)-[1,3]dioxolo[4,5-h][1,2,4]triazolo[1,5-c]quinazolin-5-amine (400 mg, 0.8 mmol, STEP A) were added 1,1,1-trifluoro-3-iodopropane (540 mg, 2.4 mmol, 3.0 equiv.) and potassium carbonate (220 mg, 1.6 mmol, 2.0 equiv.). The reaction mixture was stirred at room temperature for 16 hours. Water (10 mL) was then added, and the mixture was extracted with ethyl acetate (3×20 mL). The combined organic layers were washed with brine (30 mL), dried (sodium sulfate), filtered and concentrated to afford the title compound as a yellow solid, which was used in the subsequent step without further purification. LC/MS=595 [M+1].

Step C: (±)-2,2-difluoro-8-(1-(3,3,3-trifluoropropyl) piperidin-3-yl)-[1,3]dioxolo[4,5-h][1,2,4]triazolo[1, 5-c]quinazolin-5-amine The title compound was synthesized by following the procedures described in EXAMPLE 109, step D, substituting (±)-N-(2,4-dimethoxybenzyl)-2,2-difluoro-8-(1-(3,3,3-trifluoropropyl)piperidin-3-yl)-[1,3]dioxolo[4,5-h][1,2,4]triazolo[1,5-c]quinazolin-5-amine (STEP B) for 8-((3,3-difluoroazetidin-1-yl)methyl)-N-(2,4-dimethoxybenzyl)-2,2-difluoro-[1,3]dioxolo[4,5-h][1,2,4]triazolo[1,5-c]quinazolin-5-amine. LC/MS=445 [M+1].

Step D: 2,2-difluoro-8-(1-(3,3,3-trifluoropropyl) piperidin-3-yl)-[1,3]dioxolo[4,5-h][1,2,4]triazolo[1, 5-c]quinazolin-5-amine Chromatography of the racemic mixture (STEP C) over Chiralcel OJ-H column, eluting with methanol/supercritical carbon dioxide, afforded the title compound as the fast-eluting enantiomer.

Example 141

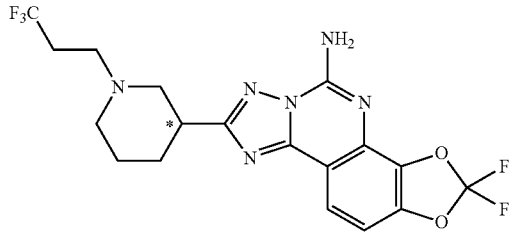 [SMILES: Nc1nc2c3c(ccc2c2nc(C4CCCN(CCC(F)(F)F)C4)nn12)OC(F)(F)O3]

(R or S)-2,2-difluoro-8-(1-(3,3,3-trifluoropropyl) piperidin-3-yl)-[1,3]dioxolo[4,5-h][1,2,4]triazolo[1, 5-c]quinazolin-5-amine (slower eluting)

The stereochemistry of the stereocenter designated by an "*" in this isolated enantiomer is unknown.

Chromatography of the racemic mixture (EXAMPLE 140, STEP C) over Chiralcel OJ-H column, eluting with methanol/supercritical carbon dioxide, afforded the title compound as the slow-eluting enantiomer.

Example 142

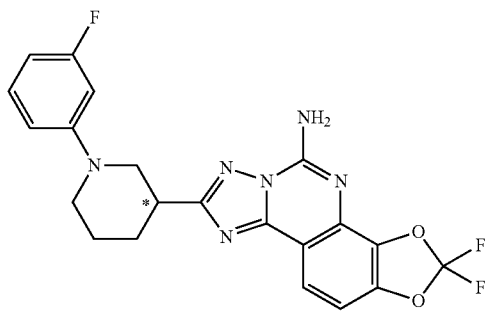 [SMILES: Nc1nc2c3c(ccc2c2nc(C4CCCN(c5cccc(F)c5)C4)nn12)OC(F)(F)O3]

(R or S)-2,2-difluoro-8-[1-(3-fluorophenyl)piperidin-3-yl][1,3]dioxolo[4,5-h][1,2,4]triazolo[1,5-c]quinazolin-5-amine (faster eluting)

The stereochemistry of the stereocenter designated by an "*" in this isolated enantiomer is unknown.

Step A: (±)-N-(2,4-dimethoxybenzyl)-2,2-difluoro-8-[1-(3-fluorophenyl)piperidin-3-yl][1,3]dioxolo[4,5-h][1,2,4]triazolo[1,5-c]quinazolin-5-amine A tetrahydrofuran (2 mL) mixture of (±)-N-(2,4-dimethoxybenzyl)-2,2-difluoro-8-(piperidin-3-yl)-[1,3]dioxolo[4,5-h][1,2,4]triazolo[1,5-c]quinazolin-5-amine (50 mg, 0.10 mmol, EXAMPLE 140, STEP A), 1-bromo-3-fluorobenzene (88 mg, 0.50 mmol, 5.0 equiv.), 2-dicyclohexylphosphino-2',6'-diisopropoxybiphenyl (19 mg, 0.04 mmol, 0.4 equiv.), tris(dibenzylideneacetone)dipalladium(0) (21 mg, 0.03 mmol, 0.3 equiv.), and potassium tert-butoxide (13 mg, 0.12 mmol, 1.2 equiv.) was heated by microwaves in a sealed tube at 115° C. for 3 hours. The reaction mixture was poured into water (20 mL) and extracted with dichloromethane (25 mL×3). The combined organic extracts were dried (magnesium sulfate) and concentrated in vacuo to afford the crude product. Purification by preparative thin-layer chromatography, eluting with ethyl acetate, afforded the title compound. LC/MS=593 [M+1].

Step B: (±)-2,2-difluoro-8-[1-(3-fluorophenyl)piperidin-3-yl][1,3]dioxolo[4,5-h][1,2,4]triazolo[1,5-c]quinazolin-5-amine The title compound was synthesized by following the procedures described in EXAMPLE 109, step D, substituting (±)-N-(2,4-dimethoxybenzyl)-2,2-difluoro-8-[1-(3-fluorophenyl)piperidin-3-yl][1,3]dioxolo[4,5-h][1,2,4]triazolo[1,5-c]quinazolin-5-amine (STEP A) for 8-((3,3-difluoroazetidin-1-yl)methyl)-N-(2,4-dimethoxybenzyl)-2,2-difluoro-[1,3]dioxolo[4,5-h][1,2,4]triazolo[1,5-c]quinazolin-5-amine. LC/MS=443 [M+1].

Step C: 2,2-difluoro-8-[1-(3-fluorophenyl)piperidin-3-yl][1,3]dioxolo[4,5-h][1,2,4]triazolo[1,5-c]quinazolin-5-amine Chromatography of the racemic mixture (EXAMPLE 142, STEP B) over Chiralcel OJ-H column, eluting with methanol/supercritical carbon dioxide, afforded the title compound as the fast-eluting enantiomer.

Example 143

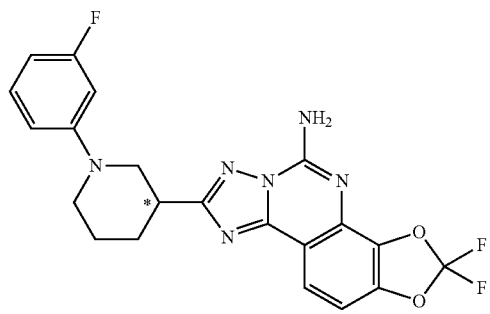 [SMILES: Nc1nc2c3c(ccc2c2nc(C4CCCN(c5cccc(F)c5)C4)nn12)OC(F)(F)O3]

(R or S)-2,2-difluoro-8-[1-(3-fluorophenyl)piperidin-3-yl][1,3]dioxolo[4,5-h][1,2,4]triazolo[1,5-c]quinazolin-5-amine (slower eluting)

The stereochemistry of the stereocenter designated by an "*" in this isolated enantiomer is unknown.

Chromatography of the racemic mixture (EXAMPLE 142, STEP B) over Chiralcel OJ-H column, eluting with methanol/supercritical carbon dioxide, afforded the title compound as the slow-eluting enantiomer.

The compounds in Table 11 were prepared by using methods described in Example 142, substituting the appropriate aryl or heteroaryl bromide for 1-bromo-3-fluorobenzene in step A. The racemic products were then separated into their enantiomers by chiral HPLC. Where the stereochemistry of a particular stereocenter in an isolated enantiomer is unknown, the stereocenter is designated by an "*".

TABLE 11

| Ex. No. | Structure | IUPAC Name | Exact Mass [M + H]+ |
|---|---|---|---|
| 144 | ![structure] | (R or S)-8-[1-(3,5-difluorophenyl)piperidin-3-yl]-2,2-difluoro[1,3]dioxolo[4,5-h][1,2,4]triazolo[1,5-c]quinazolin-5-amine (faster eluting *a*) | 461 |

TABLE 11-continued

| Ex. No. | Structure | IUPAC Name | Exact Mass [M + H]+ |
|---|---|---|---|
| 145 | 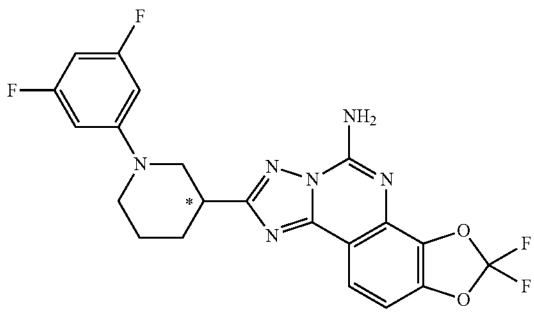 [SMILES: Nc1nc2c3c(ccc2c2nc(C4CCCN(c5cc(F)cc(F)c5)C4)nn12)OC(F)(F)O3] | (R or S)-8-[1-(3,5-difluorophenyl)piperidin-3-yl]-2,2-difluoro[1,3]dioxolo[4,5-h][1,2,4]triazolo[1,5-c]quinazolin-5-amine (slower eluting $^a$) | 461 |
| 146 | 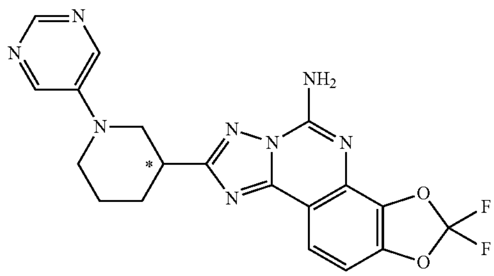 [SMILES: Nc1nc2c3c(ccc2c2nc(C4CCCN(c5cncnc5)C4)nn12)OC(F)(F)O3] | (R or S)-2,2-difluoro-8-(1-pyrimidin-5-ylpiperidin-3-yl)[1,3]dioxolo[4,5-h][1,2,4]triazolo[1,5-c]quinazolin-5-amine (faster eluting $^b$) | 427 |
| 147 | 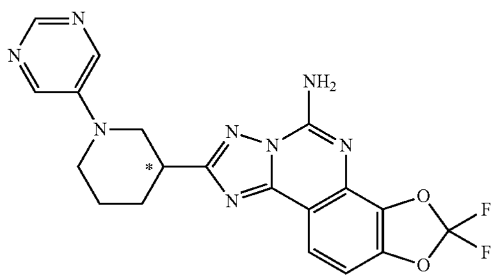 [SMILES: Nc1nc2c3c(ccc2c2nc(C4CCCN(c5cncnc5)C4)nn12)OC(F)(F)O3] | (R or S)-2,2-difluoro-8-(1-pyrimidin-5-ylpiperidin-3-yl)[1,3]dioxolo[4,5-h][1,2,4]triazolo[1,5-c]quinazolin-5-amine (slower eluting $^b$) | 427 |

$^a$ HPLC condition: Chiralcel OJ-H (methanol/supercritical carbon dioxide)
$^b$ HPLC condition: Chiralpak AS-H (methanol/supercritical carbon dioxide)

Example 148

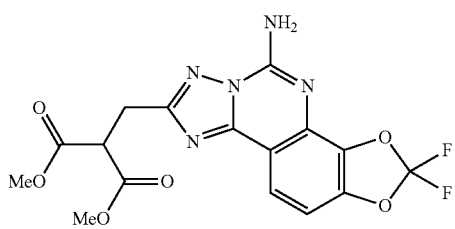 [SMILES: COC(=O)C(Cc1nc2c3ccc4c(c3nc(N)n2n1)OC(F)(F)O4)C(=O)OC]

dimethyl [(5-amino-2,2-difluoro[1,3]dioxolo[4,5-h][1,2,4]triazolo[1,5-c]quinazolin-8-yl)methyl]propanedioate To an acetonitrile (5 mL) solution of dimethyl malonate (505 mg, 3.83 mmol, 3.0 equiv.) and potassium iodide (635 mg, 3.83 mmol, 3.0 equiv.) was added 8-(chloromethyl)-2,2-difluoro-[1,3]dioxolo[4,5-h][1,2,4]triazolo[1,5-c]quinazolin-5-amine (400 mg, 1.28 mmol, EXAMPLE 102, STEP B), followed by sodium hydride (66.3 mg, 1.66 mmol, 1.3 equiv.). The reaction mixture was stirred at 70° C. for 12 hours. It was then poured into water, and the precipitate was collected by filtration, washed with water, and dried in vacuo to afford the crude product. Purification by reversed-phase HPLC, eluting with acetonitrile/water, afforded the title compound as a white solid. LC/MS=410 [M+1].

Example 149

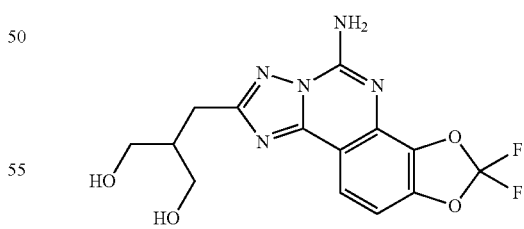

2-[(5-amino-2,2-difluoro[1,3]dioxolo[4,5-h][1,2,4]triazolo[1,5-c]quinazolin-8-yl)methyl]propane-1,3-diol To a tetrahydrofuran (2 mL)/ethanol (2 mL) suspension of lithium chloride (9.5 mg, 0.23 mmol, 0.21 equiv.) and sodium borohydride (170 mg, 4.5 mmol, 4.0 equiv.) at room temperature was added dimethyl [(5-amino-2,2-difluoro[1,3]dioxolo[4,5-h][1,2,4]triazolo[1,5-c]quinazolin-8-yl)

methyl]propanedioate (460 mg, 1.12 mmol, EXAMPLE 148). The reaction mixture was stirred at room temperature for 12 hours. It was cooled in a ice-water bath, and 1.0N hydrochloric acid was added dropwise until the pH was adjusted to about 4-5. The white precipitate was collected by filtration, washed with water, and dried in vacuo to afford the crude product. Purification by reversed-phase HPLC, eluting with acetonitrile/water, afforded the title compound as a white solid. LC/MS=354 [M+1].

Example 150

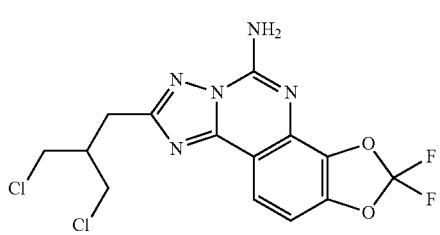 [SMILES: Nc1nc2c3c(ccc2c2nc(CC(CCl)CCl)nn12)OC(F)(F)O3]

8-[3-chloro-2-(chloromethyl)propyl]-2,2-difluoro[1,3]dioxolo[4,5-h][1,2,4]triiazolo[1,5-c]quinazolin-5-amine 2-[(5-Amino-2,2-difluoro[1,3]dioxolo[4,5-h][1,2,4]triazolo[1,5-c]quinazolin-8-yl)methyl]propane-1,3-diol (340 mg, 0.96 mmol, EXAMPLE 149) was mixed with thionyl chloride (3.5 mL, 48 mmol), and the reaction mixture was heated to 65° C. for 2 hours. The solvent was removed in vacuo, and saturated aqueous sodium hydrogencarbonate solution (5 mL) was added. The mixture was extracted with ethyl acetate, and the organic layer was washed with brine, dried (sodium sulfate), and concentrated in vacuo to afford the crude product. Purification by reversed-phase HPLC, eluting with acetonitrile/water, afforded the title compound. LC/MS=390 [M+1].

Example 151

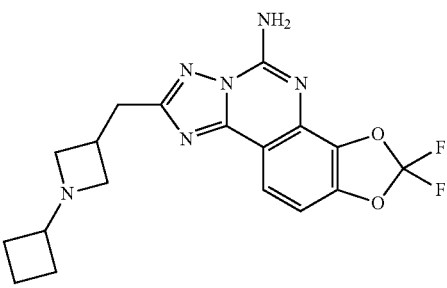 [SMILES: Nc1nc2c3c(ccc2c2nc(CC4CN(C5CCC5)C4)nn12)OC(F)(F)O3]

8-[(1-cyclobutylazetidin-3-yl)methyl]-2,2-difluoro[1,3]dioxolo[4,5-h][1,2,4]triazolo[1,5-c]quinazolin-5-amine In a microwave reaction vial, 8-(3-chloro-2-(chloromethyl)propyl)-2,2-difluoro-[1,3]dioxolo[4,5-h][1,2,4]triazolo[1,5-c]quinazolin-5-amine (20 mg, 0.051 mmol, EXAMPLE 150) was mixed with cyclobutylamine (8.8 μL, 0.10 mmol, 2.0 equiv.), and N,N-diisopropylethylamine (0.027 mL, 0.15 mmol, 3.0 equiv.) in N,N-dimethylformamide (0.3 mL). The vial was capped, and heated to 100° C. for 20 hours. The reaction mixture was diluted with N,N-dimethylformamide, and purification by reversed-phase HPLC, eluting with acetonitrile/water, afforded the title compound as a white yellow solid. LC/MS=389 [M+1].

The compounds in Table 12 were prepared by using methods described in Example 151, substituting the appropriate amine for cyclobutylamine.

TABLE 12

| Ex. No. | Structure | IUPAC Name | Exact Mass [M + H]+ |
|---|---|---|---|
| 152 | 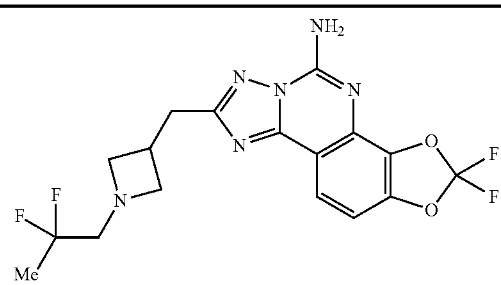 | 8-{[1-(2,2-difluoropropyl)azetidin-3-yl]methyl}-2,2-difluoro[1,3]dioxolo[4,5-h][1,2,4]triazolo[1,5-c]quinazolin-5-amine | 413 |
| 153 | 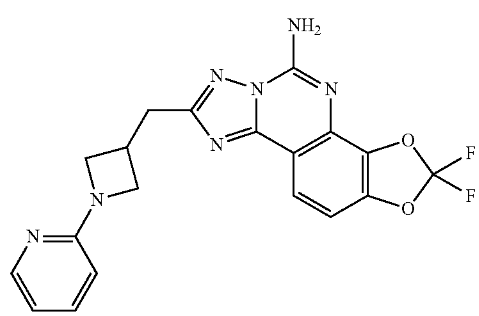 [SMILES: Nc1nc2c3c(ccc2c2nc(CC4CN(c5ccccn5)C4)nn12)OC(F)(F)O3] | 2,2-difluoro-8-[(1-pyridin-2-ylazetidin-3-yl)methyl][1,3]dioxolo[4,5-h][1,2,4]triazolo[1,5-c]quinazolin-5-amine | 412 |

Example 154

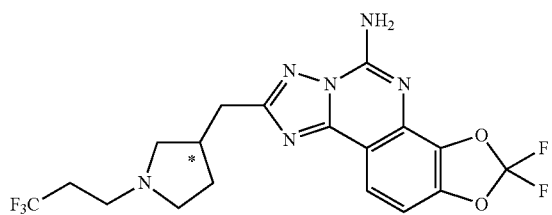

(R or S)-2,2-difluoro-8-{[1-(3,3,3-trifluoropropyl)
pyrrolidin-3-yl]methyl}[1,3]dioxolo[4,5-h][1,2,4]
triazolo[1,5-c]quinazolin-5-amine (faster eluting)

The stereochemistry of the stereocenter designated by an "*" in this isolated enantiomer is unknown.

Step A: tert-butyl 3-[(5-amino-2,2-difluoro[1,3]di-oxolo[4,5-h][1,2,4]triazolo[1,5-c]quinazolin-8-yl) methyl]-2,5-dihydro-1H-pyrrole-1-carboxylate To a microwave vial were added 8-(chloromethyl)-2,2-difluoro-[1,3]dioxolo[4,5-h][1,2,4]triazolo[1,5-c]quinazolin-5-amine (0.67 g, 2.1 mmol, EXAMPLE 102, STEP B), tert-butyl 3-(4,4,5,5-tetramethyl-1,3,2-dioxaborolan-2-yl)-2,5-dihydro-1H-pyrrole-1-carboxylate (1.0 g, 3.4 mmol, 1.6 equiv.), [1,1'-bis(diphenylphosphino)ferrocene]dichloropalladium(II) (0.31 g, 0.43 mmol, 0.2 equiv.) and potassium carbonate (0.59 g, 4.3 mmol, 2.0 equiv.). The vial was capped, evacuated and refilled with nitrogen. Dioxane (20 mL) and water (4 mL) were added, and the mixture was stirred at 110° C. for 90 minutes. The reaction mixture was filtered, and purification by reversed-phase HPLC, eluting with acetonitrile/water, afforded the title compound as a yellow solid. LC/MS=447 [M+1].

Step B: tert-butyl 3-[(5-amino-2,2-difluoro[1,3]di-oxolo[4,5-h][1,2,4]triazolo[1,5-c]quinazolin-8-yl) methyl]pyrrolidine-1-carboxylate To a methanol (10 mL) solution of tert-butyl 3-[(5-amino-2,2-difluoro[1,3]dioxolo[4,5-h][1,2,4]triazolo[1,5-c]quinazolin-8-yl)methyl]-2,5-dihydro-1H-pyrrole-1-carboxylate (0.45 g, 1.0 mmol, STEP A) was added 10 wt % palladium on carbon (0.16 g, 1.5 mmol). The reaction mixture was stirred under hydrogen (45 psi) for 2 hours. It was filtered and concentrated in vacuo to afford the title compound as white solid. LC/MS=449 [M+1]. Chromatography of the racemic mixture over Chiralpak AD column, eluting with methanol/acetonitrile/supercritical carbon dioxide, afforded the separate enantiomers.

Step C: 2,2-difluoro-8-(pyrrolidin-3-ylmethyl)[1,3] dioxolo[4,5-h][1,2,4]triazolo[1,5-c]quinazolin-5-amine To a dichloromethane (1.0 mL) solution of the fast enantiomer of tert-butyl 3-[(5-amino-2,2-difluoro[1,3]dioxolo[4,5-h][1,2,4]triazolo[1,5-c]quinazolin-8-yl)methyl] pyrrolidine-1-carboxylate (0.16 g, 0.36 mmol, STEP B) was added a 4.0 M dioxane solution of hydrogen chloride (0.5 mL, 6.0 mmol). It was stirred at room temperature for 4 hours and concentrated in vacuo to afford the hydrochloride salt of the title compound, which was used in the subsequent step without further purification. LC/MS=349 [M+1].

Step D: 2,2-difluoro-8-{[1-(3,3,3-trifluoropropyl) pyrrolidin-3-yl]methyl}[1,3]dioxolo[4,5-h][1,2,4] triazolo[1,5-c]quinazolin-5-amine To a N,N-dimethylformamide (2.0 mL) solution of the hydrochloride salt of the fast enantiomer of 2,2-difluoro-8-(pyrrolidin-3-ylmethyl)[1,3]dioxolo[4,5-h][1,2,4]triazolo[1,5-c]quinazolin-5-amine (38 mg, 0.10 mmol, STEP C) were added 1,1,1-trifluoro-3-iodopropane (34 mg, 0.15 mmol, 1.5 equiv.), potassium carbonate (28 mg, 0.20 mmol, 2.0 equiv.) and N,N-diisopropylethylamine (0.035 mL, 0.20 mmol, 2.0 equiv.). The reaction mixture was stirred at 60° C. for 6 hours. It was filtered, and purification by reversed-phase HPLC, eluting with acetonitrile/water, afforded the title compound as a yellow solid. LC/MS=445 [M+1].

Example 155

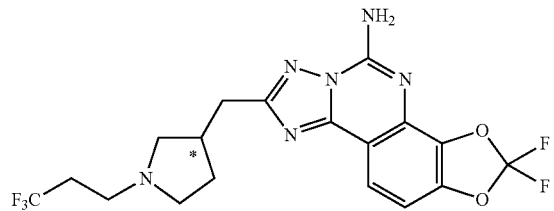 [SMILES: Nc1nc2c3c(ccc2c2nc(CC4CCN(CCC(F)(F)F)C4)nn12)OC(F)(F)O3]

(R or S)-2,2-difluoro-8-{[1-(3,3,3-trifluoropropyl)
pyrrolidin-3-yl]methyl}[1,3]dioxolo[4,5-h][1,2,4]
triazolo[1,5-c]quinazolin-5-amine (slower eluting)

The stereochemistry of the stereocenter designated by an "*" in this isolated enantiomer is unknown.

EXAMPLE 155, the opposite enantiomer of EXAMPLE 154, was synthesized by following the procedures described in example 154, substituting the slow enantiomer of tert-butyl 3-[(5-amino-2,2-difluoro[1,3]dioxolo[4,5-h][1,2,4]triazolo[1,5-c]quinazolin-8-yl)methyl]pyrrolidine-1-carboxylate for the fast enantiomer of tert-butyl 3-[(5-amino-2,2-difluoro[1,3]dioxolo[4,5-h][1,2,4]triazolo[1,5-c]quinazolin-8-yl)methyl]pyrrolidine-1-carboxylate in step C. LC/MS=445 [M+1].

The compounds in Table 13 were prepared by using methods described in Example 154, substituting the appropriate iodide for 1,1,1-trifluoro-3-iodopropane in step D. The stereochemistry of the stereocenter designated by an "*" in this isolated enantiomer is unknown.

TABLE 13

| Ex. No. | Structure | IUPAC Name | Exact Mass [M + H]+ |
|---|---|---|---|
| 156 | 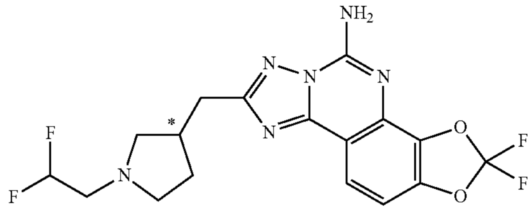 [SMILES: Nc1nc2c3c(ccc2c2nc(CC4CCN(CC(F)F)C4)nn12)OC(F)(F)O3] | (R or S)-8-{[1-(2,2-difluoroethyl)pyrrolidin-3-yl]methyl}-2,2-difluoro[1,3]dioxolo[4,5-h][1,2,4]triazolo[1,5-c]quinazolin-5-amine | 413 |
| 157 | 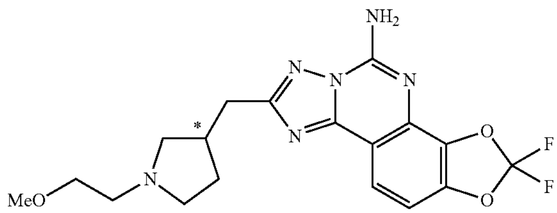 [SMILES: COCCN1CCC(Cc2nc3c4ccc5c(c4nc(N)n3n2)OC(F)(F)O5)C1] | (R or S)-2,2-difluoro-8-{[1-(2-methoxyethyl)pyrrolidin-3-yl]methyl}[1,3]dioxolo[4,5-h][1,2,4]triazolo[1,5-c]quinazolin-5-amine | 407 |

Example 158

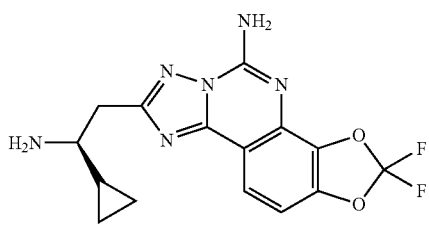 [SMILES: Nc1nc2c3c(ccc2c2nc(C[C@H](N)C4CC4)nn12)OC(F)(F)O3]

8-[(2S)-2-amino-2-cyproplethyl]-2,2-difluoro[1,3]dioxolo[4,5-h][1,2,4]triazolo[1,5-c]quinazolin-5-amine The title compound was prepared by using methods described in Example 3, substituting methyl (3S)-3-[(tert-butoxycarbonyl)amino]-3-cyclopropylpropanoate for ethyl 2-(2-chloropyridin-3-yl)acetate in step A. LC/MS=349 [M+1].

Example 159

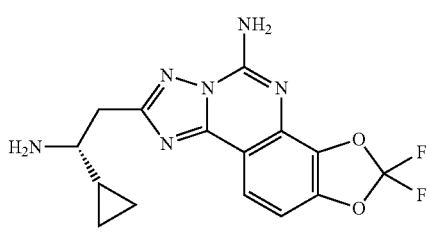 [SMILES: Nc1nc2c3c(ccc2c2nc(C[C@@H](N)C4CC4)nn12)OC(F)(F)O3]

8-[(2R)-2-amino-2-cyclopropylethyl]-2,2-difluoro[1,3]dioxolo[4,5-h][1,2,4]triazolo[1,5-c]quinazolin-5-amine The title compound was prepared by using methods described in Example 3, substituting methyl (3R)-3-[(tert-butoxycarbonyl)amino]-3-cyclopropylpropanoate for ethyl 2-(2-chloropyridin-3-yl)acetate in step A. LC/MS=349 [M+1].

Example 160

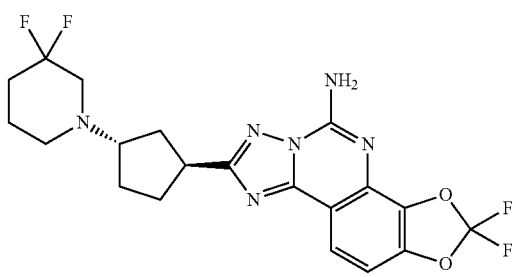 [SMILES: Nc1nc2c3c(ccc2c2nc([C@H]4CC[C@H](N5CCCC(F)(F)C5)C4)nn12)OC(F)(F)O3]

8-[(1S,3S)-3-(3,3-difluoropiperidin-1-yl)cyclopentyl]-2,2-difluoro[1,3]dioxolo[4,5-h][1,2,4]triazolo[1,5-c]quinazolin-5-amine Step A: methyl (1S)-3-oxocyclopentanecarboxylate To a dichloromethane (20 mL)/methanol (2 ml) solution of (1S)-3-oxocyclopentanecarboxylic acid (1.0 g, 7.8 mmol) at 0° C. was added dropwise a 2.0 M hexanes solution of (trimethylsilyl)diazomethane (5.1 mL, 10.2 mmol). Upon the completion of the addition, the reaction mixture was removed from the ice-bath to warm up to room temperature and stirred for 12 hours. It was concentrated in vacuo to afford the title compound, which was used in the subsequent step without further purification. $^1$H NMR (500 MHz, CDCl$_3$) δ 3.73 (s, 3H), 3.12-3.13 (m, 1H), 2.46-2.47 (m, 2H), 2.38-2.40 (m, 1H), 2.30-2.32 (m, 1H), 2.15-2.16 (m, 2H).

Step B: methyl (1S,3R)-3-(3,3-difluoropiperidin-1-yl)cyclopentanecarboxylate and methyl (1S,3S)-3-(3,3-difluoropiperidin-1-yl)cyclopentanecarboxylate To a dichloroethane (10 mL) solution of methyl (1S)-3-oxocyclopentanecarboxylate (0.28 mL, 2.2 mmol, step A), 3,3-difluoropiperidine hydrochloride (420 mg, 2.7 mmol, 1.2 equiv.), and triethylamine (0.43 mL, 3.1 mmol, 1.4 equiv.) were added sodium triacetoxyborohydride (940 mg, 4.4 mmol, 2.0 equiv.) and acetic acid (0.25 mL, 4.4 mmol, 2.0 equiv.). The reaction mixture was stirred at room temperature for 12 hours and quenched with 1N aqueous sodium hydroxide. It was extracted with dichloroethane, dried (sodium sulfate), and concentrated in vacuo to afford a crude product. Chromatography over silica gel, eluting with hexanes/ethyl acetate, afforded the title compound as a diastereomeric mixture. LC/MS=248 [M+1].

Step C: 8-[(1S,3S)-3-(3,3-difluoropiperidin-1-yl) cyclopentyl]-N-(2,4-dimethoxybenzyl)-2,2-difluoro [1,3]dioxolo[4,5-h][1,2,4]triazolo[1,5-c]quinazolin-5-amine The title compound was prepared by using methods described in Example 3, steps A through D, substituting methyl (1S,3R)-3-(3,3-difluoropiperidin-1-yl)cyclopentanecarboxylate and methyl (1S,3S)-3-(3,3-difluoropiperidin-1-yl)cyclopentanecarboxylate (STEP B) for ethyl 2-(2-chloropyridin-3-yl)acetate in step A. Chromatography over silica gel, eluting with hexanes/ethyl acetate, afforded the title compound as the less polar diastereomer. LC/MS=603 [M+1].

Step D: 8-[(1S,3S)-3-(3,3-difluoropiperidin-1-yl) cyclopentyl]-2,2-difluoro[1,3]dioxolo[4,5-h][1,2,4] triazolo[1,5-c]quinazolin-5-amine The title compound was prepared by using methods described in Example 3, step E, substituting 8-[(1S,3S)-3-(3,3-difluoropiperidin-1-yl)cyclopentyl]-N-(2,4-dimethoxybenzyl)-2,2-difluoro[1,3]dioxolo[4,5-h][1,2,4]triazolo[1,5-c]quinazolin-5-amine (STEP C) for 8-((2-chloropyridin-3-yl)methyl)-2,2-difluoro-[1,3]dioxolo[4,5-h][1,2,4]triazolo[1,5-c]quinazolin-5-amine. The stereochemical purity was improved by chromatography of the product over Chiralpak AD-H column, eluting with methanol/supercritical carbon dioxide. LC/MS=453 [M+1].

Example 161

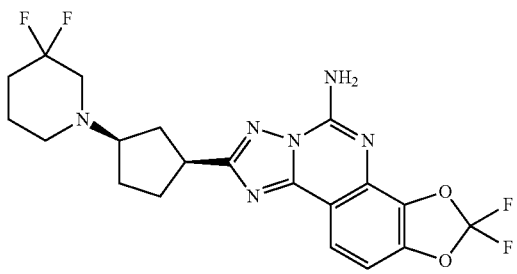 [SMILES: Nc1nc2c3c(ccc2c2nc([C@H]4CC[C@@H](N5CCCC(F)(F)C5)C4)nn12)OC(F)(F)O3]

8-[(1S,3R)-3-(3,3-difluoropiperidin-1-yl)cyclopentyl]-2,2-difluoro[1,3]dioxolo[4,5-h][1,2,4]triazolo[1,5-c]quinazolin-5-amine The title compound was prepared by using methods described in Example 160, substituting 8-[(1S,3R)-3-(3,3-difluoropiperidin-1-yl)cyclopentyl]-N-(2,4-dimethoxybenzyl)-2,2-difluoro[1,3]dioxolo[4,5-h][1,2,4]triazolo[1,5-c] quinazolin-5-amine (more polar diastereomer, EXAMPLE 160, STEP C) for 8-[(1S,3S)-3-(3,3-difluoropiperidin-1-yl) cyclopentyl]-N-(2,4-dimethoxybenzyl)-2,2-difluoro[1,3]dioxolo[4,5-h][1,2,4]triazolo[1,5-c]quinazolin-5-amine in step D. LC/MS=453 [M+1].

Table 14

The following table shows representative data for the compounds of the Examples as A2a receptor antagonists as determined by a competition binding assay using Scintillation Proximity technology. Thus, 1.0 µg of membranes from CHO-K1 cells expressing the human A2a receptor were incubated with a compound of the invention at concentrations ranging from 3000 nM to 0.15 nM in a reaction mixture also containing 2.0 nM of a tritiated form of 5-amino-7-[2-phenethyl]-2-(furan-2-yl)-7H-pyrazolo[4,3-e][1,2,4]triazolo[1,5-c]pyrimidine (the tritiated compound) and 100 µg of wheatgerm agglutin-coated yttrium silicate SPA beads for one hour at room temperature with agitation. The beads were then allowed to settle to the bottom of the wells for 1 hr, after which the membrane-associated radioactivity was determined by scintillation counting in a TopCount microplate reader. Ki values were determined using the Cheng-Prusoff equation.

Summary of Materials and Methods Used in A2a Activity Determination:
Materials
  Membranes from CHO-K1 cells expressing the human Adenosine$_{2A}$ receptor (Perkin-Elmer #RBHA2AM400UA).
  The tritiated compound was prepared according to published methods.
  Wheatgerm agglutinin-coated yttrium silicate SPA beads (GE Healthcare #RPNQ0023). Dilute to 25 mg/ml in Assay Buffer.
  Assay Buffer: Dulbecco's calcium and magnesium free phosphate buffered saline+10 mM MgCl$_2$
  Adenosine deaminase (ADA) from calf intestine, 10 mg/2 ml (Roche #10 102 105 001).
  DMSO
  A2a antagonist standard (9-chloro-1-(2-furanyl)-[1,2,4] triazolo[1,5-c]quinazolin-5-amine from Tocris Bioscience)
Compound Dilution
  Make eight 1:3 serial dilutions in 100% DMSO from a 3 mM compound stock.
  Transfer 50 nL of compound into a 384-well OptiPlate (Perkin Elmer).
  Typically, final concentrations of compound used in the assay ranged from 3000 nM to 0.152 nM.
Radioisotope
  Dilute a solution of the tritiated compound to 5.0 nM in assay buffer. This is a 2.5× solution. The final concentration in the assay is 2.0 nM. Calculate the concentration by counting two 5 µL aliquots.
Membrane Preparation
  Use 1.0 µg of membrane/well. Dilute membranes to 33 µg/mL in assay buffer. Treat with 20 µg/mL ADA for 15 minutes at room temperature to degrade endogenous adenosine.
Membrane-Bead Mixture
  Use 100 µg/well wheatgerm agglutinin-coated yttrium silicate SPA beads.
  Mix ADA-treated membranes and SPA beads together for 30 min prior to assay.

Assay Assembly
  To the Perkin-Elmer Optiplate-384 containing the compound titration add 20 μL of 2.5× solution of the tritiated compound and 30 μL of the membrane-bead mixture. Incubate for one hour at room temperature with agitation.
  Include total binding (assay buffer+1% DMSO) and non-specific binding (CGS 15943, 1 μM) wells.
Counting
  Allow the beads to settle for one hour.
  Count in TopCount.
Calculations
  A curve fitting program (i.e., Prism, Activity Base, Chemcart) is used to determine the EC50. The Ki value is calculated using the Cheng-Prusoff equation.

$$Ki=EC50/(1+(radioligand\ concentration/Kd))$$

TABLE 14

| Ex. No. | Human $A_{2A}$ $K_i$ (nM) |
| --- | --- |
| 1 | 12 |
| 2 | 6.2 |
| 3 | 2.9 |
| 4 | 8.3 |
| 5 | 15 |
| 6 | 6.5 |
| 7 | 3.1 |
| 8 | 2.1 |
| 9 | 3.8 |
| 10 | 1.6 |
| 11 | 2.1 |
| 12 | 1.5 |
| 13 | 1.8 |
| 14 | 0.9 |
| 15 | 2.5 |
| 16 | 3.2 |
| 17 | 3.5 |
| 18 | 1.6 |
| 19 | 3.0 |
| 20 | 12 |
| 21 | 3.4 |
| 22 | 1.5 |
| 23 | 1.6 |
| 24 | 1.4 |
| 25 | 1.1 |
| 26 | 3.0 |
| 27 | 7.8 |
| 28 | 11 |
| 29 | 1.6 |
| 30 | 2.6 |
| 31 | 2.2 |
| 32 | 40 |
| 33 | 29 |
| 34 | 11 |
| 35 | 3.0 |
| 36 | 39 |
| 37 | 20 |
| 38 | 27 |
| 39 | 67 |
| 40 | 13 |
| 41 | 3.8 |
| 42 | 11 |
| 43 | 7.8 |
| 44 | 45 |
| 45 | 1.5 |
| 46 | 1.8 |
| 47 | 1.7 |
| 48 | 0.8 |
| 49 | 1.6 |
| 50 | 1.1 |
| 51 | 55 |
| 52 | 40 |
| 53 | 39 |
| 54 | 320 |
| 55 | 22 |
| 56 | 27 |
| 57 | 90 |
| 58 | 1.0 |
| 59 | 6.2 |
| 60 | 0.7 |
| 61 | 1.5 |
| 62 | 3.6 |
| 63 | 36 |
| 64 | 7.7 |
| 65 | 4.2 |
| 66 | 3.0 |
| 67 | 3.5 |
| 68 | 1.2 |
| 69 | 1.8 |
| 70 | 5.2 |
| 71 | 3.9 |
| 72 | 0.9 |
| 73 | 0.9 |
| 74 | 7.1 |
| 75 | 4.2 |
| 76 | 1.8 |
| 77 | 3.9 |
| 78 | 1.4 |
| 79 | 1.3 |
| 80 | 2.6 |
| 81 | 2.4 |
| 82 | 1.5 |
| 83 | 3.8 |
| 84 | 4.9 |
| 85 | 12 |
| 86 | 16 |
| 87 | 7.7 |
| 88 | 4.8 |
| 89 | 6.1 |
| 90 | 12 |
| 91 | 1.2 |
| 92 | 4.0 |
| 93 | 4.8 |
| 94 | 4.1 |
| 95 | 4.3 |
| 96 | 4.1 |
| 97 | 2.2 |
| 98 | 6.6 |
| 99 | 2.7 |
| 100 | 6.5 |
| 101 | 31 |
| 102 | 3.5 |
| 103 | 3.4 |
| 104 | 8.7 |
| 105 | 3.7 |
| 106 | 2.1 |
| 107 | 4.0 |
| 108 | 7.5 |
| 109 | 5.9 |
| 110 | 2.9 |
| 111 | 1.4 |
| 112 | 2.0 |
| 113 | 2.8 |
| 114 | 1.4 |
| 115 | 4.4 |
| 116 | 1.8 |
| 117 | 4.9 |
| 118 | 4.2 |
| 119 | 1.7 |
| 120 | 2.7 |
| 121 | 16 |
| 122 | 110 |
| 123 | 4.9 |
| 124 | 1.6 |
| 125 | 1.1 |
| 126 | 29 |
| 127 | 1.4 |
| 128 | 2.5 |
| 129 | 1.0 |
| 130 | 3.9 |
| 131 | 130 |
| 132 | 56 |
| 133 | 64 |
| 134 | 24 |

TABLE 14-continued

| Ex. No. | Human $A_{2A}$ $K_i$ (nM) |
|---|---|
| 135 | 89 |
| 136 | 25 |
| 137 | 1.9 |
| 138 | 1.0 |
| 139 | 1.5 |
| 140 | 0.8 |
| 141 | 55 |
| 142 | 1.2 |
| 143 | 59 |
| 144 | 1.2 |
| 145 | 140 |
| 146 | 44 |
| 147 | 2.9 |
| 148 | 2.0 |
| 149 | 2.7 |
| 150 | 2.3 |
| 151 | 65 |
| 152 | 5.5 |
| 153 | 170 |
| 154 | 20 |
| 155 | 7.2 |
| 156 | 5.3 |
| 157 | 75 |
| 158 | 19 |
| 159 | 180 |
| 160 | 16 |
| 161 | 32 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:
1. A compound of formula I:

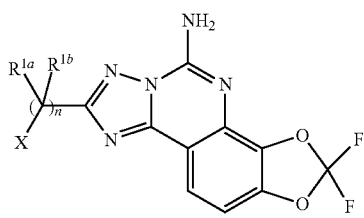

I wherein:
$R^{1a}$ and $R^{1b}$ are independently selected from the group consisting of:
(a) hydrogen,
(b) $C_{1-6}$alkyl, unsubstituted or substituted with one or more halogen, and
(c) $C_{3-6}$cycloalkyl;
X is

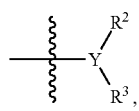

wherein:
Y is CH or N, wherein:
(a) when Y is CH, $R^2$ and $R^3$ are independently selected from the group consisting of:

(i) $C_{1-6}$alkyl, which is substituted with one or more halogen, hydroxy, phenyl (optionally substituted with $C_{1-6}$alkyl, halogen or $CF_3$), $C_{3-6}$cycloalkyl, or a mono- or bicyclic heterocyclic moiety comprising up to 8 carbon atoms and one or more heteroatoms selected from N, S, or O (optionally substituted with $C_{1-6}$alkyl),
(ii) —$C_{3-6}$cycloalkyl, unsubstituted or substituted with one or more halogen or $C_{1-6}$alkyl (optionally substituted with one or more halogen),
(iii) —(C=O)O—$C_{1-6}$alkyl, and
(iv) a mono- or bicyclic heterocyclic moiety comprising up to 8 carbon atoms and one or more heteroatoms selected from N, S, or O (optionally substituted with $C_{1-6}$alkyl),
when Y is N, $R^2$ and $R^3$ are independently selected from the group consisting of:
(i) hydrogen,
(ii) $C_{1-6}$alkyl, which is unsubstituted or substituted with one or more halogen, hydroxy, phenyl (optionally substituted with $C_{1-6}$alkyl, halogen or $CF_3$), $C_{3-6}$cycloalkyl, or a mono- or bicyclic heterocyclic moiety comprising up to 8 carbon atoms and one or more heteroatoms selected from N, S, or O (optionally substituted with $C_{1-6}$alkyl),
(iii) —$C_{3-6}$cycloalkyl, unsubstituted or substituted with one or more halogen or $C_{1-6}$alkyl (optionally substituted with one or more halogen),
(iv) —(C=O)O—$C_{1-6}$alkyl, and
(v) a mono- or bicyclic heterocyclic moiety comprising up to 8 carbon atoms and one or more heteroatoms selected from N, S, or O (optionally substituted with $C_{1-6}$alkyl);
or $R^2$ and $R^3$ are joined to form a cyclic moiety selected from:
(a) $C_{3-6}$cycloalkyl, unsubstituted or substituted with one or more substituents selected from $R^4$, or
(b) a mono- or bicyclic heterocyclic moiety comprising up to 10 carbon atoms and one or more heteroatoms selected from N, S, or O, unsubstituted or substituted on either a carbon or a heteroatom with one or more substituents selected from $R^4$;
$R^4$ is selected from the group consisting of:
(a) hydroxyl,
(b) halogen,
(c) $C_{1-6}$alkyl, optionally substituted with one or more halogen or $C_{3-6}$cycloalkyl,
(d) —$C_{3-6}$cycloalkyl,
(e) —O—$C_{1-6}$alkyl,
(f) —(O)$_m$—(CH$_2$)$_p$O—$C_{1-3}$alkyl,
(g) oxo,
(h) —O$_m$-phenyl, where the phenyl is optionally substituted with halogen, $C_{1-6}$alkyl or —O—$C_{1-6}$alkyl (wherein the $C_{1-6}$alkyl or —O—$C_{1-6}$alkyl are substituted with —O—$C_{1-6}$alkyl), and
(i) heterocycle, which is optionally substituted with one or more halogen, $C_{1-6}$alkyl, or phenyl (optionally substituted with halogen or $CF_3$);
wherein if two $R^4$ substituents are attached to the same carbon atom, they may optionally be joined to form a spirocyclic moiety;
m is 0 or 1 (wherein if m is 0, a bond is present);
n is 1, 2 or 3; and,
p is 1, 2 or 3;
or a pharmaceutically acceptable salt thereof.

2. A compound of claim 1, or a pharmaceutically acceptable salt thereof, wherein $R^{1a}$ and $R^{1b}$ are independently selected from hydrogen, methyl, cyclopropyl, or —$CHF_2$.

3. A compound of claim 1, or a pharmaceutically acceptable salt thereof, wherein X is

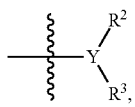

Y is N.

4. A compound of claim 1, or a pharmaceutically acceptable salt thereof, wherein X is

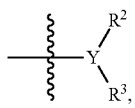

Y is CH.

5. A compound of claim 1, or a pharmaceutically acceptable salt thereof, wherein X is

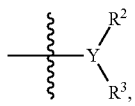

Y is N, and $R^2$ and $R^3$ are independently selected from the group consisting of:
(a) hydrogen,
(b) methyl, which is optionally substituted with one or more halogen, hydroxy, cyclopropyl, phenyl (optionally substituted with $C_{1-6}$alkyl, halogen or —$CF_3$), or a 5- or 6-membered heteroaryl (optionally substituted with $C_{1-6}$alkyl),
(c) —(C=O)O—$CH_3$,
(d) $C_{3-6}$cycloalkyl, which is optionally substituted with —$CF_3$,
(e) saturated or partially unsaturated mono- or bicyclic heterocycle comprising up to 8 carbon atoms and from one to three nitrogen atoms, and
(f) a 5- or 6-membered heteroaryl (optionally substituted with $C_{1-6}$alkyl).

6. A compound of claim 1, or a pharmaceutically acceptable salt thereof, wherein X is

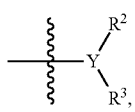

Y is CH or N, and $R^2$ and $R^3$ are joined to form a monocyclic or bicyclic moiety comprising up to 10 carbon atoms and from one to four heteroatom selected from N, S or O, which is unsubstituted or substituted on either a carbon or a heteroatom with one or more substituents selected from $R^4$.

7. A compound of claim 1, or a pharmaceutically acceptable salt thereof, wherein X is

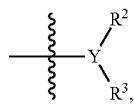

Y is CH or N, and $R^2$ and $R^3$ are joined to form a heterocyclic moiety selected from the group consisting of:

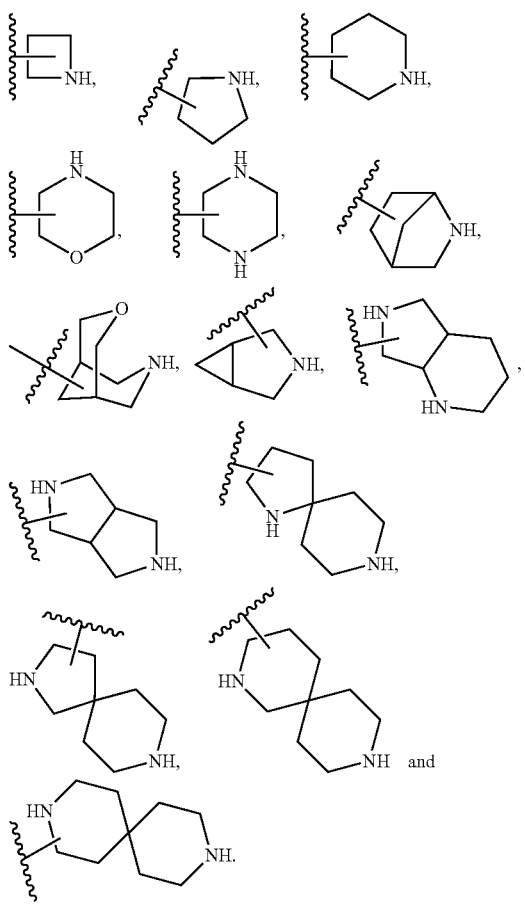

wherein the heterocyclic moiety is unsubstituted or substituted on either a carbon or a heteroatom with one or more substituents selected from $R^4$.

8. A compound of claim 1, or a pharmaceutically acceptable salt thereof, wherein X is

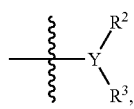

Y is CH or N, and $R^2$ and $R^3$ are joined to form a heterocyclic moiety selected from the group consisting of:

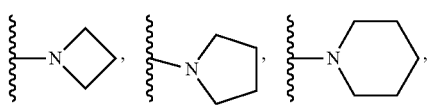

-continued

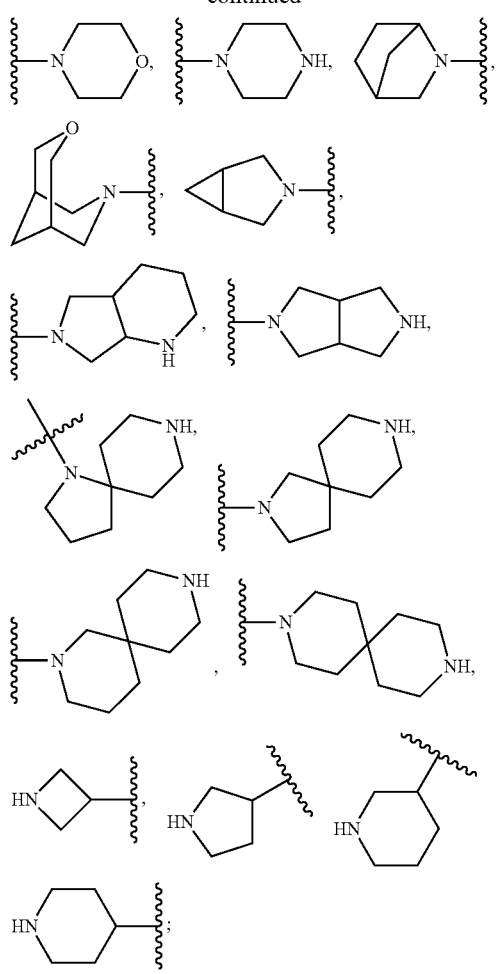

wherein the heterocyclic moiety is unsubstituted or substituted on either a carbon or a heteroatom with one or more substituents selected from $R^4$.

9. A compound of claim 1, or a pharmaceutically acceptable salt thereof, wherein X is

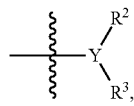

Y is CH or N, and $R^2$ and $R^3$ are joined to form a heterocyclic moiety selected from the group consisting of:

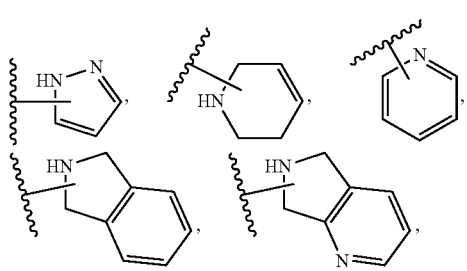

-continued

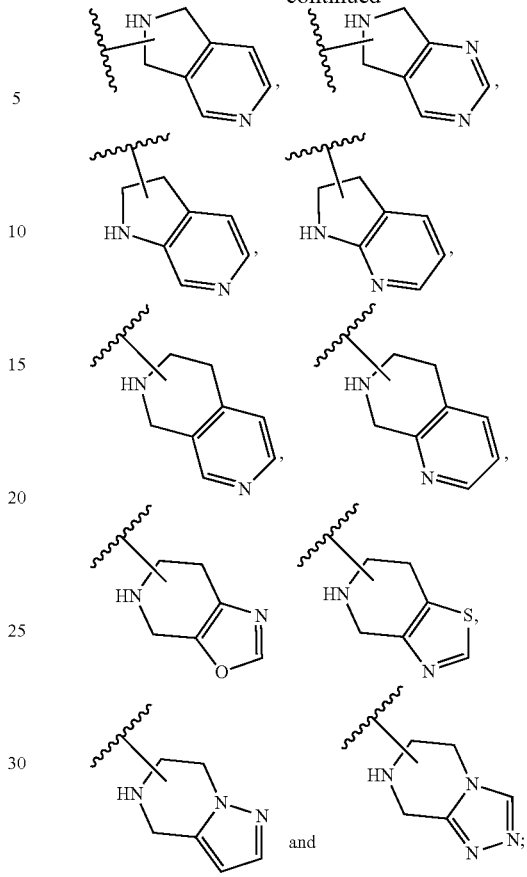

wherein the heterocyclic moiety is unsubstituted or substituted on either a carbon or a heteroatom with one or more substituents selected from $R^4$.

10. A compound of claim 1, or a pharmaceutically acceptable salt thereof, wherein X is

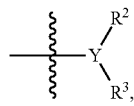

Y is CH or N, and $R^2$ and $R^3$ are joined to form a heterocyclic moiety selected from the group consisting of:

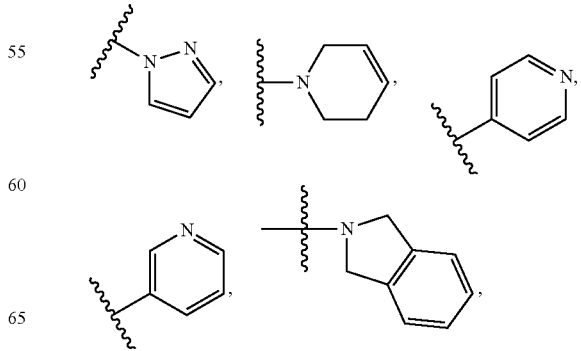

-continued

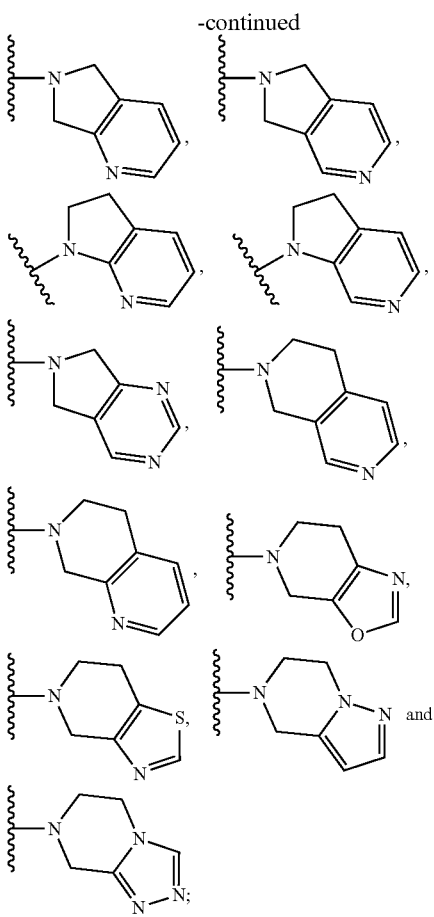

wherein the heterocyclic moiety is unsubstituted or substituted on either a carbon or a heteroatom with one or more substituents selected from R⁴.

11. A compound of claim 1, or a pharmaceutically acceptable salt thereof, wherein X is

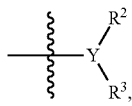

Y is N, and R² and R³ are joined to form a heterocyclic moiety selected from

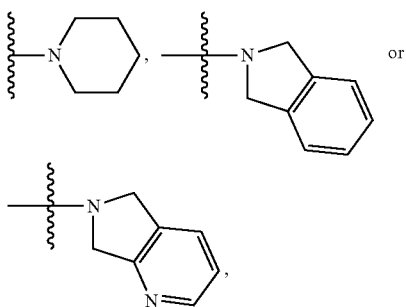

which can be unsubstituted or substituted with one or more substituents selected from R⁴.

12. A compound of claim 1, or a pharmaceutically acceptable salt thereof, wherein R⁴ is selected from the group consisting of:
(a) hydroxy,
(b) fluoro,
(c) chloro,
(d) $C_{1-6}$alkyl, optionally substituted with one or more fluoro, chloro or cyclopropyl,
(e) $C_{3-6}$cycloalkyl,
(f) —O—CH₃,
(g) —(CH₂)₂OCH₃,
(h) —O(CH₂)₂OCH₃,
(i) oxo,
(j) —O-phenyl, which is optionally substituted with fluoro;
(k) phenyl, which is optionally substituted with fluoro, $C_{1-6}$alkyl or —O—$C_{1-6}$alkyl (wherein the $C_{1-6}$alkyl or —O—$C_{1-6}$alkyl are substituted with —O—$C_{1-6}$alkyl) $C_{1-6}$alkyl, and
(l) heterocycle selected from pyridinyl, pyrimidinyl, thiazoyl, thiadiazolyl or piperidinyl, which is optionally substituted with one or more fluoro, chloro or phenyl (optionally substituted with halogen or CF₃).

13. A compound selected from the group consisting of:
8-((2-chloropyridin-3-yl)methyl)-2,2-difluoro-[1,3]dioxolo[4,5-h][1,2,4]triazolo[1,5-c]quinazolin-5-amine;
(S)-2,2-difluoro-8-((2-(3-(4-fluorophenyl)pyrrolidin-1-yl)pyridin-3-yl)methyl)-[1,3]dioxolo[4,5-h][1,2,4]triazolo[1,5-c]quinazolin-5-amine;
(S)-2,2-difluoro-8-((2-(3-(4-(trifluoromethyl)phenyl)pyrrolidin-1-yl)pyridin-3-yl)methyl)-[1,3]dioxolo[4,5-h][1,2,4]triazolo[1,5-c]quinazolin-5-amine;
(8-(2-(5H-pyrrolo[3,4-b]pyridin-6(7H)-yl)ethyl)-2,2-difluoro-[1,3]dioxolo[4,5-h][1,2,4]triazolo[1,5-c]quinazolin-5-amine;
2,2-difluoro-8-{2-[5-(trifluoromethyl)-1,3-dihydro-2H-isoindol-2-yl]ethyl}[1,3]dioxolo[4,5-h][1,2,4]triazolo[1,5-c]quinazolin-5-amine;
2,2-difluoro-8-[2-(5-fluoro-1,3-dihydro-2H-isoindol-2-yl)ethyl][1,3]dioxolo[4,5-h][1,2,4]triazolo[1,5-c]quinazolin-5-amine;
2,2-difluoro-8-{2-[2-(trifluoromethyl)-5,7-dihydro-6H-pyrrolo[3,4-d]pyrimidin-6-yl]ethyl}[1,3]dioxolo[4,5-h][1,2,4]triazolo[1,5-c]quinazolin-5-amine;
8-[2-(3-ethyl-5,6-dihydro[1,2,4]triazolo[4,3-a]pyrazin-7(8H)-yl)ethyl]-2,2-difluoro[1,3]dioxolo[4,5-h][1,2,4]triazolo[1,5-c]quinazolin-5-amine;
8-[2-(1,3-dihydro-2H-pyrrolo[3,4-c]pyridin-2-yl)ethyl]-2,2-difluoro[1,3]dioxolo[4,5-h][1,2,4]triazolo[1,5-c]quinazolin-5-amine;
2,2-difluoro-8-[2-(2-methyl-6,7-dihydro[1,3]oxazolo[5,4-c]pyridin-5(4H)-yl)ethyl][1,3]dioxolo[4,5-h][1,2,4]triazolo[1,5-c]quinazolin-5-amine;
2,2-difluoro-8-[2-(2-methyl-6,7-dihydro[1,3]thiazolo[4,5-c]pyridin-5(4H)-yl)ethyl][1,3]dioxolo[4,5-h][1,2,4]triazolo[1,5-c]quinazolin-5-amine;
8-[2-(2-cyclopropyl-6,7-dihydro[1,3]oxazolo[5,4-c]pyridin-5(4H)-yl)ethyl]-2,2-difluoro[1,3]dioxolo[4,5-h][1,2,4]triazolo[1,5-c]quinazolin-5-amine;
2,2-difluoro-8-[2-(3-fluoroazetidin-1-yl)ethyl][1,3]dioxolo[4,5-h][1,2,4] triazolo[1,5-c]quinazolin-5-amine;
8-[2-(3-ethyl-3-fluoroazetidin-1-yl)ethyl]-2,2-difluoro[1,3]dioxolo[4,5-h][1,2,4]triazolo[1,5-c]quinazolin-5-amine;
8-[2-(3-cyclopropyl-3-fluoroazetidin-1-yl)ethyl]-2,2-difluoro[1,3]dioxolo[4,5-h][1,2,4]triazolo[1,5-c]quinazolin-5-amine;

8-[2-(3,3-difluoroazetidin-1-yl)ethyl]-2,2-difluoro[1,3] dioxolo[4,5-h][1,2,4]triazolo[1,5-c]quinazolin-5-amine;

1-[2-(5-amino-2,2-difluoro[1,3]dioxolo[4,5-h][1,2,4]triazolo[1,5-c]quinazolin-8-yl)ethyl]-3-(trifluoromethyl) azetidin-3-ol;

2,2-difluoro-8-{2-[3-fluoro-3-(trifluoromethyl)azetidin-1-yl]ethyl}[1,3]dioxolo[4,5-h][1,2,4]triazolo[1,5-c] quinazolin-5-amine;

2,2-difluoro-8-{2-[(2R,4S)-4-fluoro-2-methylpyrrolidin-1-yl]ethyl}[1,3]dioxolo[4,5-h][1,2,4]triazolo[1,5-c] quinazolin-5-amine;

8-{2-[(3S,4S)-3,4-difluoropyrrolidin-1-yl]ethyl}-2,2-difluoro[1,3]dioxolo[4,5-h][1,2,4]triazolo[1,5-c]quinazolin-5-amine;

8-[2-(3,3-difluoropyrrolidin-1-yl)ethyl]-2,2-difluoro[1,3] dioxolo[4,5-h][1,2,4]triazolo[1,5-c]quinazolin-5-amine;

8-{2-[(2R)-4,4-difluoro-2-methylpyrrolidin-1-yl]ethyl}-2,2-difluoro[1,3]dioxolo[4,5-h][1,2,4]triazolo[1,5-c] quinazolin-5-amine;

8-{2-[(2S)-4,4-difluoro-2-methylpyrrolidin-1-yl]ethyl}-2,2-difluoro[1,3]dioxolo[4,5-h][1,2,4]triazolo[1,5-c] quinazolin-5-amine;

2,2-difluoro-8-[2-(4-fluoropiperidin-1-yl)ethyl][1,3]dioxolo[4,5-h][1,2,4]triazolo[1,5-c]quinazolin-5-amine;

2,2-difluoro-8-[2-(4-fluoro-4-methylpiperidin-1-yl)ethyl] [1,3]dioxolo[4,5-h][1,2,4]triazolo[1,5-c]quinazolin-5-amine;

8-[2-(3,3-difluoropiperidin-1-yl)ethyl]-2,2-difluoro[1,3] dioxolo[4,5-h][1,2,4]triazolo [1,5-c]quinazolin-5-amine;

8-[2-(4,4-difluoropiperidin-1-yl)ethyl]-2,2-difluoro[1,3] dioxolo[4,5-h][1,2,4]triazolo [1,5-c]quinazolin-5-amine;

8-{2-[(2R)-4,4-difluoro-2-methylpiperidin-1-yl]ethyl}-2,2-difluoro[1,3]dioxolo[4,5-h][1,2,4]triazolo[1,5-c]quinazolin-5-amine;

8-[2-(9,9-difluoro-3-oxa-7-azabicyclo[3.3.1]non-7-yl) ethyl]-2,2-difluoro[1,3]dioxolo [4,5-h][1,2,4]triazolo [1,5-c]quinazolin-5-amine;

8-[2-(3,3-dimethylazetidin-1-yl)ethyl]-2,2-difluoro[1,3] dioxolo[4,5-h][1,2,4]triazolo[1,5-c]quinazolin-5-amine;

8-{2-[(2R,5R)-2,5-dimethylpyrrolidin-1-yl]ethyl}-2,2-difluoro[1,3]dioxolo[4,5-h][1,2,4]triazolo[1,5-c]quinazolin-5-amine;

8-[2-(3-azabicyclo[3.1.0]hex-3-yl)ethyl]-2,2-difluoro[1, 3]dioxolo[4,5-h][1,2,4]triazolo[1,5-c]quinazolin-5-amine;

2,2-difluoro-8-{2-[(3S)-3-phenylpyrrolidin-1-yl]ethyl} [1,3]dioxolo[4,5-h][1,2,4]triazolo[1,5-c]quinazolin-5-amine;

2,2-difluoro-8-{2-[(3R)-3-phenylpyrrolidin-1-yl]ethyl} [1,3]dioxolo[4,5-h][1,2,4]triazolo[1,5-c]quinazolin-5-amine;

2,2-difluoro-8-[2-(4-methylpiperidin-1-yl)ethyl][1,3]dioxolo[4,5-h][1,2,4]triazolo[1,5-c]quinazolin-5-amine;

8-[2-(3,3-dimethylpiperidin-1-yl)ethyl]-2,2-difluoro[1,3] dioxolo[4,5-h][1,2,4]triazolo[1,5-c]quinazolin-5-amine;

2,2-difluoro-8-{2-[(3R)-3-methoxypiperidin-1-yl]ethyl} [1,3]dioxolo[4,5-h][1,2,4]triazolo[1,5-c]quinazolin-5-amine;

2,2-difluoro-8-[2-(4-methyl-3,6-dihydropyridin-1(2H)-yl)ethyl][1,3]dioxolo[4,5-h][1,2,4]triazolo[1,5-c]quinazolin-5-amine;

2,2-difluoro-8-{2-[(2R)-2-methylmorpholin-4-yl]ethyl} [1,3]dioxolo[4,5-h][1,2,4]triazolo[1,5-c]quinazolin-5-amine;

2,2-difluoro-8-{2-[(3S)-3-methylmorpholin-4-yl]ethyl} [1,3]dioxolo[4,5-h][1,2,4]triazolo[1,5-c]quinazolin-5-amine;

8-{2-[(2R,6S)-2,6-dimethylmorpholin-4-yl]ethyl}-2,2-difluoro[1,3]dioxolo[4,5-h][1,2,4]triazolo[1,5-c]quinazolin-5-amine;

2,2-difluoro-8-{2-[(2R)-2-methyl-4-(2-methyl-1,3-thiazol-5-yl)piperazin-1-yl]ethyl}[1,3]dioxolo[4,5-h][1,2,4]triazolo[1,5-c]quinazolin-5-amine;

8-{2-[(2R)-4-(4-chloro-1,2,5-thiadiazol-3-yl)-2-methylpiperazin-1-yl]ethyl}-2,2-difluoro[1,3]dioxolo[4,5-h][1,2,4]triazolo[1,5-c]quinazolin-5-amine;

4-[2-(5-amino-2,2-difluoro[1,3]dioxolo[4,5-h][1,2,4]triazolo[1,5-c]quinazolin-8-yl)ethyl]-1-methylpiperazin-2-one;

4-[2-(5-amino-2,2-difluoro[1,3]dioxolo[4,5-h][1,2,4]triazolo[1,5-c]quinazolin-8-yl)ethyl]-1-(cyclopropylmethyl)piperazin-2-one;

4-[2-(5-amino-2,2-difluoro[1,3]dioxolo[4,5-h][1,2,4]triazolo[1,5-c]quinazolin-8-yl)ethyl]-1-cyclopentylpiperazin-2-one;

4-[2-(5-amino-2,2-difluoro[1,3]dioxolo[4,5-h][1,2,4]triazolo [1,5-c]quinazolin-8-yl)ethyl]-1-(3-fluorophenyl) piperazin-2-one;

2,2-difluoro-8-{2-[(4aR,7aR)-octahydro-6H-pyrrolo[3,4-b]pyridin-6-yl]ethyl}[1,3]dioxolo[4,5-h][1,2,4]triazolo [1,5-c]quinazolin-5-amine;

2,2-difluoro-8-{2-[(3aS)-hexahydropyrrolo[3,4-c]pyrrol-2(1H)-yl]ethyl}[1,3]dioxolo[4,5-h][1,2,4]triazolo[1,5-c]quinazolin-5-amine;

8-[2-(2,8-diazaspiro[4.5]dec-2-yl)ethyl]-2,2-difluoro[1,3] dioxolo[4,5-h][1,2,4]triazolo[1,5-c]quinazolin-5-amine;

8-[2-(3,9-diazaspiro[5.5]undec-3-yl)ethyl]-2,2-difluoro [1,3]dioxolo[4,5-h][1,2,4]triazolo[1,5-c]quinazolin-5-amine;

8-[2-(1,8-diazaspiro[4.5]dec-1-yl)ethyl]-2,2-difluoro[1,3] dioxolo[4,5-h][1,2,4]triazolo[1,5-c]quinazolin-5-amine;

8-[2-(2,9-diazaspiro[5.5]undec-2-yl)ethyl]-2,2-difluoro [1,3]dioxolo[4,5-h][1,2,4]triazolo [1,5-c]quinazolin-5-amine;

8-[2-(2-azaspiro[3.3]hept-6-ylamino)ethyl]-2,2-difluoro [1,3]dioxolo[4,5-h][1,2,4]triazolo[1,5-c]quinazolin-5-amine;

2,2-difluoro-8-(2-{[1-(trifluoromethyl)cyclobutyl] amino}ethyl)[1,3]dioxolo[4,5-h][1,2,4]triazolo[1,5-c] quinazolin-5-amine;

2,2-difluoro-8-(2-{[4-(trifluoromethyl)benzyl] amino}ethyl)[1,3]dioxolo[4,5-h][1,2,4]triazolo[1,5-c] quinazolin-5-amine;

8-(2-{(cyclopropylmethyl)[(4-methyl-1,3-thiazol-2-yl) methyl]amino}ethyl)-2,2-difluoro[1,3]dioxolo[4,5-h] [1,2,4]triazolo[1,5-c]quinazolin-5-amine;

8-(2-{(cyclopropylmethyl)[(2-methyl-1,3-thiazol-5-yl) methyl]amino}ethyl)-2,2-difluoro[1,3]dioxolo[4,5-h] [1,2,4]triazolo[1,5-c]quinazolin-5-amine;

2,2-difluoro-8-{2-[3-(trifluoromethyl)piperidin-1-yl] ethyl}[1,3]dioxolo[4,5-h][1,2,4]triazolo[1,5-c]quinazolin-5-amine;

8-{2-[(2R,6R)-2,6-dimethylmorpholin-4-yl]ethyl}-2,2-difluoro[1,3]dioxolo[4,5-h][1,2,4]triazolo[1,5-c]quinazolin-5-amine;

2,2-difluoro-8-[2-(3-fluoro-3-methylpiperidin-1-yl)ethyl] [1,3]dioxolo[4,5-h][1,2,4]triazolo[1,5-c]quinazolin-5-amine;

8-[2-(6,6-difluoro-2-azabicyclo[2.2.1]hept-2-yl)ethyl]-2, 2-difluoro[1,3]dioxolo[4,5-h][1,2,4]triazolo[1,5-c]quinazolin-5-amine;

8-[2-(3,3-difluoro-2-methylpiperidin-1-yl)ethyl]-2,2-difluoro[1,3]dioxolo[4,5-h][1,2,4]triazolo[1,5-c]quinazolin-5-amine;

1-(2-(5-amino-2,2-difluoro-[1,3]dioxolo[4,5-h][1,2,4]triazolo[1,5-c]quinazolin-8-yl)ethyl)-3-(trifluoromethyl) piperidin-3-ol;

2,2-difluoro-8-(2-(3-fluoro-3-(trifluoromethyl)piperidin-1-yl)ethyl)-[1,3]dioxolo[4,5-h][1,2,4]triazolo[1,5-c] quinazolin-5-amine;

(R)-8-(2-(1H-pyrrolo[3,4-c]pyridin-2(3H)-yl)propyl)-2, 2-difluoro-[1,3]dioxolo[4,5-h][1,2,4]triazolo[1,5-c] quinazolin-5-amine;

8-[(2R)-2-(2,3-dihydro-1H-pyrrolo[2,3-b]pyridin-1-yl) propyl]-2,2-difluoro[1,3]dioxolo[4,5-h][1,2,4]triazolo [1,5-c]quinazolin-5-amine;

8-[(2R)-2-(2,3-dihydro-1H-pyrrolo[2,3-c]pyridin-1-yl) propyl]-2,2-difluoro[1,3]dioxolo[4,5-h][1,2,4]triazolo [1,5-c]quinazolin-5-amine;

8-[(2R)-2-(3,4-dihydro-2,7-naphthyridin-2(1H)-yl)propyl]-2,2-difluoro[1,3]dioxolo[4,5-h][1,2,4]triazolo[1, 5-c]quinazolin-5-amine;

8-[(2R)-2-(5,8-dihydro-1,7-naphthyridin-7(6H)-yl)propyl]-2,2-difluoro[1,3]dioxolo[4,5-h][1,2,4]triazolo[1, 5-c]quinazolin-5-amine;

2,2-difluoro-8-[(2R)-2-(2-methyl-6,7-dihydro[1,3]oxazolo[5,4-c]pyridine-5(4H)-yl)propyl][1,3]dioxolo[4,5-h][1,2,4]triazolo[1,5-c]quinazolin-5-amine;

2,2-difluoro-8-[(2R)-2-(2-methyl-6,7-dihydro[1,3]thiazolo[5,4-c]pyridin-5(4H)-yl)propyl][1,3]dioxolo[4,5-h][1,2,4]triazolo[1,5-c]quinazolin-5-amine;

8-[(2R)-2-(2-cyclopropyl-6,7-dihydro[1,3]oxazolo[5,4-c] pyridin-5(4H)-yl)propyl]-2,2-difluoro[1,3]dioxolo[4, 5-h][1,2,4]triazolo[1,5-c]quinazolin-5-amine;

2,2-difluoro-8-[(2R)-2-(2-methyl-6,7-dihydro[1,3]thiazolo[4,5-c]pyridin-5(4H)-yl)propyl][1,31dioxolo[4,5-h][1,2,4]triazolo[1,5-c]quinazolin-5-amine;

2,2-difluoro-8-[(2R)-2-(2-methyl-6,7-dihydropyrazolo[1, 5-a]pyrazin-5(4H)-yl)propyl][1,3]dioxolo[4,5-h][1,2, 4]triazolo[1,5-c]quinazolin-5-amine;

2,2-difluoro-8-[(2R)-2-(3-fluoro-3-methylazetidin-1-yl) propyl][1,3]dioxolo[4,5-h][1,2,4]triazolo[1,5-c]quinazolin-5-amine;

2,2-difluoro-8-{(2R)-2-[3-fluoro-3-methylpiperidin-1-yl] propyl}[1,3]dioxolo[4,5-h][1,2,4]triazolo[1,5-c]quinazolin-5-amine;

(S)-8-(2-(1H-pyrrolo[3,4-c]pyridin-2(3H)-yl)propyl)-2,2-difluoro-[1,3]dioxolo[4,5-h][1,2,4]triazolo[1,5-c]quinazolin-5-amine;

2,2-difluoro-8-[(2S)-2-(3-fluoro-3-methylazetidin-1-yl) propyl][1,3]dioxolo[4,5-h][1,2,4]triazolo[1,5-c]quinazolin-5-amine;

2,2-difluoro-8-{(2S)-2-[3-fluoro-3-methylpiperidin-1-yl] propyl}[1,3]dioxolo[4,5-h][1,2,4]triazolo[1,5-c]quinazolin-5-amine;

8-[2-(5,7-dihydro-6H-pyrrolo[3,4-b]pyridin-6-yl)propyl]-2,2-difluoro[1,3]dioxolo[4,5-h][1,2,4]triazolo[1, 5-c]quinazolin-5-amine;

8-[2-(3,3-difluoroazetidin-1-yl)propyl]-2,2-difluoro[1,3] dioxolo[4,5-h][1,2,4]triazolo[1,5-c]quinazolin-5-amine;

8-[2-(3,3-difluoropiperidin-1-yl)propyl]-2,2-difluoro[1, 3]dioxolo[4,5-h][1,2,4]triazolo[1,5-c]quinazolin-5-amine;

8-(3,3-difluoro-2-(5H-pyrrolo[3,4-b]pyridin-6(7H)-yl) propyl)-2,2-difluoro-[1,3]dioxolo[4,5-h][1,2,4]triazolo [1,5-c]quinazolin-5-amine;

8-(2-(1H-pyrazol-1-yl)ethyl)-2,2-difluoro-[1,3]dioxolo [4,5-h][1,2,4]triazolo[1,5-c]quinazolin-5-amine;

6-(2-(5-amino-2,2-difluoro-[1,3]dioxolo[4,5-h][1,2,4]triazolo[1,5-c]quinazolin-8-yl)ethyl)-6,7-dihydro-5H-pyrrolo[3,4-b]pyridin-5-one;

2,2-difluoro-8-(2-(3-fluoroazetidin-1-yl)-2-methylpropyl)-[1,3]dioxolo[4,5-h][1,2,4]triazolo[1,5-c]quinazolin-5-amine;

2,2-difluoro-8-((7-(4-fluorophenyl)-4,7-diazaspiro[2.5] octan-4-yl)methyl)-[1,3]dioxolo[4,5-h][1,2,4]triazolo [1,5-c]quinazolin-5-amine;

2,2-difluoro-8-{[7-(5-fluoropyridin-2-yl)-4,7-diazaspiro [2.5]oct-4-yl]methyl}[1,3]dioxolo[4,5-h][1,2,4]triazolo[1,5-c]quinazolin-5-amine;

2,2-difluoro-8-{[7-(3-fluorophenyl)-4,7-diazaspiro[2.5] oct-4-yl]methyl}[1,3]dioxolo[4,5-h][1,2,4]triazolo[1, 5-c]quinazolin-5-amine;

2,2-difluoro-8-({7-[4-(2-methoxyethoxy)phenyl]-4,7-diazaspiro[2.5]oct-4-yl}methyl)[1,3]dioxolo[4,5-h][1,2, 4]triazolo[1,5-c]quinazolin-5-amine;

2,2-difluoro-8-{[(2R)-4-(4-fluorophenyl)-2-methylpiperazin-1-yl]methyl}[1,3]dioxolo[4,5-h][1,2,4]triazolo[1, 5-c]quinazolin-5-amine;

2,2-difluoro-8-{[(2R)-2-methyl-4-(4-methyl-1,3-thiazol-5-yl)piperazin-1-yl]methyl}[1,3]dioxolo[4,5-h][1,2,4] triazolo[1,5-c]quinazolin-5-amine;

8-{[(2R)-4-(4-chloro-1,2,5-thiadiazol-3-yl)-2-methylpiperazin-1-yl]methyl}-2,2-difluoro[1,3]dioxolo[4,5-h][1, 2,4]triazolo[1,5-c]quinazolin-5-amine;

8-((3,3-difluoroazetidin-1-yl)methyl)-2,2-difluoro-[1,3] dioxolo[4,5-h][1,2,4]triazolo[1,5-c]quinazolin-5-amine;

8-[(3,3-dimethylazetidin-1-yl)methyl]-2,2-difluoro[1,3] dioxolo[4,5-h][1,2,4]triazolo[1,5-c]quinazolin-5-amine;

2,2-difluoro-8-[(3-fluoro-3-methylazetidin-1-yl)methyl] [1,3]dioxolo[4,5-h][1,2,4]triazolo[1,5-c]quinazolin-5-amine;

8-[(3-ethyl-3-fluoroazetidin-1-yl)methyl]-2,2-difluoro[1, 3]dioxolo[4,5-h][1,2,4]triazolo[1,5-c]quinazolin-5-amine;

11-[(5-amino-2,2-difluoro[1,3]dioxolo[4,5-h][1,2,4]triazolo[1,5-c]quinazolin-8-yl)methyl]-3-(trifluoromethyl) azetidin-3-ol;

2,2-difluoro-8-{[3-fluoro-3-(trifluoromethyl)azetidin-1-yl]methyl}[1,3]dioxolo[4,5-h][1,2,4]triazolo[1,5-c] quinazolin-5-amine;

8-{[(3S,4S)-3,4-difluoropyrrolidin-1-yl]methyl}-2,2-difluoro[1,3]dioxolo[4,5-h][1,2,4]triazolo[1,5-c]quinazolin-5-amine;

8-[(3,3-difluoropyrrolidin-1-yl)methyl]-2,2-difluoro[1,3] dioxolo[4,5-h][1,2,4]triazolo[1,5-c]quinazolin-5-amine;

2,2-difluoro-8-{[4-(4-fluorophenoxy) piperidin-1-yl] methyl}[1,3]dioxolo[4,5-h][1,2,4]triazolo[1,5-c]quinazolin-5-amine;

8-[(3,3-difluoropiperidin-1-yl)methyl]-2,2-difluoro[1,3] dioxolo[4,5-h][1,2,4]triazolo[1,5-c]quinazolin-5-amine;

8-[(4,4-difluoropiperidin-1-yl)methyl]-2,2-difluoro[1,3]
dioxolo[4,5-h][1,2,4]triazolo[1,5-c]quinazolin-5-
amine;
2,2-difluoro-8-[(5-fluoro-1,3-dihydro-2H-isoindol-2-yl)
methyl][1,3]dioxolo[4,5-h][1,2,4]triazolo[1,5-c]qui-
nazolin-5-amine;
2,2-difluoro-8-{[2-(trifluoromethyl)-5,7-dihydro-6H-pyr-
rolo[3,4-d]pyrimidin-6-yl]methyl}[1,3]dioxolo [4,5-h]
[1,2,4]triazolo[1,5-c]quinazolin-5-amine;
8-[(3-ethyl-5,6-dihydro[1,2,4]triazolo[4,3-a]pyrazin-7
(8H)-yl)methyl]-2,2-difluoro[1,3]dioxolo[4,5-h][1,2,4]
triazolo[1,5-c]quinazolin-5-amine;
2,2-difluoro-8-{[5-(trifluoromethyl)-1,3-dihydro-2H-
isoindol-2-yl]methyl}[1,3]dioxolo[4,5-h][1,2,4]tri-
azolo[1,5-c]quinazolin-5-amine;
2,2-difluoro-8-({[4-(trifluoromethyl)benzyl]
amino}methyl)[1,3]dioxolo[4,5-h][1,2,4]triazolo[1,5-
c]quinazolin-5-amine;
2,2-difluoro-8-({[1-(trifluoromethyl)cyclobutyl]
amino}methyl)[1,3]dioxolo[4,5-h][1,2,4]triazolo[1,5-
c]quinazolin-5-amine;
8-[(dimethylamino)methyl]-2,2-difluoro[1,3]dioxolo[4,
5-h][1,2,4]triazolo[1,5-c]quinazolin-5-amine;
8-({(cyclopropylmethyl)[(4-methyl-1,3-thiazol-2-yl)
methyl]amino}methyl)-2,2-difluoro[1,3]dioxolo[4,5-
h][1,2,4]triazolo[1,5-c]quinazolin-5-amine;
8-((1H-pyrazol-1-yl)methyl)-2,2-difluoro-[1,3]dioxolo[4,
5-h][1,2,4]triazolo[1,5-c]quinazolin-5-amine;
8-[(3,5-dimethyl-1H-pyrazol-1-yl)methyl]-2,2-difluoro
[1,3]dioxolo[4,5-h][1,2,4]triazolo[1,5-c]quinazolin-5-
amine;
8-{[3,5-bis(trifluoromethyl)-1H-pyrazol-1-yl]methyl}-2,
2-difluoro [1,3]dioxolo[4,5-h][1,2,4]triazolo[1,5-c]qui-
nazolin-5-amine;
8-[1-(3,3-difluoroazetidin-1-yl)ethyl]-2,2-difluoro[1,3]
dioxolo[4,5-h][1,2,4]triazolo[1,5-c]quinazolin-5-
amine;
8-{1-[(3S,4S)-3,4-difluoropyrrolidin-1-yl]ethyl}-2,2-dif-
luoro[1,3]dioxolo[4,5-h][1,2,4]triazolo[1,5-c]quinazo-
lin-5-amine;
8-[1-(3,3-difluoropiperidin-1-yl)ethyl]-2,2-difluoro[1,3]
dioxolo[4,5-h][1,2,4]triazolo[1,5-c]quinazolin-5-
amine;
8-(3-(5H-pyrrolo[3,4-b]pyridin-6(7H)-yl)propyl)-2,2-dif-
luoro-[1,3]dioxolo[4,5-h][1,2,4]triazolo[1,5-c]qui-
nazolin-5-amine;
(R)-2,2-difluoro-8-(1-(2,2,2-trifluoroethyl)piperidin-3-
yl)-[1,3]dioxolo[4,5-h][1,2,4]triazolo[1,5-c]quinazo-
lin-5-amine;
(R)-8-(1-(2,2-difluoroethyl)piperidin-3-yl)-2,2-difluoro-
[1,3]dioxolo[4,5-h][1,2,4]triazolo[1,5-c]quinazolin-5-
amine;
2,2-difluoro-8-(1-(3,3,3-trifluoropropyl)piperidin-3-yl)-
[1,3]dioxolo[4,5-h][1,2,4]triazolo[1,5-c]quinazolin-5-
amine;
2,2-difluoro-8-[1-(3-fluorophenyl)piperidin-3-yl][1,3]di-
oxolo[4,5-h][1,2,4]triazolo[1,5-c]quinazolin-5-amine;
8-[1-(3,5-difluorophenyl) piperidin-3-yl]-2,2-difluoro[1,
3]dioxolo[4,5-h][1,2,4]triazolo[1,5-c]quinazolin-5-
amine;
2,2-difluoro-8-(1-pyrimidin-5-ylpiperidin-3-yl)[1,3]di-
oxolo[4,5-h][1,2,4]triazolo[1,5-c]quinazolin-5-amine;
dimethyl[(5-amino-2,2-difluoro[1,3]dioxolo[4,5-h][1,2,
4]triazolo[1,5-c]quinazolin-8-yl)methyl]propanedio-
ate;
2-[(5-amino-2,2-difluoro[1,3]dioxolo[4,5-h][1,2,4]tri-
azolo[1,5-c]quinazolin-8-yl)methyl]propane-1,3-diol;
8-[3-chloro-2-(chloromethyl)propyl]-2,2-difluoro[1,3]di-
oxolo[4,5-h][1,2,4]triazolo[1,5-c]quinazolin-5-amine;
8-[(1-cyclobutylazetidin-3-yl)methyl]-2,2-difluoro[1,3]
dioxolo[4,5-h][1,2,4]triazolo[1,5-c]quinazolin-5-
amine;
8-{[1-(2,2-difluoropropyl)azetidin-3-yl]methyl}-2,2-dif-
luoro[1,3]dioxolo[4,5-h][1,2,4]triazolo[1,5-c]quinazo-
lin-5-amine;
2,2-difluoro-8-[(1-pyridin-2-ylazetidin-3-yl)methyl][1,3]
dioxolo[4,5-h][1,2,4]triazolo[1,5-c]quinazolin-5-
amine;
2,2-difluoro-8-{[1-(3,3,3-trifluoropropyl)pyrrolidin-3-yl]
methyl}[1,3]dioxolo[4,5-h][1,2,4]triazolo[1,5-c]qui-
nazolin-5-amine;
8-{[1-(2,2-difluoroethyl)pyrrolidin-3-yl]methyl}-2,2-dif-
luoro[1,3]dioxolo[4,5-h][1,2,4]triazolo[1,5-c]quinazo-
lin-5-amine;
2,2-difluoro-8-{[1-(2-methoxyethyl)pyrrolidin-3-yl]
methyl}[1,3]dioxolo[4,5-h][1,2,4]triazolo[1,5-c]qui-
nazolin-5-amine;
8-[(2S)-2-amino-2-cyclopropylethyl]-2,2-difluoro[1,3]di-
oxolo[4,5-h][1,2,4]triazolo[1,5-c]quinazolin-5-amine;
8-[(2R)-2-amino-2-cyclopropylethyl]-2,2-difluoro[1,3]
dioxolo[4,5-h][1,2,4]triazolo[1,5-c]quinazolin-5-
amine;
8-[(1S,3S)-3-(3,3-difluoropiperidin-1-yl)cyclopentyl]-2,
2-difluoro[1,3]dioxolo[4,5-h][1,2,4]triazolo[1,5-c]qui-
nazolin-5-amine; or,
8-[(1S,3R)-3-(3,3-difluoropiperidin-1-yl)cyclopentyl]-2,
2-difluoro[1,3]dioxolo[4,5-h][1,2,4]triazolo[1,5-c]qui-
nazolin-5-amine;
or a pharmaceutically acceptable salt thereof.

14. A pharmaceutical composition that comprises an inert carrier and a compound of claim 1 or a pharmaceutically acceptable salt thereof.

* * * * *

UNITED STATES PATENT AND TRADEMARK OFFICE
CERTIFICATE OF CORRECTION

PATENT NO. : 11,046,714 B2
APPLICATION NO. : 14/914843
DATED : June 29, 2021
INVENTOR(S) : Amjad et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 194 days.

Signed and Sealed this
Thirteenth Day of December, 2022

Katherine Kelly Vidal
*Director of the United States Patent and Trademark Office*